US012686846B2

(12) United States Patent
Jin et al.

(10) Patent No.: US 12,686,846 B2
(45) Date of Patent: Jul. 21, 2026

(54) PLANT SWEET AND YEAST MSF TRANSPORTER CAPABLE OF TRANSPORTING DIFFERENT SUGARS SIMULTANEOUSLY

(71) Applicant: THE BOARD OF TRUSTEES OF THE UNIVERSITY OF ILLINOIS, Urbana, IL (US)

(72) Inventors: Yong-Su Jin, Urbana, IL (US); Nurzhan Kuanyshev, Urbana, IL (US); Jing-Jing Liu, Moraga, CA (US); Anshu Deewan, Urbana, IL (US); Christopher V. Rao, Urbana, IL (US); Balaji Panneerselvam, Urbana, IL (US); Diwakar Shukla, Urbana, IL (US); Sujit Jagtap, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 894 days.

(21) Appl. No.: 17/918,040

(22) PCT Filed: Apr. 9, 2021

(86) PCT No.: PCT/US2021/026548
§ 371 (c)(1),
(2) Date: Oct. 10, 2022

(87) PCT Pub. No.: WO2021/207584
PCT Pub. Date: Oct. 14, 2021

(65) Prior Publication Data
US 2023/0175021 A1 Jun. 8, 2023

Related U.S. Application Data

(60) Provisional application No. 63/008,263, filed on Apr. 10, 2020.

(51) Int. Cl.
| | |
|---|---|
| *C12N 1/18* | (2026.01) |
| *C07K 14/39* | (2006.01) |
| *C07K 14/43* | (2006.01) |
| *C12N 1/185* | (2026.01) |
| *C12P 7/10* | (2006.01) |

(52) U.S. Cl.
CPC .............. *C12N 1/185* (2021.05); *C07K 14/39* (2013.01); *C07K 14/43* (2013.01); *C12P 7/10* (2013.01)

(58) Field of Classification Search
CPC .. C12N 1/18; C12N 1/185; C12P 7/10; C07K 14/39; C07K 14/43
See application file for complete search history.

(56) References Cited

U.S. PATENT DOCUMENTS

| | | | |
|---|---|---|---|
| 4,366,246 | A | 12/1982 | Riggs |
| 4,945,050 | A | 7/1990 | Sanford et al. |
| 7,205,453 | B2 | 4/2007 | Altier et al. |
| 9,562,081 | B2 | 2/2017 | Frommer et al. |
| 10,266,854 | B2 | 4/2019 | Lee |
| 2006/0218670 | A1 | 9/2006 | Joshi et al. |
| 2006/0248616 | A1 | 11/2006 | Oishi et al. |
| 2015/0176014 | A1* | 6/2015 | Jeffries ..................... C12P 7/18 435/320.1 |
| 2016/0355835 | A1* | 12/2016 | Frommer ........... C12N 15/8245 |
| 2018/0142268 | A1 | 5/2018 | Ghisoni |

FOREIGN PATENT DOCUMENTS

| | | |
|---|---|---|
| WO | 2012019308 A1 | 2/2012 |
| WO | 2015184327 A1 | 12/2015 |
| WO | 2016012429 A1 | 1/2016 |

OTHER PUBLICATIONS

Chen et al. Nature 2010, V468, pp. 527-532. (Year: 2010).*
International Preliminary Report on Patentability issued in International Application No. PCT/US2021/026548, dated Oct. 20, 2022, 8 pages.
International Search Report and Written Opinion issued in International Application No. PCT/US2021/026548, dated Oct. 18, 2021, 12 pages.
Knoshaug et al, "Lipid accumulation from glucose and xylose in an engineered, naturally oleaginous strain of *Saccharomyces cerevisiae*", Biofuel Research Journal, vol. 18, pp. 800-805, (2018).
Robak et al, "Review of Second Generation Bioethanol Production from Residual Biomass", Food Technology & Biotechnology, vol. 56, No. 2, pp. 174-187, Jul. 18, 2017.
Ko et al, "Ethanol production from lignocellulosic hydrolysates using engineered *Saccharomyces cerevisiae* harboring xylose isomerase-based pathway", Bioresource Technology, vol. 209, pp. 290-296, Dec. 22, 2015.
Kim et al, "Simultaneous co-fermentation of mixed sugars: a promising strategy for producing cellulosic ethanol", Trends in Biotechnology, vol. 30, No. 5, pp. 274-282, May 2012.
Lee et al, "Microbial metabolic engineering to produce alcohols from cellulosic hydrolysates", CABBI poster 2018, https://dev.cabbi. bio/wp-content/uploads/2018/02/ResearchPoster-CABBI-JIN.pdf.
Runquist, et al, "Challenges in co-fermentation of lignocelluloses-dervived sugars using baker's yeast", Bioalcohol Production, chapter 9, 22 pages, (2010).

(Continued)

*Primary Examiner* — Tekchand Saidha
(74) *Attorney, Agent, or Firm* — Lathrop GPM LLP; Lisa Hillman

(57) ABSTRACT

The present disclosure provides genetically engineered microorganisms for the simultaneous fermentation of pentose and hexose sugars, for example, glucose and xylose. The microorganisms can be modified to express AtSWEET polypeptides, LST1 polypeptides, mutants thereof, homologs thereof or combinations thereof. Also provided are methods of co-fermenting hexose and pentose sugars, methods of increasing the conversion of lignocellulosic biomass via microbial fermentation, and methods of generating biofuel.

15 Claims, 25 Drawing Sheets

Specification includes a Sequence Listing.

(56) References Cited

OTHER PUBLICATIONS

Zhao et al, "Medium optimization for lipid production through co-fermentation of clucose and xylose by the oleaginous yeasr Lipomyces starkeyi", Eur. J. Lipid Sci. Technol., vol. 110, pp. 405-412, Sep. 16, 2007.

* cited by examiner

A

B

C

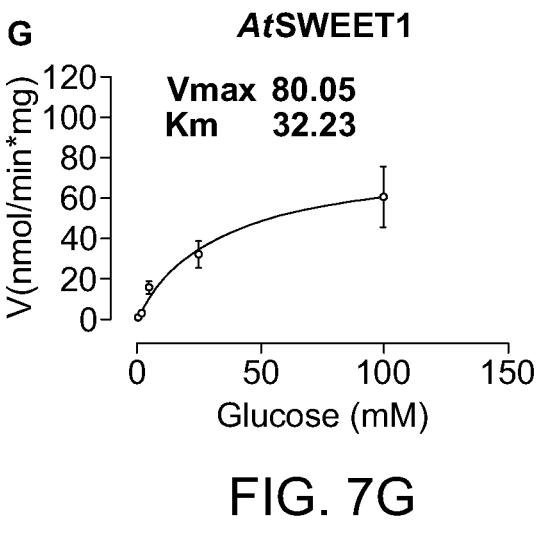
FIG. 7G
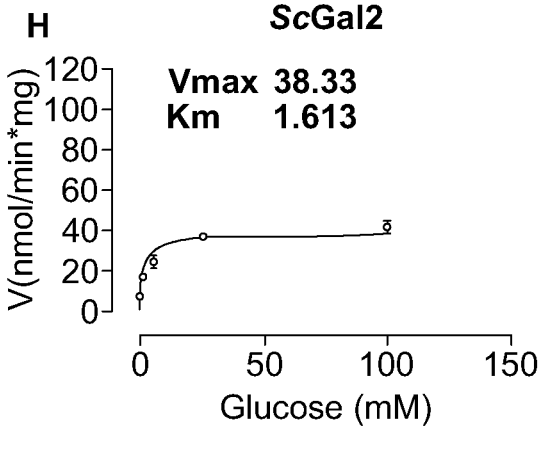
FIG. 7H
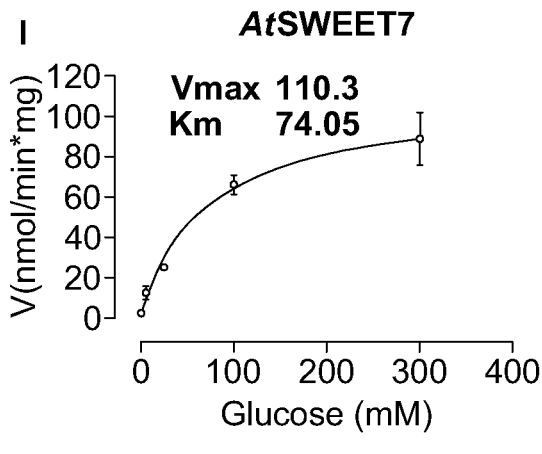
FIG. 7I
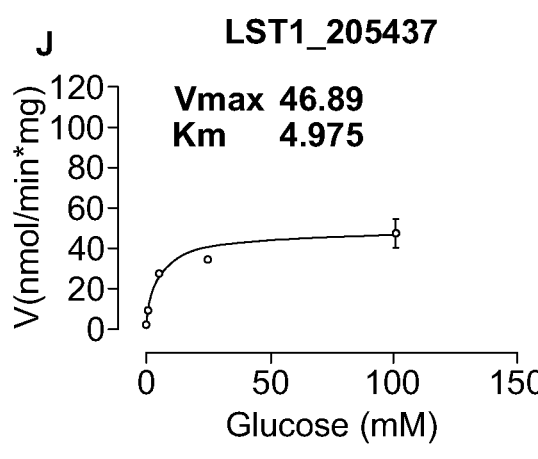
FIG. 7J A   LST1 (OF)-glucose
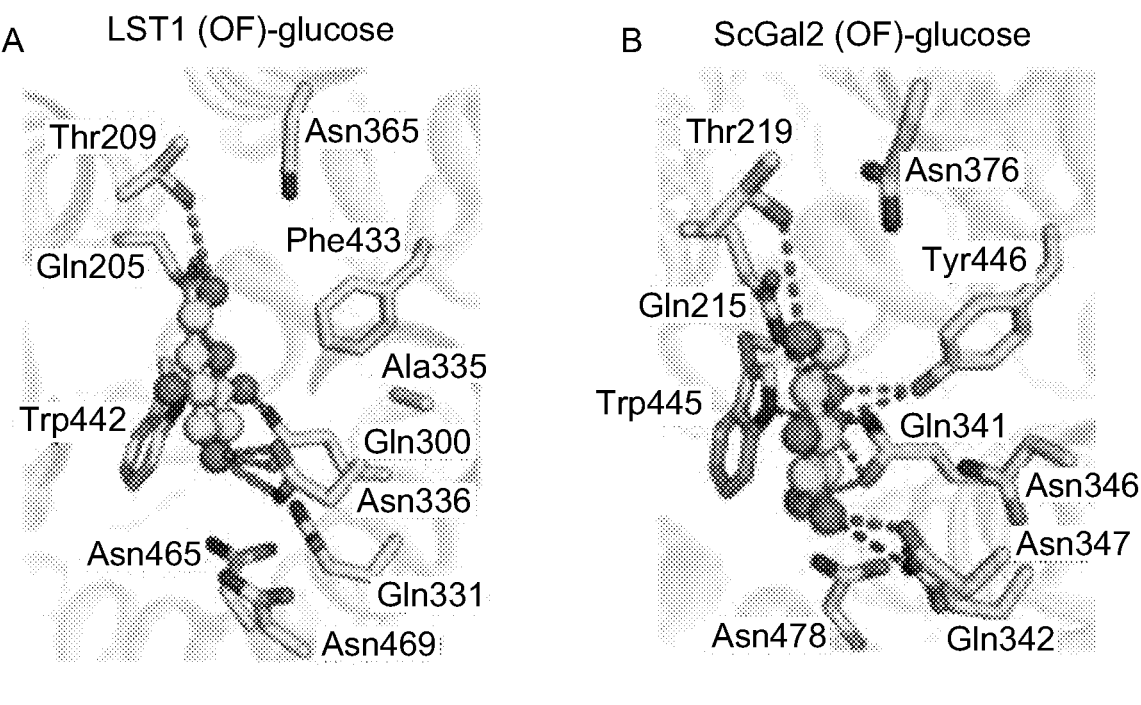
FIG. 9A
B   ScGal2 (OF)-glucose
FIG. 9B
C   LST1 (OF)-xylose
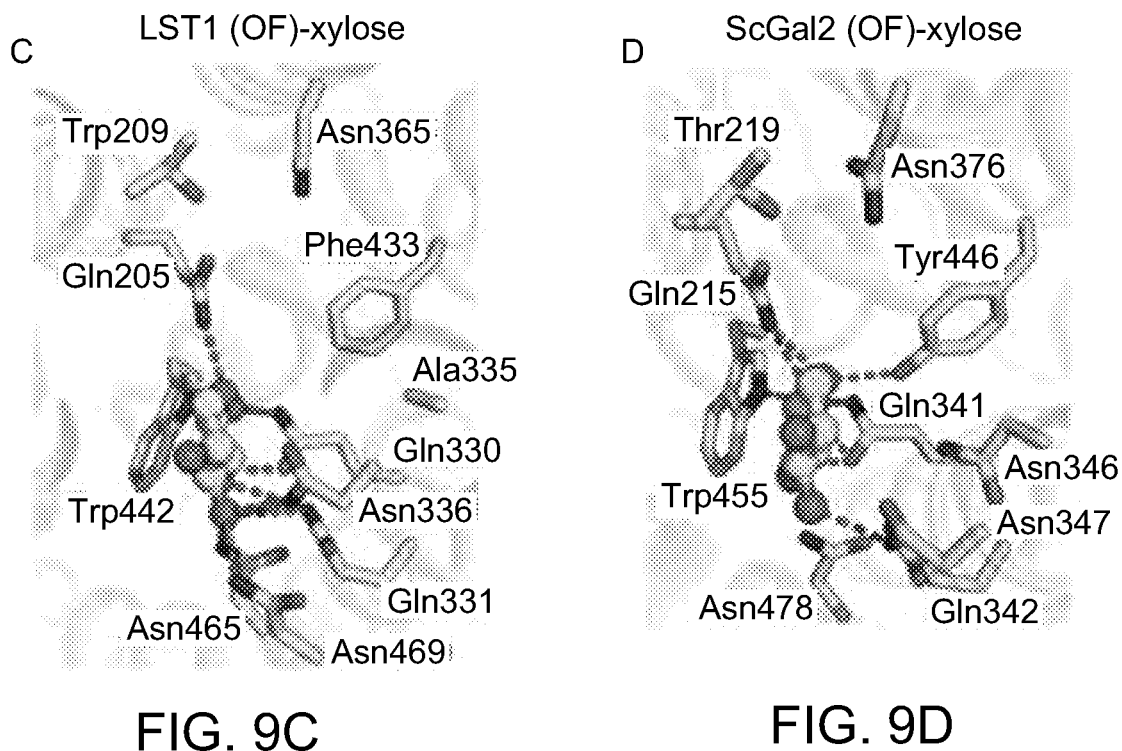
FIG. 9C
D   ScGal2 (OF)-xylose
FIG. 9D

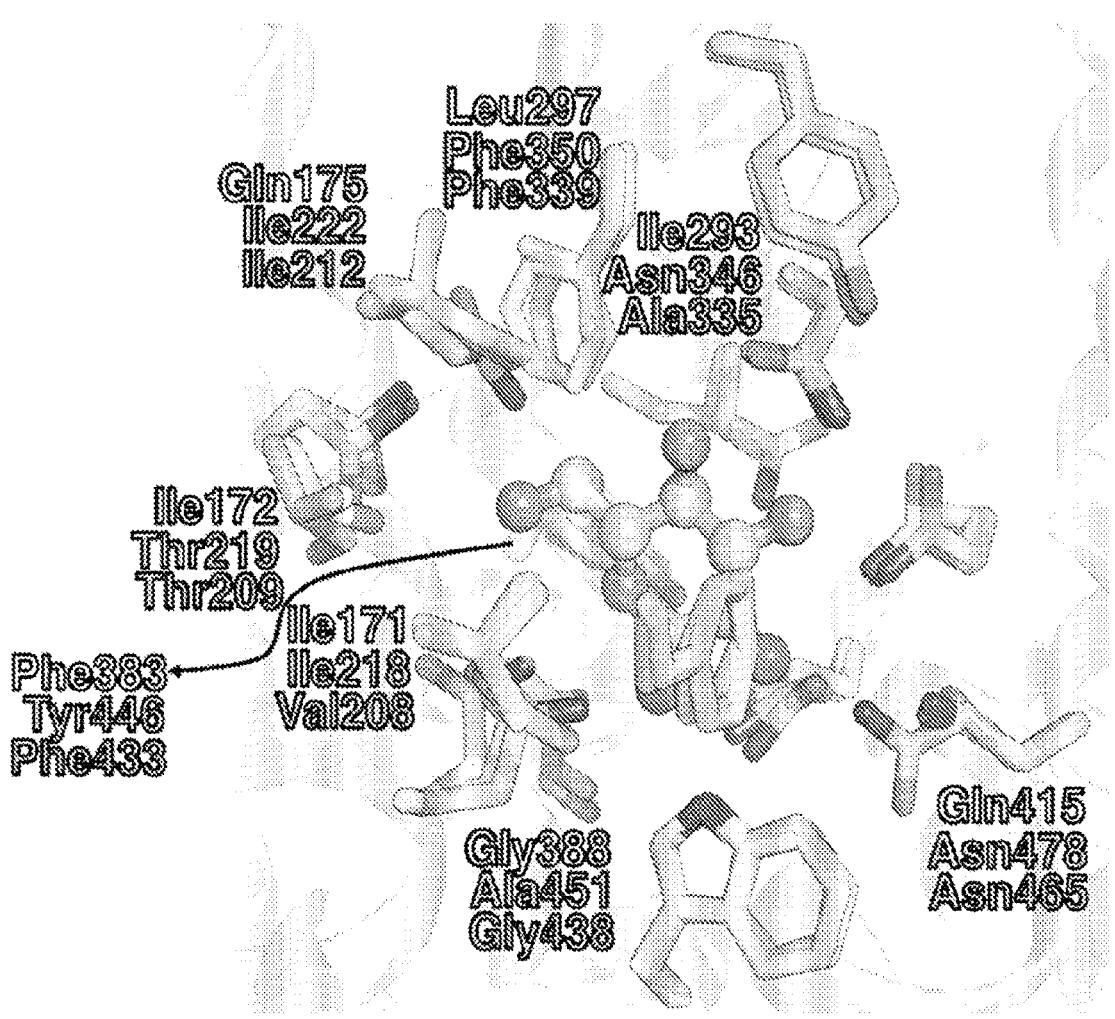
FIG. 10
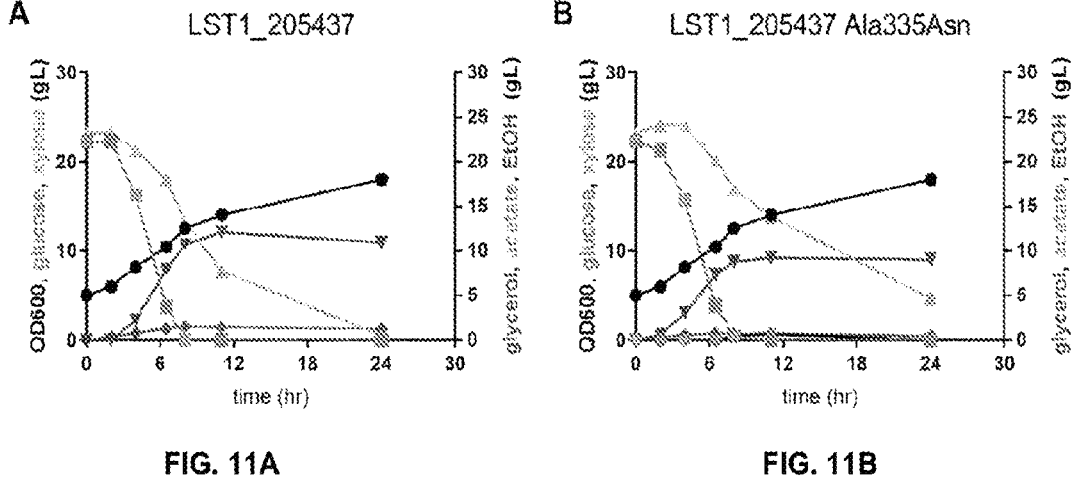
FIG. 11A                    FIG. 11B

A

B

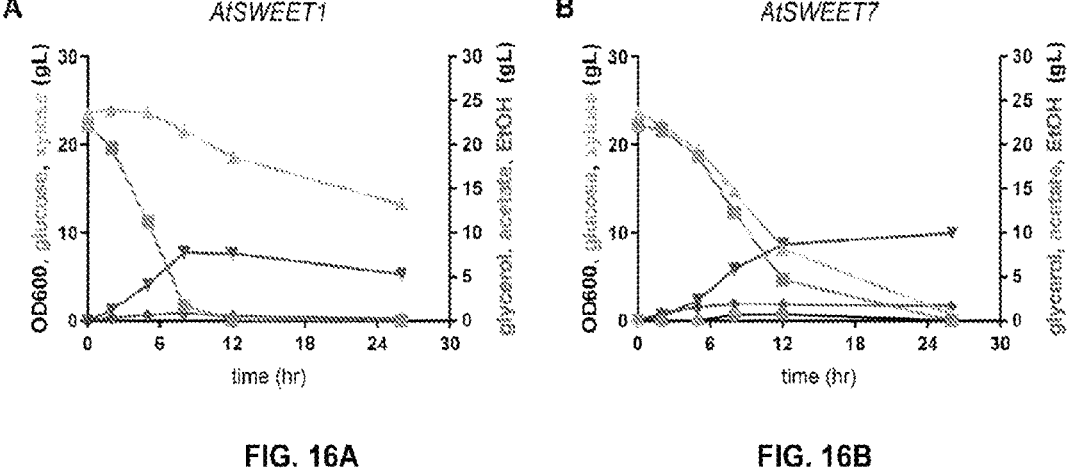
FIG. 16A          FIG. 16B
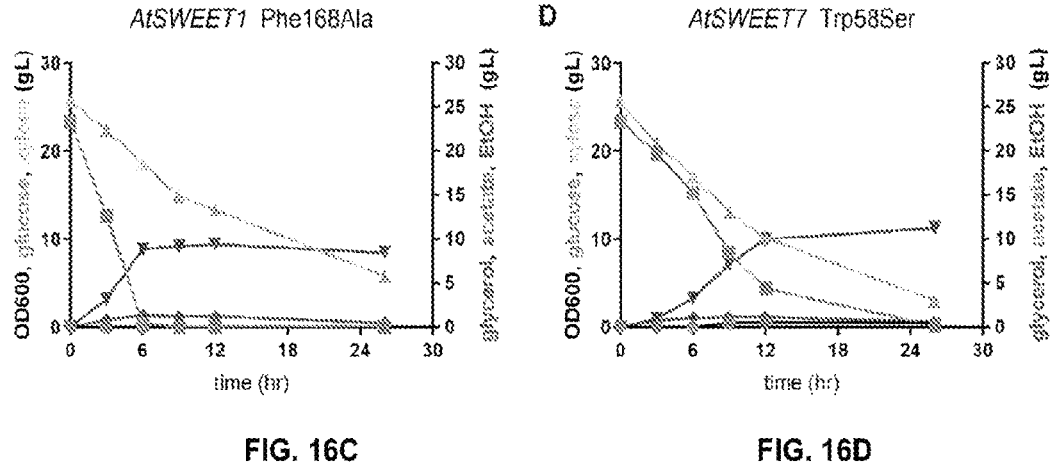
FIG. 16C          FIG. 16D

SEQUENCE LISTING

<160> NUMBER OF SEQ ID NOS: 32

<210> SEQ ID NO 1
<211> LENGTH: 247
<212> TYPE: PRT
<213> ORGANISM: Artificial Sequence
<220> FEATURE:
<223> OTHER INFORMATION: Arabidopsis thaliana SWEET1 (AtSWEET1)
        transporter polypeptide

<400> SEQUENCE: 1

Met Asn Ile Ala His Thr Ile Phe Gly Val Phe Gly Asn Ala Thr Ala
1               5                   10                  15

Leu Phe Leu Phe Leu Ala Pro Ser Ile Thr Phe Lys Arg Ile Ile Lys
            20                  25                  30

Asn Lys Ser Thr Glu Gln Phe Ser Gly Ile Pro Tyr Pro Met Thr Leu
        35                  40                  45

Leu Asn Cys Leu Leu Ser Ala Trp Tyr Gly Leu Pro Phe Val Ser Lys
    50                  55                  60

Asp Asn Thr Leu Val Ser Thr Ile Asn Gly Thr Gly Ala Val Ile Glu
65                  70                  75                  80

Thr Val Tyr Val Leu Ile Phe Leu Phe Tyr Ala Pro Lys Lys Glu Lys
                85                  90                  95

Ile Lys Ile Phe Gly Ile Phe Ser Cys Val Leu Ala Val Phe Ala Thr
            100                 105                 110

Val Ala Leu Val Ser Leu Phe Ala Leu Gln Gly Asn Gly Arg Lys Leu
        115                 120                 125

```
Phe Cys Gly Leu Ala Ala Thr Val Phe Ser Ile Ile Met Tyr Ala Ser
    130                 135                 140

Pro Leu Ser Ile Met Arg Leu Val Val Lys Thr Lys Ser Val Glu Phe
145                 150                 155                 160

Met Pro Phe Phe Leu Ser Leu Phe Val Phe Leu Cys Gly Thr Ser Trp
                165                 170                 175

Phe Val Tyr Gly Leu Ile Gly Arg Asp Pro Phe Val Ala Ile Pro Asn
                180                 185                 190

Gly Phe Gly Cys Ala Leu Gly Thr Leu Gln Leu Ile Leu Tyr Phe Ile
                195                 200                 205

Tyr Cys Gly Asn Lys Gly Glu Lys Ser Ala Asp Ala Gln Lys Asp Glu
    210                 215                 220

Lys Ser Val Glu Met Lys Asp Asp Glu Lys Lys Gln Asn Val Val Asn
225                 230                 235                 240

Gly Lys Gln Asp Leu Gln Val
                245

<210> SEQ ID NO 2
<211> LENGTH: 251
<212> TYPE: PRT
<213> ORGANISM: Artificial Sequence
<220> FEATURE:
<223> OTHER INFORMATION: Arabidopsis thaliana SWEET4 (AtSWEET4)
      transporter polypeptide

<400> SEQUENCE: 2

Met Val Asn Ala Thr Val Ala Arg Asn Ile Ala Gly Ile Cys Gly Asn
1               5                   10                  15

Val Ile Ser Leu Phe Leu Phe Leu Ser Pro Ile Pro Thr Phe Ile Thr
                20                  25                  30

Ile Tyr Lys Lys Lys Lys Val Glu Glu Tyr Lys Ala Asp Pro Tyr Leu
            35                  40                  45

Ala Thr Val Leu Asn Cys Ala Leu Trp Val Phe Tyr Gly Leu Pro Met
    50                  55                  60

Val Gln Pro Asp Ser Leu Leu Val Ile Thr Ile Asn Gly Thr Gly Leu
65                  70                  75                  80

Ala Ile Glu Leu Val Tyr Leu Ala Ile Phe Phe Phe Ser Pro Thr
                85                  90                  95

Ser Arg Lys Val Lys Val Gly Leu Trp Leu Ile Gly Glu Met Val Phe
                100                 105                 110

Val Gly Ile Val Ala Thr Cys Thr Leu Leu Leu Phe His Thr His Asn
            115                 120                 125

Gln Arg Ser Ser Phe Val Gly Ile Phe Cys Val Ile Phe Val Ser Leu
    130                 135                 140

Met Tyr Ile Ala Pro Leu Thr Ile Met Ser Lys Val Ile Lys Thr Lys
145                 150                 155                 160

Ser Val Lys Tyr Met Pro Phe Ser Leu Ser Leu Ala Asn Phe Leu Asn
                165                 170                 175

Gly Val Val Trp Val Ile Tyr Ala Leu Ile Lys Phe Asp Leu Phe Ile
                180                 185                 190

Leu Ile Gly Asn Gly Leu Gly Thr Val Ser Gly Ala Val Gln Leu Ile
            195                 200                 205

Leu Tyr Ala Cys Tyr Tyr Lys Thr Thr Pro Lys Asp Asp Glu Asp Glu
    210                 215                 220

Glu Asp Glu Glu Asn Leu Ser Lys Val Asn Ser Gln Leu Gln Leu Ser
225                 230                 235                 240
```

Gly Asn Ser Gly Gln Ala Lys Arg Val Ser Ala
                245                 250

<210> SEQ ID NO 3
<211> LENGTH: 258
<212> TYPE: PRT
<213> ORGANISM: Artificial Sequence
<220> FEATURE:
<223> OTHER INFORMATION: Arabidopsis thaliana SWEET7 (AtSWEET7)
      transporter polypeptide

<400> SEQUENCE: 3

Met Val Phe Ala His Leu Asn Leu Leu Arg Lys Ile Val Gly Ile Ile
1               5                   10                  15

Gly Asn Phe Ile Ala Leu Cys Leu Phe Leu Ser Pro Thr Pro Thr Phe
                20                  25                  30

Val Arg Ile Val Lys Lys Lys Ser Val Glu Glu Tyr Ser Pro Ile Pro
            35                  40                  45

Tyr Leu Ala Thr Leu Ile Asn Cys Leu Val Trp Val Leu Tyr Gly Leu
    50                  55                  60

Pro Thr Val His Pro Asp Ser Thr Leu Val Ile Thr Ile Asn Gly Thr
65                  70                  75                  80

Gly Ile Leu Ile Glu Ile Val Phe Leu Thr Ile Phe Phe Val Tyr Cys
                85                  90                  95

Gly Arg Gln Lys Gln Arg Leu Ile Ile Ser Ala Val Ile Ala Ala Glu
                100                 105                 110

Thr Ala Phe Ile Ala Ile Leu Ala Val Leu Val Leu Thr Leu Gln His
        115                 120                 125

Thr Thr Glu Lys Arg Thr Met Ser Val Gly Ile Val Cys Cys Val Phe
    130                 135                 140

Asn Val Met Met Tyr Ala Ser Pro Leu Ser Val Met Lys Met Val Ile
145                 150                 155                 160

Lys Thr Lys Ser Val Glu Phe Met Pro Phe Trp Leu Ser Val Ala Gly
                165                 170                 175

Phe Leu Asn Ala Gly Val Trp Thr Ile Tyr Ala Leu Met Pro Phe Asp
                180                 185                 190

Pro Phe Met Ala Ile Pro Asn Gly Ile Gly Cys Leu Phe Gly Leu Ala
        195                 200                 205

Gln Leu Ile Leu Tyr Gly Ala Tyr Tyr Lys Ser Thr Lys Arg Ile Met
    210                 215                 220

Ala Glu Arg Glu Asn Gln Pro Gly Tyr Val Gly Leu Ser Ser Ala Ile
225                 230                 235                 240

Ala Arg Thr Gly Ser Glu Lys Thr Ala Asn Thr Asn Gln Glu Pro Asn
                245                 250                 255

Asn Val

<210> SEQ ID NO 4
<211> LENGTH: 603
<212> TYPE: PRT
<213> ORGANISM: Artificial Sequence
<220> FEATURE:
<223> OTHER INFORMATION: Lipomyces starkeyi LST1_204537 transporter
      polypeptide

<400> SEQUENCE: 4

Met Gly Phe Leu Gly Phe Leu Asn Arg Ser Gln Ala Ser Glu Pro Val
1               5                   10                  15

```
Glu Lys Glu Ser Thr Ala Thr Thr Pro Ser Glu Gly Arg Thr Pro Gln
            20                  25                  30

Arg Pro Leu Ser Pro Ala Val Gly Val Pro Leu Glu Gln Asp Phe Glu
            35                  40                  45

Thr Gln Leu Ser Ala Lys Asp Ala Pro Leu Leu Ala Phe Ile Leu Gly
            50                  55                  60

Gly Val Ala Ser Val Gly Gly Phe Met Phe Gly Tyr Gln Thr Gly Gln
65                  70                  75                  80

Ile Ser Gly Phe Leu Glu Met Ser Asp Phe Lys Thr Arg Phe Ala Ala
                85                  90                  95

Cys Asn Ser Gln Thr Gly Gln Cys Thr Phe Ser Ala Ala Arg Gln Gly
                100                 105                 110

Thr Ile Val Gly Leu Phe Ser Ile Gly Thr Leu Ile Gly Ser Leu Ile
                115                 120                 125

Ala Ala Pro Ile Ala Asp Arg Ile Gly Arg Arg Leu Thr Ile Ser Phe
            130                 135                 140

Trp Ala Phe Phe Phe Met Ile Gly Thr Val Leu Glu Ile Ser Ser Ser
145                 150                 155                 160

His Val Trp Val Gln Phe Ala Met Gly Arg Phe Val Gly Gly Leu Gly
                165                 170                 175

Ile Gly Ala Leu Ser Val Val Val Pro Met Tyr Gln Ser Glu Ser Thr
                180                 185                 190

Pro Arg Met Ile Arg Gly Val Ile Val Ser Ser Tyr Gln Leu Met Val
            195                 200                 205

Thr Leu Gly Ile Trp Leu Ala Tyr Met Ile Asn Trp Gly Thr Glu Ser
            210                 215                 220

Leu Gln Gly Ser Gln Ser Trp Arg Ile Thr Asn Gly Met Ser Phe Leu
225                 230                 235                 240

Trp Ala Leu Val Leu Gly Ile Ala Ile Leu Gly Leu Pro Glu Ser Pro
                245                 250                 255

Arg Tyr Ala Tyr Arg Val Gly Arg Glu Glu Glu Ala Arg Lys Asn Met
            260                 265                 270

Ala Arg Leu Tyr Lys Leu Ser Pro Asn His Pro Ile Ile Asn Leu Glu
            275                 280                 285

Ile Gln Glu Ile Gln Glu Lys Leu Asp Ala Glu Arg Val Gly Gly Asp
            290                 295                 300

His Pro Trp Tyr Glu Ile Phe Thr Gly Pro Arg Met Leu Tyr Arg Thr
305                 310                 315                 320

Ile Leu Gly Met Val Leu Gln Ala Gly Gln Gln Leu Thr Gly Ala Asn
                325                 330                 335

Tyr Phe Phe Tyr Tyr Gly Thr Thr Val Phe Ser Ala Thr Gly Leu Ser
            340                 345                 350

Asn Ser Tyr Val Thr Gln Ile Ile Leu Gly Ser Val Asn Val Gly Gly
            355                 360                 365

Thr Ile Ala Gly Leu Trp Leu Ile Glu Asn Cys Gly Arg Arg Lys Ala
            370                 375                 380

Leu Met Gly Gly Ala Ala Trp Met Phe Met Cys Phe Met Val Phe Ala
385                 390                 395                 400

Phe Val Gly His Phe Ser Leu Asp His Gln Asn Pro Glu Ala Thr Pro
                405                 410                 415

Gln Ala Gly Ala Ala Leu Val Val Phe Ser Cys Leu Phe Ile Ile Ala
            420                 425                 430

Phe Ala Met Thr Trp Gly Pro Ile Val Trp Ala Ile Val Gly Glu Leu
```

```
           435              440              445

Tyr Pro Ala Arg Tyr Arg Ala Thr Cys Met Gly Leu Ala Thr Ser Ser
    450              455              460

Asn Trp Leu Phe Asn Phe Leu Ile Gly Phe Phe Thr Thr Phe Ile Thr
465              470              475              480

Gly Asp Ile Asp Tyr Leu Tyr Gly Leu Val Phe Ala Gly Cys Cys Phe
             485              490              495

Ala Leu Phe Phe Ile Val Tyr Phe Phe Val Ile Glu Thr Lys Gly Arg
             500              505              510

Ser Leu Glu Glu Ile Asp Thr Met Tyr Val Leu His Val Asn Pro Ile
             515              520              525

Asn Ser Ala Lys Trp Asp Ser Ser Gln Leu Met Arg Asp Gly Asp Gly
    530              535              540

Leu Val Asn Thr Asp Asp Leu Tyr Leu Glu Ala Gly Gly Asn Arg Phe
545              550              555              560

Ala Lys Asp Glu His Ser Ala His Glu Met Ile Pro Ser His Asp Glu
             565              570              575

Asn Ala Pro Gly Pro Ser His Thr Ser His Ala Asp Ile Glu Lys Ala
             580              585              590

Glu Ser Ser Gly Ala Glu Ser Arg Asp Ala Leu
             595              600
```

<210> SEQ ID NO 5
<211> LENGTH: 744
<212> TYPE: DNA
<213> ORGANISM: Artificial Sequence
<220> FEATURE:
<223> OTHER INFORMATION: Arabidopsis thaliana SWEET1 (AtSWEET1) codon
      optimized DNA sequences used for SR8D8 expression

<400> SEQUENCE: 5

```
atgaacatcg ctcacactat cttcggcgtt ttcggaaatg caactgctct gtttctttc      60 ttggctcctt cgataacatt caagagaatc atcaagaaca atccactga acaattctct      120 ggtatccctt atccaatgac tctcctcaac tgtctcctct ctgcttggta tggacttccc      180
tttgtgtcaa aagacaacac acttgtgagc acaatcaatg gcacaggagc agtgatcgaa      240
acagtctacg tgttaatctt tcttttctac gcaccaaaga aggagaaaat taagatcttt      300
ggtatcttct cttgcgtttt ggctgtattc gcaacagtag ctctcgtctc tctctttgct      360
cttcaaggaa acggtagaaa actcttttgt ggtctcgcag ctactgtttt ctccatcatc      420
atgtacgctt ctccactctc catcatgaga ttggtggtaa agacgaagag tgtagagttt      480
atgccattct ttttgtcact ctttgtcttc ctctgtggta cttcgtggtt cgtctatggt      540
ctaatcggtc gtgacccttt tgttgcaatc ccaaatgggt ttggatgtgc attagggaca      600
ctgcaattga tactatactt catctactgt ggaaacaaag agagaaatc tgcagatgct      660 cagaaagatg agaagtcagt ggagatgaaa gatgatgaga agaagcagaa tgtggttaat      720
ggaaagcaag accttcaagt ttaa                                             744
```

<210> SEQ ID NO 6
<211> LENGTH: 756
<212> TYPE: DNA
<213> ORGANISM: Artificial Sequence
<220> FEATURE:
<223> OTHER INFORMATION: Arabidopsis thaliana SWEET4 (AtSWEET4) codon
      optimized DNA sequences used for SR8D8 expression

<400> SEQUENCE: 6

```
atggttaacg ctacagttgc gagaaacatt gccggcattt gtggaaatgt catctccttg      60
ttcttgttct tatctcccat acctacgttc ataaccatat acaagaagaa aaaggtggag     120
gagtacaaag ctgacccata cttagccacg gttctaaatt gcgcactatg ggtcttttat     180
ggcttaccaa tggttcaacc agatagtctc cttgtgatca ccataaatgg taccggttta     240
gccattgagc tggtgtatct cgctatcttc ttcttctttt ctccaactag tcgcaaggtg     300
aaagtggggc tatggttaat aggagagatg gtgtttgtag aatagtagc cacatgcaca      360 ttgctattgt tccacacaca taaccagaga tcttcttttg ttggaatctt ttgtgtcatt     420
tttgttagtc tcatgtatat tgctcctctc accatcatga gtaaggtgat caagaccaaa     480
agtgtgaagt acatgccatt ctctctctca cttgccaatt tcctcaatgg tgtcgtttgg     540
gttatttatg cacttattaa gttcgacctt ttcattttga ttggaaatgg acttggaacg     600
gtatcaggag cagtacaact tatactctat gcttgctatt acaagacaac accaaaagat     660
gatgaagatg aagaagatga ggagaatctt tctaaggtta actctcagtt acaacttagt     720
ggcaacagtg gacaagctaa acgagtttca gcttga                               756
```

```
<210> SEQ ID NO 7
<211> LENGTH: 777
<212> TYPE: DNA
<213> ORGANISM: Artificial Sequence
<220> FEATURE:
<223> OTHER INFORMATION: Arabidopsis thaliana SWEET7 (AtSWEET7) codon
      optimized DNA sequences used for SR8D8 expression

<400> SEQUENCE: 7
```

```
atggtgtttg cacatttgaa ccttcttcgg aagattgtgg ggattatagg aaacttcatc      60
gctctatgtc tgttcttgtc accaacgcca acatttgttc ggatagtgaa aaagaagtca     120
gtggaggaat attcaccaat accgtattta gcgactctta taaactgttt ggtttgggtt     180
ctttacggac taccaacggt gcatccggac agcacattgg tcattacaat aaacggcaca     240
gggatcttga tcgaaatcgt attccttacg atctttttcg tttattgtgg ccgccaaaaa     300
cagcggttga taatatccgc tgttatagcg gctgaaaccg cgttcatagc tattcttgcg     360
gttttggtat taactctcca acacactacc gaaaaacgta ctatgagtgt tggaatcgta     420
tgttgcgttt tcaacgttat gatgtacgct tctccattgt ctgttatgaa aatggtaata     480
aaaacaaaaa gtgtggagtt catgccgttt tggttatcgg tagctggatt tctaaacgca     540
ggcgtttgga caatttatgc tctcatgcct ttcgacccat tcatggctat accaaatgga     600
attggatgtt tatttgggct agctcaacta atattgtatg gtgcctacta taagtccacc     660
aaaagaataa tggcggaaag agaaaaccaa cctggttacg tcggtttatc aagtgcgatc     720
gctcgtaccg gatctgagaa aaccgcgaat accaaccaag aacctaacaa tgtttaa       777
```

```
<210> SEQ ID NO 8
<211> LENGTH: 1812
<212> TYPE: DNA
<213> ORGANISM: Artificial Sequence
<220> FEATURE:
<223> OTHER INFORMATION: Lipomyces starkeyi LST1_204537 codon optimized
      DNA sequences used for SR8D8 expression

<400> SEQUENCE: 8
```

```
atgggtttcc taggctttct taatcgatct caggcctcag agccagttga aaaggagtca      60
actgcgacca cgccttcaga aggaaggact ccccaacgcc cgctctcacc tgctgtaggt     120
```

```
gtacctctag agcaagactt tgagactcag ctgtctgcga aggatgctcc cttgttggca          180
tttattctgg gtggtgtggc atccgtgggt ggctttatgt ttggatacca aactggtcaa          240
atttcaggtt tccttgagat gagtgatttc aaaactcgtt ttgccgcatg caatagtcaa          300
actggtcaat gtactttcag cgcggcgagg caaggaacca ttgtcggtct cttttcgatt          360
ggtacactta ttggctctct catcgctgcc cccatcgctg atcgcatcgg ccgccgcctg          420
accatctcct tttgggcgtt cttcttcatg attggcactg tcctggagat ttcaagttca          480
catgtatggg tgcagttcgc tatgggccga ttcgttggtg gtctcggtat cggagccctt          540
tcggtagtcg ttcccatgta tcagagtgag agtaccccca ggatgattcg aggcgtcatt          600
gtgagcagct atcaattgat ggtcacactg ggtatttggc tcgcttatat gatcaactgg          660
ggtaccgaaa gtcttcaagg tagccaatcg tggcgtatca ccaacggaat gtcctttctc          720
tgggccctcg tcctcggtat cgctattctc ggtcttccgg agtctcctcg ctatgcctac          780
cgtgtagggc gagaggaaga ggcgcgcaag aacatggctc gcctttacaa gttaagtccg          840
aatcatccca tcattaacct ggagattcaa gagattcaag agaagctcga cgctgaacgg          900
gttggtggcg atcatccttg gtacgaaatc ttcactggtc ctcgcatgct gtaccgcacc          960
atactcggta tggtcttgca ggctggtcaa cagcttactg gtgccaatta cttcttttac         1020
tacggtacca ccgtcttcag cgccacgggt ctctctaact cctatgttac ccagattatc         1080
ttgggttccg ttaacgtagg tggtacgatt gccggccttt ggctcatcga aaactgcggc         1140
cgtcgcaaag cccttatggg tggagcagct tggatgttca tgtgcttcat ggtctttgct         1200
tttgttggtc acttttcctt ggatcatcaa aacccggaag ctactcccca ggctggagcg         1260
gcgctagtcg ttttctcgtg tcttttcatc attgcatttg caatgacatg gggtccaata         1320
gtctgggcca tcgtgggaga gctctacccc gcccgttacc gcgctacctg catgggtctg         1380
gctacatcat ctaactggct cttcaacttc cttatcggat ttttcaccac attcattacg         1440
ggtgatatcg actacctcta cggccttgta tttgccgggt gctgtttcgc tcttttcttc         1500
attgtctatt tcttcgtgat tgagactaag ggccgctccc tcgaggagat tgataccatg         1560
tatgtcctgc atgtcaaccc aatcaacagt gccaagtggg atagctccca gttgatgaga         1620
gatggggatg gactcgtcaa tactgatgac ctgtatctcg aagctggtgg taacaggttc         1680
gccaaggatg agcacagcgc ccatgagatg atcccaagcc atgatgagaa tgcaccgggc         1740
ccgagccaca catcccacgc agatatcgag aaggccgaga gcagcggtgc tgagagccgc         1800
gatgctctct ga                                                            1812
```

```
<210> SEQ ID NO 9
<211> LENGTH: 1737
<212> TYPE: DNA
<213> ORGANISM: Artificial Sequence
<220> FEATURE:
<223> OTHER INFORMATION: RT88 GluT1 co (Protein ID: 11075) codon
      optimized DNA sequences used for SR8D8 expression

<400> SEQUENCE: 9
```

```
atgaatcctg agaatgaatc agttccggcg tcaaaagcga cgactctggc aggtagcgcc           60
gcgcccagca gggcagcttc agtcaagaag gaggcacact ccgcgcccag ctcaaggcca          120
ggttcaactt ccaccccca ggatgaatta gatggagtgc cttcaaagga tcgtgctcca          180
ccattcgttg ttgcactttg cttatttcag agcctggcag ggttactatt tggatgggag          240
caaggtgtga tagcaggact tacaactaat cccgtgtatc aacgtagatt tggggaaccc          300
```

-continued

```
gatcctacga gcgcatcagg gtattctctg ccaagtacga ggcttagctt gataaccggg      360
tttatgtcat tgggtgcgct tttttggggct ttactaattg gacagttgtt acgtagaact     420
ggaataaaaa ttgctatcat cttctccttg gttatctatg cagccggcat cgcgatcgag      480
accagtggtc aatcccagta cggccaggag atagctggaa ggttcgtaac tggttttggt      540
gtggggagtc ttagtctttt agcgcccctg tatcaagctg agtgcagccc taaacaccta      600
agaggattaa ttcatctac ataccagttg atggcgacga tcggcatctt cctatcaaac       660
gcagtgaatt acgcacaaca tgacaagggc actgactttt cctggaggtt ccccatagcc      720
attcagttca tatgggcagc cgtcgtgttc gtggggactg tgttggcacc agaaagtcct      780
agatattacg ttcagagaga caatgtggac agagcaagag taaaccttgc gaaactacgt      840
ggacttgacg aacaggatcc cgaactacta gcagaactgg atgtaatcat caggggggtt      900
gaggatgaga agcttgccgc ggacgcaaca tacctggact gcttcagaat gaaggatagg      960
atgttgctta ggaccatgaa tggtgtgatg gtgcagtggg gacaacaatg gtctggagtc     1020
aatttttttt ttagttacgg taataaattt tttgctacct ctgggatcaa ggatccttac     1080
caaacgcagc taatactttc aggcataaac gttgtcgcaa ctttttcctgg gatccttgcg    1140 gtggatcgtc taggccgtag gacactatta tttattggca gtgctatgat gttcagtggg     1200
caaataatcg ccggaagcgt atccacggcc aagccgaacg atcccgcggc tggtaaggca     1260
ctaatctttg cttcatgttg gttcatcgcc gggtttgctt gcagtggggg accattgggc      1320
tgggtggtag cggcagaaca atttccatta aagatagccc ctctatgcgt ttccttggca     1380
actgcgagta attggcttaa caacttcatt atagcgatca ttgtgcccta tattaccgat     1440
cccggctacg gcaatatagg aaccaaaatt acattcatgt gggccggcac tgagtttctg      1500
gcattcctat acaccttctt ctttattccg gaaacgaagg gtctttcctt ggttcaggtc     1560
gatgaacttt acctgaccgg ggttcccgca tggaggtctg cgagttggac tccgtacggc     1620
ggggcgacag cacgtaatca aaaggataga gacgaagcca agcgtttgaa gcttgggact     1680
gaggcaagcc accatgagaa cgtgcctacc aaaagaaatt tagccgaaga cgtctaa      1737
```

```
<210> SEQ ID NO 10
<211> LENGTH: 1680
<212> TYPE: DNA
<213> ORGANISM: Artificial Sequence
<220> FEATURE:
<223> OTHER INFORMATION: RT88 GluT2 co (Protein ID: 13042) codon
      optimized DNA sequences used for SR8D8 expression

<400> SEQUENCE: 10
```

```
atgtctagca ctccacctgc ccctctactt ggacccgata agccccgtc cacgaggtct        60 aactcatccg gtgagctgga ctttgacaaa cttaacaata aggcaacact aaagcatctg       120
tcccaatcta gacttgaggt cgacgaatca gtagtaagag ctgagggggga ggagaggact      180 acgttctttg tttggtggct tgtcatcgct gcagcgaccg cgcggctatt gtttggctac       240
gacacgggcg tcatcggtgg cgcgcttgtc cacaaggacg ttgcttctga cttgcatcgt       300
gtcccgcttg gttctttcga taaagagtta ctgacatcag ctacaacgct gggggcactg      360
attgccggct ctcatccggg ggtcctagcc gacattattg gcagaaagat tgtcataggt      420
ctggctgatg caatattcat aatcggggct gttcttcagg cagtgagtta tggtgcgaac      480
gcgtactgga ttatggcggt tggccgtcta atcataggct ttggggtggg attagctagt      540
ttggttgtac ctttatatat tggcgagcta agtccaacca gcttaagggg tagattggta      600
```

```
acacttaacg tcgtcgcgat taccggaggg caagtgattg cttattgcct gaaccttgct       660
tttcaaaatg tcacgcacgg gtggcgtttt atggttggtt taggagcaat tcctccggcc       720
ttgcagttac ttatgctgat ttatctaccc gagagtcctc gttttctgct taggcatgac       780
aagttagagg cgactgttac catactgcgt aagatatacc catacgccac tgaagaacag       840
ttacacttaa aagcggatgt aatttctaaa agtgtaaagg agaacatggg tcatagggca       900
acattcgtcc aaacttggaa aagattgcac ctgaatggac ctaactttcg tgcactggtt       960
gtcgcatgtg gattacaggg catccaacaa ctatgcggct tcaacacgtt gatgtattac      1020
gctcctactc ttttccaatc agtaggattt gacaactccc ttgtgatcgg tctggttatt      1080
tccattgtga acctggtttt cacaatcgta gctttgttta ttatcgacag agtggggcgt      1140
aggcgtattg cttgtagcac agtgccgggc atgtgtgggg cgttaatcct agcagccgta      1200
gccttccact tcttaacgat tcataccggg gggaaattgc ctgacaacgg tgcgggcctg      1260
aacgacaagt ggagcccggt cgtacttact gcaatgttgg tctatgtagc tttctacgca      1320
accggtattg ggaacatacc atggcaacag ggggagctat cgagatgga tgtgcgtgga      1380 atgggcaccg ccctatctac tacgtgcaat tggggaggta atttaatcat aggctctact      1440
ttcctgtcct tgattgacag aataaccgcc gcaggtgcgt ttgggttcta cgccggactt      1500
tgctttcttg ggtcaatatt cgtctttttt ttgtaccccg agacaagtgg tctatcactt      1560
gaggagacta gagaggtctt ccttacagga tttgggatta ggaaggccaa taggatgcgt      1620
aaacagaaga tggccgcgct agctcaggtc cgtgatgcag acgacgacgc taccgtctag      1680
```

<210> SEQ ID NO 11
<211> LENGTH: 1521
<212> TYPE: DNA
<213> ORGANISM: Artificial Sequence
<220> FEATURE:
<223> OTHER INFORMATION: RT88 XylT1 co (Protein ID: 10452) codon
      optimized DNA sequences used for SR8D8 expression

<400> SEQUENCE: 11

```
atggtagcgc ccaaaaggtc attattgact aagtttacga ggaatcaata cttggttgga        60
tctcttccaa ccttaggtgg attgattttc ggattggata taagctcaat gtccgctcaa       120
ctgtctaatc catattattt agaaacattc aatcatcctg attctaccct acaaggtttg       180
attaatgctg tcatgcccct tggcagtttc ttcggtgcgt tgtttaatag ttatttgtgt       240
gacttgatcg gtaggaaatg gtgtattata atctcaggat ggttgtgggt gatcggagcc       300
attgtacaga gtacagctaa aaatgtaggt gcgctaatgg ggggtcgtgt cgtggctgga       360
ctggcagtcg gtctggcaag cgcgatcgtg actatctacc aagctgaaat aactaagcct       420
cagttacgtg gaaggatagt ttcagttcaa caactggcca tcatcgttgg aatagcggtg       480
caatacttta tccagtttgg gttcagctac ctagaatctg acaagtcctt tcgtatccct       540
tgggcccttc agcttattcc tggcgccatt cttggttcac tgatgtttat ctttcctgaa       600
tcccccaggt ggctaatgga ccacggaagg gacgatgagg cacttcagat cctagctgac       660
gtgcatgctg cgggtgatac ggaagacgct ctagtccagc tagagttctc tgagataaag       720
aggcaaatag cttttgataa ccaacaaggc gcaaatctt acctagacct acttaaacca       780
gatgtaagat tgcgtgtctt cttgggatgc gccgatcaaa tgtggtcaca gctttccggg       840
atgaacgtga tgatgtatta tgttgtgtat gtttttcagg gtgcggggtt acaaggaaga       900
agggccgagt taatcgcttc aagcgttcaa tacgccttag ctgtcgtttg cacgttaccg       960
```

-continued

```
gctgtaattt ggcttgataa gatcggaagg agacccttat tagtcggtgg tagtgctgcc     1020
atggctacgt gcctaatgat tgtcggcgcc ttacaaaaga ccctggggca taaaatagag     1080
ggcgcagaag ccgctgctac aacgacgtgg gtggtgaccg ggcataaaag cggatcctat     1140
gctattattg tgttttccta ccttttttgtc tgcagttttt ccgcgactct tggtccctgt     1200
tcttggacat acgcctcaga gatcttcccg acgagagtga gaggcaaagc tgtatcattc     1260
gccaccgcct ccaattggat ctttaacttc attcttagta tgactactcc gcccgcattt     1320
cgtaacattc agtaccgtgt gtactttctt tacggtacgt ttaacatatg ctctttttcta     1380 catttctttc ttatgtatcc tgagactaaa ggaaggactt tagaggagat ggaagagata     1440
tttgatggta ctaacacttt caccgcatgg agggtgcctc cggccaaagg cgtcaagaac     1500
gtaactgacc tagaatcctg a                                                1521
```

```
<210> SEQ ID NO 12
<211> LENGTH: 1641
<212> TYPE: DNA
<213> ORGANISM: Artificial Sequence
<220> FEATURE:
<223> OTHER INFORMATION: RT88 XylT2 co (Protein ID: 13731) codon
      optimized DNA sequences used for SR8D8 expression

<400> SEQUENCE: 12
```

```
atggtgaatc tatttgaaag gatagaggac agacccacac ccaaggcagt gtacaactgg      60
cgtgtatacg cttgtgccat cgtcgcggca acagcggcta taatgatagg atacgactcc     120
gcatttatcg gcacaagtat ggcgttagcg tcctttaaga acgaatttgg attggctcac     180
aaaactagta acaatttgc agctatttct gctaatattg tcagcaccta tcaaggggga     240
tgtttctttg ggtctttatt aggatatcct ttaggacaga tcttaggtag gaggctaggt     300
ttatttatct ctgcgttagt ttttgtgctt ggggcaggtg taatgttagc ggccgatggg     360
gctagagggc ttgggccgat atatgggggg agaatagtag cgggtttagg tattggtgcc     420
gctagcaatt taacaccgtt gtacataagc gaaatcgctc ccccggctat tagaggtcag     480
ctggttggaa tgtacgaact tggttggcaa attgggggcc ttgtaggttt ctggattaac     540
tacggcgtaa gcgagaatat accgagctct cataagcagt ggcttattcc ctttgcggtt     600
caactgattc ctggcgcttt atttgctatc ggaataccat tttttgtcag ggaatcccct     660
cgttggttaa taacgagggg taggcgttcc gaggcgctga aaaacctgtg ttatattagg     720
aagttacagc ctgaggacgc ctacattata aacgaaatga atgaaattga cgtgcaagtt     780
gaacacgatc gtactgccgt aggtgaggga ttctgggctc cgttcaggca agtgttcgga     840
aagggctttc tattcaggag aatgctaata actaccagtt tgtttgtgtg gcagaatggt     900
acgggcatca cgccgtcaa ttactacagc ccgaccatct ttaaaagtat aggggtgaca     960
ggaaatacat cattgttaac cacgggcgta ttcggagtaa taaaaactgc ccttgctcta    1020
gtatggtgct tcataataat agatcgtttc ggacgtcgtg ggatcctgtt ggtaggcgct    1080
accggtggtg ctttaagtat gtttgcgatt ggggcgtaca acaagatcca aaacccggca    1140
gcccatccaa cgcctaacct accgccggga gggaaggcgg cgatgttttt tttctatctg    1200
tggactgcct ctacgcagt gtcctggaac ggaacaccgt gggtcgtcaa tcagagtca     1260 tttccgggcg cagttagaca agttacccag tgcttcgcag cgacgtccaa ctggttgtgg    1320
aacttcgtta tctctagggc tacgcctacc atgtttctga atatgggcca ctctggatac    1380
ggagtgtact tatttttcgc tgcgatgcag gtattatcta tcccctatat ctgctttcta    1440
```

-continued

```
ctgcctgaga cgagaaatat cccttagaa gagatggata gactttcgc tcagaggaat      1500 gtatggaatg caaataaaat tgttatggca gagctgcgtc gtgagcatga actgggtgct      1560
aaaaaccccg catatctgaa accgactgcc agccaagaac aaattgagaa cgcaagctct      1620
tcagatggcg agaaagtttg a                                               1641
```

<210> SEQ ID NO 13
<211> LENGTH: 7
<212> TYPE: PRT
<213> ORGANISM: Artificial Sequence
<220> FEATURE:
<223> OTHER INFORMATION: Sequence alignment of SC HXT7 and SC GAL2
      transporters

<400> SEQUENCE: 13

Leu Met Ile Thr Ala Gly Ile
1               5

<210> SEQ ID NO 14
<211> LENGTH: 7
<212> TYPE: PRT
<213> ORGANISM: Artificial Sequence
<220> FEATURE:
<223> OTHER INFORMATION: Sequence alignment of LST1_106361 transporter

<400> SEQUENCE: 14

Phe Ala Ile Thr Ile Gly Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Sequence alignment of LST1_205437 transporter

<400> SEQUENCE: 15

Leu Met Val Thr Leu Gly Ile
1               5

<210> SEQ ID NO 16
<211> LENGTH: 7
<212> TYPE: PRT
<213> ORGANISM: Artificial Sequence
<220> FEATURE:
<223> OTHER INFORMATION: Sequence alighnment of LST1_76

<400> SEQUENCE: 16

Phe Ser Ile Phe Phe Gly Ile
1               5

<210> SEQ ID NO 17
<211> LENGTH: 7
<212> TYPE: PRT
<213> ORGANISM: Artificial Sequence
<220> FEATURE:
<223> OTHER INFORMATION: Sequence alignment of LST1_4224 transporter

<400> SEQUENCE: 17

Phe Cys Ile Val Val Gly Ile
1               5

<210> SEQ ID NO 18
<211> LENGTH: 7
<212> TYPE: PRT
<213> ORGANISM: Artificial Sequence

```
<220> FEATURE:
<223> OTHER INFORMATION: Sequence alignment of RT04_11075 transporter

<400> SEQUENCE: 18

Leu Met Ala Thr Ile Gly Ile
1               5

<210> SEQ ID NO 19
<211> LENGTH: 7
<212> TYPE: PRT
<213> ORGANISM: Artificial Sequence
<220> FEATURE:
<223> OTHER INFORMATION: Sequence alignment of RT04_13042 transporter

<400> SEQUENCE: 19

Val Ala Ile Thr Gly Gly Gln
1               5

<210> SEQ ID NO 20
<211> LENGTH: 7
<212> TYPE: PRT
<213> ORGANISM: Artificial Sequence
<220> FEATURE:
<223> OTHER INFORMATION: Sequence alignment of RT04_13731 transporter

<400> SEQUENCE: 20

Leu Gly Trp Gln Ile Gly Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Sequence alignment of RT04_10452 transporter

<400> SEQUENCE: 21

Leu Ala Ile Ile Val Gly Ile
1               5

<210> SEQ ID NO 22
<211> LENGTH: 7
<212> TYPE: PRT
<213> ORGANISM: Artificial Sequence
<220> FEATURE:
<223> OTHER INFORMATION: Sequence alignment of SC HXT7 and SC GAL2
      transporters

<400> SEQUENCE: 22

Gly Ile Val Asn Phe Ala Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Sequence alignment of LST1_106361 transporter

<400> SEQUENCE: 23

Asn Ile Val Asn Val Val Phe
1               5

<210> SEQ ID NO 24
<211> LENGTH: 7
<212> TYPE: PRT
<213> ORGANISM: Artificial Sequence
```

```
<220> FEATURE:
<223> OTHER INFORMATION: Sequence alignment of LST1_205437 transporter

<400> SEQUENCE: 24

Gly Ser Val Asn Val Gly Gly
1               5

<210> SEQ ID NO 25
<211> LENGTH: 7
<212> TYPE: PRT
<213> ORGANISM: Artificial Sequence
<220> FEATURE:
<223> OTHER INFORMATION: Sequence alignment of LST1_76 transporter

<400> SEQUENCE: 25

Gly Ile Val Lys Thr Val Phe
1               5

<210> SEQ ID NO 26
<211> LENGTH: 7
<212> TYPE: PRT
<213> ORGANISM: Artificial Sequence
<220> FEATURE:
<223> OTHER INFORMATION: Sequence alignment of LST1_4224 transporter

<400> SEQUENCE: 26

Asn Ile Thr Gln Leu Ile Gly
1               5

<210> SEQ ID NO 27
<211> LENGTH: 7
<212> TYPE: PRT
<213> ORGANISM: Artificial Sequence
<220> FEATURE:
<223> OTHER INFORMATION: Sequence alignment of RT04_11075 transporter

<400> SEQUENCE: 27

Ser Gly Ile Asn Val Val Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Sequence alignment of RT04_13042 transporter

<400> SEQUENCE: 28

Ser Ile Val Asn Leu Val Phe
1               5

<210> SEQ ID NO 29
<211> LENGTH: 7
<212> TYPE: PRT
<213> ORGANISM: Artificial Sequence
<220> FEATURE:
<223> OTHER INFORMATION: Sequence alignment of RT04_13731 transporter

<400> SEQUENCE: 29

Gly Val Ile Lys Thr Ala Leu
1               5

<210> SEQ ID NO 30
<211> LENGTH: 7
<212> TYPE: PRT
<213> ORGANISM: Artificial Sequence
<220> FEATURE:
```

<223> OTHER INFORMATION: Sequence alignment of RT04_10452 transporter

<400> SEQUENCE: 30

Tyr Ala Leu Ala Val Val Cys
1               5

<210> SEQ ID NO 31
<211> LENGTH: 491
<212> TYPE: PRT
<213> ORGANISM: Artificial Sequence
<220> FEATURE:
<223> OTHER INFORMATION: protein sequence alignmnet of XylE

<400> SEQUENCE: 31

Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
            20                  25                  30

Gly Thr Val Glu Ser Leu Asn Thr Val Phe Val Ala Pro Gln Asn Leu
        35                  40                  45

Ser Glu Ser Ala Ala Asn Ser Leu Leu Gly Phe Cys Val Ala Ser Ala
        50                  55                  60

Leu Ile Gly Cys Ile Ile Gly Gly Ala Leu Gly Gly Tyr Cys Ser Asn
65                  70                  75                  80

Arg Phe Gly Arg Arg Asp Ser Leu Lys Ile Ala Ala Val Leu Phe Phe
                85                  90                  95

Ile Ser Gly Val Gly Ser Ala Trp Pro Glu Leu Gly Phe Thr Ser Ile
                100                 105                 110

Asn Pro Asp Asn Thr Val Pro Val Tyr Leu Ala Gly Tyr Val Pro Glu
            115                 120                 125

Phe Val Ile Tyr Arg Ile Ile Gly Gly Ile Gly Val Gly Leu Ala Ser
        130                 135                 140

Met Leu Ser Pro Met Tyr Ile Ala Glu Leu Ala Pro Ala His Ile Arg
145                 150                 155                 160

Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Ser
                180                 185                 190

Trp Leu Asn Thr Asp Gly Trp Arg Tyr Met Phe Ala Ser Glu Cys Ile
                195                 200                 205

Pro Ala Leu Leu Phe Leu Met Leu Leu Tyr Thr Val Pro Glu Ser Pro
            210                 215                 220

Arg Trp Leu Met Ser Arg Gly Lys Gln Glu Gln Ala Glu Gly Ile Leu
225                 230                 235                 240

Arg Lys Ile Met Gly Asn Thr Leu Ala Thr Gln Ala Val Gln Glu Ile
                245                 250                 255

Lys His Ser Leu Asp His Gly Arg Lys Thr Gly Gly Arg Leu Leu Met
                260                 265                 270

Phe Gly Val Gly Val Ile Val Ile Gly Val Met Leu Ser Ile Phe Gln
            275                 280                 285

Gln Phe Val Gly Ile Asn Val Val Leu Tyr Tyr Ala Pro Glu Val Phe
        290                 295                 300

Lys Thr Leu Gly Ala Ser Thr Asp Ile Ala Leu Leu Gln Thr Ile Ile
305                 310                 315                 320

Val Gly Val Ile Asn Leu Thr Phe Thr Val Leu Ala Ile Met Thr Val
            325                 330                 335

-continued

```
Asp Lys Phe Gly Arg Lys Pro Leu Gln Ile Ile Gly Ala Leu Gly Met
        340                 345                 350

Ala Ile Gly Met Phe Ser Leu Gly Thr Ala Phe Tyr Thr Gln Ala Pro
        355                 360                 365

Gly Ile Val Ala Leu Leu Ser Met Leu Phe Tyr Val Ala Ala Phe Ala
        370                 375                 380

Met Ser Trp Gly Pro Val Cys Trp Val Leu Leu Ser Glu Ile Phe Pro
385                 390                 395                 400

Asn Ala Ile Arg Gly Lys Ala Leu Ala Ile Ala Val Ala Ala Gln Trp
                405                 410                 415

Leu Ala Asn Tyr Phe Val Ser Trp Thr Phe Pro Met Met Asp Lys Asn
        420                 425                 430

Ser Trp Leu Val Ala His Phe His Asn Gly Phe Ser Tyr Trp Ile Tyr
        435                 440                 445

Gly Cys Met Gly Val Leu Ala Ala Leu Phe Met Trp Lys Phe Val Pro
        450                 455                 460

Glu Thr Lys Gly Lys Thr Leu Glu Glu Leu Glu Ala Leu Trp Glu Pro
465                 470                 475                 480

Glu Thr Lys Lys Thr Gln Gln Thr Ala Thr Leu
                485                 490
```

```
<210> SEQ ID NO 32
<211> LENGTH: 574
<212> TYPE: PRT
<213> ORGANISM: Artificial Sequence
<220> FEATURE:
<223> OTHER INFORMATION: protein sequence alignmnet of ScGal2

<400> SEQUENCE: 32

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Ser Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
        130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205
```

-continued

```
Thr Leu Val Ser Cys Tyr Gln Leu Met Ile Thr Ala Gly Ile Phe Leu
    210             215             220

Gly Tyr Cys Thr Asn Tyr Gly Thr Lys Ser Tyr Ser Asn Ser Val Gln
225             230             235                 240

Trp Arg Val Pro Leu Gly Leu Cys Phe Ala Trp Ser Leu Phe Met Ile
            245             250             255

Gly Ala Leu Thr Leu Val Pro Glu Ser Pro Arg Tyr Leu Cys Glu Val
            260             265             270

Asn Lys Val Glu Asp Ala Lys Arg Ser Ile Ala Lys Ser Asn Lys Val
        275             280             285

Ser Pro Glu Asp Pro Ala Val Gln Ala Glu Leu Asp Leu Ile Met Ala
    290             295             300

Gly Ile Glu Ala Glu Lys Leu Ala Gly Asn Ala Ser Trp Gly Glu Leu
305             310             315                 320

Phe Ser Thr Lys Thr Lys Val Phe Gln Arg Leu Leu Met Gly Val Phe
            325             330             335

Val Gln Met Phe Gln Gln Leu Thr Gly Asn Asn Tyr Phe Phe Tyr Tyr
            340             345             350

Gly Thr Val Ile Phe Lys Ser Val Gly Leu Asp Asp Ser Phe Glu Thr
            355             360             365

Ser Ile Val Ile Gly Val Val Asn Phe Ala Ser Thr Phe Phe Ser Leu
    370             375             380

Trp Thr Val Glu Asn Leu Gly His Arg Lys Cys Leu Leu Leu Gly Ala
385             390             395                 400

Ala Thr Met Met Ala Cys Met Val Ile Tyr Ala Ser Val Gly Val Thr
            405             410             415

Arg Leu Tyr Pro His Gly Lys Ser Gln Pro Ser Ser Lys Gly Ala Gly
            420             425             430

Asn Cys Met Ile Val Phe Thr Cys Phe Tyr Ile Phe Cys Tyr Ala Thr
            435             440             445

Thr Trp Ala Pro Val Ala Trp Val Ile Thr Ala Glu Ser Phe Pro Leu
    450             455             460

Arg Val Lys Ser Lys Cys Met Ala Leu Ala Ser Ala Ser Asn Trp Val
465             470             475                 480

Trp Gly Phe Leu Ile Ala Phe Phe Thr Pro Phe Ile Thr Ser Ala Ile
            485             490             495

Asn Phe Tyr Tyr Gly Tyr Val Phe Met Gly Cys Leu Val Ala Met Phe
            500             505             510

Phe Tyr Val Phe Phe Phe Val Pro Glu Thr Lys Gly Leu Ser Leu Glu
            515             520             525

Glu Ile Gln Glu Leu Trp Glu Glu Gly Val Leu Pro Trp Lys Ser Glu
    530             535             540

Gly Trp Ile Pro Ser Ser Arg Arg Gly Asn Asn Tyr Asp Leu Glu Asp
545             550             555                 560

Leu Gln His Asp Asp Lys Pro Trp Tyr Lys Ala Met Leu Glu
            565             570
```

PLANT SWEET AND YEAST MSF TRANSPORTER CAPABLE OF TRANSPORTING DIFFERENT SUGARS SIMULTANEOUSLY

PRIORITY

This application is a 371 of International Application No. PCT/US2021/026548, filed Apr. 9, 2021, which claims the benefit of U.S. Ser. No. 63/008,263, filed Apr. 10, 2020, which are incorporated by reference herein in their entireties

STATEMENT REGARDING FEDERALLY SPONSORED RESEARCH AND DEVELOPMENT

This invention was made with government support under Grant DE-S00018420 awarded by the Department of Energy. The Government has certain rights in the invention.

SEQUENCE LISTING

The instant application contains a Sequence Listing which has been submitted in TXT file format and is hereby incorporated by reference in its entirety. Said TXT copy, created on Apr. 10, 2020, is named 428262-000090-Sequence_Listing_ST25.txt and is 41,144 bytes in size.

BACKGROUND

Second generation biofuel/bioproducts production requires utilization of sustainable carbon source in the form of abundant plant biomass. The process of depolymerization of plant biomass releases various hexose and pentose (mainly glucose and xylose), which can be further converted into valuable product via microbial fermentation. Because microorganisms utilize glucose preferentially (due to glucose repression), at the end of glucose fermentation, xylose and other sugar fermentation capacity is reduced due to accumulation of byproduct/product of interest or/and microorganism's requirement to adapt to new carbon source. As a result, the utilization of sugar in mixed sugar fermentation is sequential and occurs only after glucose depletion.

Efficient production of biofuels/bioproducts from lignocellulos biomass requires the simultaneous utilization of all sugars present in the raw material, including hexoses (such as glucose) and pentoses (such as xylose). Lignocellulose biomass, depending on the plant source, consists of approximately 70% glucose and 30% xylose, with pentoses being produced via the acid pretreatment of hemicellulose, which releases xylose and arabinose. Both non-conventional yeast and engineered *Saccharomyces cerevisiae* can be used to convert hexose and pentose into value added product. However, xylose metabolism is not native to *S. cerevisiae*, which is subjected to glucose catabolite repression. The glucose repression reduces the productivity of fermentation processes. Due to the glucose repression phenomena, yeast ferments glucose first, and then xylose, leading to prolonged mixed sugar fermentation. The development of efficient and economically relevant processes requires microorganisms capable of simultaneously consuming both glucose and xylose for the conversion of plant biomass into different chemicals and bioproducts.

Besides having efficient intracellular xylose utilization, the transport of xylose remains a limiting step to further improve fermentation performance of recombinant *S. cerevisiae* since *S. cerevisiae* does not have dedicated xylose transporters, and relies on numerous hexose transporters (HXT1-17 and GAL2) for xylose transport. Although native transport is enough to enable xylose fermentation, the presence of glucose completely inhibits xylose uptake due to the high affinity of the native transporters toward glucose. Strategies are needed in the art that allow for the co-fermentation of monomer sugars present in, for example, hydrolysate.

SUMMARY

Provided herein are SWEET and LST1_205437 transporters and variants that simultaneously transport two or more different types of sugar across the cell membrane. SWEET and LST1_205437 transporters and variants thereof have no or reduced glucose repression, which enables the co-utilization of multiple sugars in the presence of glucose, and specifically enables the co-fermentation of sugars found in, for example, lignocellulose hydrolysates, such as xylose and glucose.

An embodiment provides a recombinant yeast comprising one or more heterologous polynucleotides encoding an *Arabidopsis thaliana* SWEET1 (AtSWEET1), *Arabidopsis thaliana* SWEET4 (AtSWEET4), *Arabidopsis thaliana* SWEET5 (AtSWEET5), or *Arabidopsis thaliana* SWEET7 (AtSWEET7) transporter polypeptide or a *Lipomyces starkeyi* LST1 transporter polypeptide, a mutant thereof, an homolog thereof, or combinations thereof.

The yeast can lack expression of endogenous hexose transporters HXT1-7 and endogenous Gal2 transporter. The yeast can be selected from *Saccharomyceraceae* sp., *Saccharomyces cerevisiae*, *Saccharomyces pastorianus*, *Saccharomyces beticus*, *Saccharomyces fermentati*, *Saccharomyces paradoxus*, *Saccharomyces uvarum Saccharomyces bay anus*; *Schizosaccharomyces* sp., *Schizosaccharomyces pombe*, *Schizosaccharomyces japonicus*, *Schizosaccharomyces octosporus*, *Schizosaccharomyces cryophilus*, *Torulaspora* sp., *Torulaspora delbrueckii*, *Kluyveromyces* sp., *Kluyveromyces marxianus*, *Pichia* sp., *Pichia stipitis*, *Pichia pastoris*, *Pichia angusta*, *Zygosaccharomyces* sp., *Zygosaccharomyces bailii*, *Brettanomyces* sp., *Brettanomyces inter medius*, *Brettanomyces bruxellensis*, *Brettanomyces anomalus*, *Brettanomyces custersianus*, *Brettanomyces naardenensis*, *Brettanomyces nanus*, *Dekkera bruxellensis*, *Dekkera anomala*; *Metschnkowia* sp., *Issatchenkia* sp., *Issatchenkia orientalis*, *Kloeckera* sp. *Kloeckera apiculate*, *Aureobasidium* sp., *Aureobasidium pullulans*, and *Corynebacterium glutamicum*. The AtSWEET transporter or the LST1 transporter further can comprise an amino acid substitution. The *Lipomyces starkeyi* LST1_204537 transporter polypeptide can have an amino acid substitution at position 365, wherein the Asn (Asn365) can be substituted with an amino acid with a polar neutral side chain, an amino acid with an aliphatic side chain, or an amino acid with a hydrophobic side chain. The amino acid substitution can be an Asn365Ser substitution, where the Asn365 is substituted with a Ser amino acid; or an Ans365Val substitution, where the Asn365 is substituted with a Val amino acid.

The AtSWEET1 transporter polypeptide can have an amino acid substitution at position 168, wherein the Phe amino acid (Phe168) can be substituted with an Ala amino acid (Phe168Ala substitution). The AtSWEET7 transporter polypeptide can have an amino acid substitution at position 145 or 175, wherein the Asn amino acid at position 145 (Asn165) can substituted with a Ser amino acid (Asn145Ser substitution), or the Ala amino acid at position 175 (Ala175) can be substituted with a Phe amino acid (Ala175Phe substitution). A AtSWEET7 transporter polypeptide can have two amino acid substitutions, an Asn145Ser substitution and an Ala175Phe substitution.

The recombinant yeast can further comprise a heterologous polynucleotide encoding a putative glucose transporter. The putative glucose transporter can be RT04_11075, RT04_13042, RT04_13731 or RT04_10452 (see Table 3). The recombinant yeast can further comprise a heterologous polynucleotide encoding a RT04_13731 or RT04_10452 putative xylose transporter.

The yeast can have improved sugar co-utilization of two or more different sugars as compared to a control yeast. The two or more different sugars can be selected from glucose, galactose, lactose, arabinose, mannose, sucrose, fructose, xylobiose, cellobiose, xylose, rhamnose, 4-deoxy-L-erythro-5-hexoseulose uronate, maltose, cellodextrins, and combinations thereof. For the two or more different sugars, a first sugar can be glucose and a second sugar can be selected from galactose, lactose, arabinose, mannose, sucrose, fructose, xylobiose, cellobiose, xylose, rhamnose, 4-deoxy-L-erythro-5-hexoseulose uronate, maltose, cellodextrins, and combinations thereof.

Yet another embodiment provides a method for co-utilization of two or more different sugars in a fermentation reaction comprising contacting a recombinant yeast comprising a heterologous polynucleotide encoding an *Arabidopsis thaliana* SWEET1 transporter polypeptide (AtSWEET1), an *Arabidopsis thaliana* SWEET4 transporter polypeptide (AtSWEET4), an *Arabidopsis thaliana* SWEET5 transporter polypeptide (AtSWEET5), an *Arabidopsis thaliana* SWEET7 transporter polypeptide (AtSWEET7) transporter polypeptide, a *Lipomyces starkeyi* LST1 transporter polypeptide, a mutant thereof, a homolog thereof, or combinations thereof with the two or more different sugars under fermentation conditions such that the two or more different sugars are co-utilized at an improved rate as compared to a control yeast. The two or more different sugars can be selected from glucose, galactose, lactose, arabinose, mannose, sucrose, fructose, xylobiose, cellobiose, xylose, rhamnose, 4-deoxy-L-erythro-5-hexoseulose uronate, maltose, cellodextrins and combinations thereof. For the two or more different sugars, a first sugar can be glucose and a second sugar can be selected from galactose, lactose, arabinose, mannose, sucrose, fructose, xylobiose, cellobiose, xylose, rhamnose, 4-deoxy-L-erythro-5-hexoseulose uronate, maltose, cellodextrins, and combinations thereof.

Another embodiment provides a method for co-utilization of two or more different sugars in a fermentation reaction comprising contacting two or more different sugars with one or more of an *Arabidopsis thaliana* SWEET1 transporter polypeptide (AtSWEET1), an *Arabidopsis thaliana* SWEET4 transporter polypeptide (AtSWEET4), an *Arabidopsis thaliana* SWEET5 transporter polypeptide (AtSWEET5), an *Arabidopsis thaliana* SWEET7 transporter polypeptide (AtSWEET7) transporter polypeptide, a *Lipomyces starkeyi* LST1 transporter polypeptide, a mutant thereof, a homolog thereof, or combinations thereof. The two or more different sugars can be present in a lignocellulosic biomass. The AtSWEET1, AtSWEET4, AtSWEET5, or AtSWEET7 transporter polypeptide, the *Lipomyces starkeyi* LST1_204537 transporter polypeptide, the mutant thereof, or the homolog thereof can be encoded by an heterologous polynucleotide expressed in a recombinant yeast. The lignocellulosic biomass can be at least partially fermented into a biofuel. The two or more different sugars can be selected from glucose, galactose, lactose, arabinose, mannose, sucrose, fructose, xylobiose, cellobiose, xylose, rhamnose, 4-deoxy-L-erythro-5-hexoseulose uronate, maltose, cellodextrins and combinations thereof. For the two or more different sugars, a first sugar can be glucose and a second sugar can be selected from galactose, lactose, arabinose, mannose, sucrose, fructose, xylobiose, cellobiose, xylose, rhamnose, 4-deoxy-L-erythro-5-hexoseulose uronate, maltose, cellodextrins, and combinations thereof.

The mixtures of sugars can comprise lignocellulosic biomass. The lignocellulosic biomass can comprise glucose, xylose, galactose, fructose, sucrose, xylodextrin, cellobiose, arabinose, mannose, lactose, or combinations thereof.

Another embodiment provides a method of producing ethanol comprising contacting a recombinant yeast comprising a heterologous polynucleotide encoding an *Arabidopsis thaliana* SWEET1 (AtSWEET1), *Arabidopsis thaliana* SWEET4 (AtSWEET4), *Arabidopsis thaliana* SWEET5 (AtSWEET5), or *Arabidopsis thaliana* SWEET7 (AtSWEET7) transporter polypeptide or a *Lipomyces starkeyi* LST1 transporter polypeptide, a mutant thereof, a homolog thereof, or combinations thereof with two or more different sugars under conditions such that the two or more different sugars are co-utilized and ethanol is produced.

The two or more different sugars can be present in a lignocellulosic biomass. The lignocellulosic biomass can comprise glucose, xylose, galactose, fructose, sucrose, xylodextrin, cellobiose, arabinose, mannose, lactose, or combinations thereof.

Yet another embodiment provides a bioreactor for the continuous conversion of lignocellulose biomass into biofuel comprising a recombinant yeast comprising an *Arabidopsis thaliana* SWEET1 (AtSWEET1), AtSWEET4, AtSWEET5, or AtSWEET7 transporter polypeptide, a *Lipomyces starkeyi* LST1 transporter polypeptide, a mutant thereof, a homolog thereof, or combinations thereof.

Therefore, provided herein are compositions and methods that allow for the bypass of glucose repression by exploiting alternative sugar transporters having the capacity to co-transport both glucose and other sugar simultaneously.

BRIEF DESCRIPTION OF THE DRAWINGS

The features, objects and advantages other than those set forth above will become more readily apparent when consideration is given to the detailed description below. Such detailed description makes reference to the following drawings, wherein:

FIG. 3A illustrates growth characteristics of SR8D8 expressing transporters summarized using PCA chart. X axis is growth measurement on glucose and Y axis is growth measurement on xylose based on OD600. The mean OD600 from two biological replicates of each transporters after 40 hrs are illustrated using PCA chart. FIG. 3B illustrates representative growth curves generated by Bioscreen C.

FIG. 4A illustrates the sequential fermentation of 20 g/L of glucose and xylose mixed by SR8D8 expressing ScGal2. FIG. 4B illustrates the partial co-fermentation of 20 g/L of glucose and xylose mixed by SR8D8 expressing LST1_205437. FIG. 4C illustrates the true co-fermentation of 20 g/L of glucose and xylose mixed by SR8D8 expressing. Symbols: glucose (square), xylose (triangle up), DCW (circle), ethanol (triangle down), glycerol (diamond). FIG. 4D illustrates the inhibitory effect of 0 mM, 25 mM and 100 mM glucose on xylose transport in SR8D8 expressing ScGal2. FIG. 4E illustrates the inhibitory effect of 0 mM, 25 mM and 100 mM glucose on xylose transport in SR8D8 expressing LST1_205437. FIG. 4F illustrates the inhibitory effect of 0 mM, 25 mM and 100 mM glucose on xylose transport in SR8D8 expressing AtSWEET7. Global curve fitting for Michaelis-Menten kinetics with competitive inhibition was applied to data of three independent measurements at each concentration.

FIG. 5A illustrates the solo glucose fermentation of 20 g/L of glucose and xylose mixed sugar in YP medium of AtSWEET1. FIG. 5B illustrates the co-fermentation with glucose preference of 20 g/L of glucose and xylose mixed sugar in YP medium of AtSWEET4. Symbols: glucose (square), xylose (triangle up), DCW (circle), ethanol (triangle down), glycerol (diamond).

FIG. 7G illustrates sugar uptake kinetics by SR8D8 expressing AtSWEET1. FIG. 7H illustrates sugar uptake kinetics by SR8D8 expressing ScGal2. FIG. 7I illustrates sugar uptake kinetics by SR8D8 expressing AtSWEET7. FIG. 7J illustrates sugar uptake kinetics by SR8D8 expressing LST1_205437. Initial glucose uptake (5 s) was measured at 30° C. over a concentration range of 0.2 to 100 mM glucose. Curve fitting for Michaelis-Menten kinetics was applied to data of three independent measurements at each concentration.

FIG. 9A illustrates the predicted binding orientation of D-glucose in LST1 in OF conformation. FIG. 9B illustrates the predicted binding orientation of D-glucose in ScGal2 in OF conformation. FIG. 9C illustrates the predicted binding orientation of D-xylose in LST1 in OF conformation. FIG. 9D illustrates the predicted binding orientation of D-xylose in ScGal2 in OF conformation.

FIG. 10 illustrates glucose dockpose of ScGal2 and LST1_205437 overplayed with glucose bound structure of XylE. Residues around 5 Å of the binding site of XylE, LST1_205437 and ScGal2 are represented in salmon, green and cyan, respectively.

FIG. 11A illustrates glucose and xylose mixed sugar fermentation profile of SR8D8 expressing LST1_205437 (wild type). FIG. 11B illustrates glucose and xylose mixed sugar fermentation profile of SR8D8 expressing LST1_205437 Ala335Asn mutant. 20 g/L of glucose and xylose mixed sugar fermentation in YP medium. Symbols: glucose (square), xylose (triangle up), DCW (circle), ethanol (triangle down), glycerol (diamond).

FIG. 16A illustrates glucose and xylose mixed sugar fermentation profile of SR8D8 expressing SWEET1 (wild type). FIG. 16B illustrates glucose and xylose mixed sugar fermentation profile of SR8D8 expressing SWEET7 (wild type). FIG. 16C illustrates glucose and xylose mixed sugar fermentation profile of SR8D8 expressing SWEET1 Phe168Ala. FIG. 16D illustrates glucose and xylose mixed sugar fermentation profile of SR8D8 expressing SWEET7 Trp58Ser. The 20 g/L of glucose and xylose mixed sugar fermentation was done in YP medium. Symbols: glucose (square), xylose (triangle up), DCW (circle), ethanol (triangle down), glycerol (diamond).

FIG. 21A shows 70 g/L of glucose and 40 g/L xylose mixed sugar fermentation by SR8D8 expressing ScGal2. FIG. 21B shows 70 g/L of glucose and 40 g/L xylose mixed sugar fermentation by SR8D8 expressing LST1_205437. FIG. 21C shows 70 g/L of glucose and 40 g/L xylose mixed sugar fermentation by SR8D8 expressing AtSWEET7. Symbols: glucose (square), xylose (triangle up), DCW (circle).

DETAILED DESCRIPTION

Figure 1:
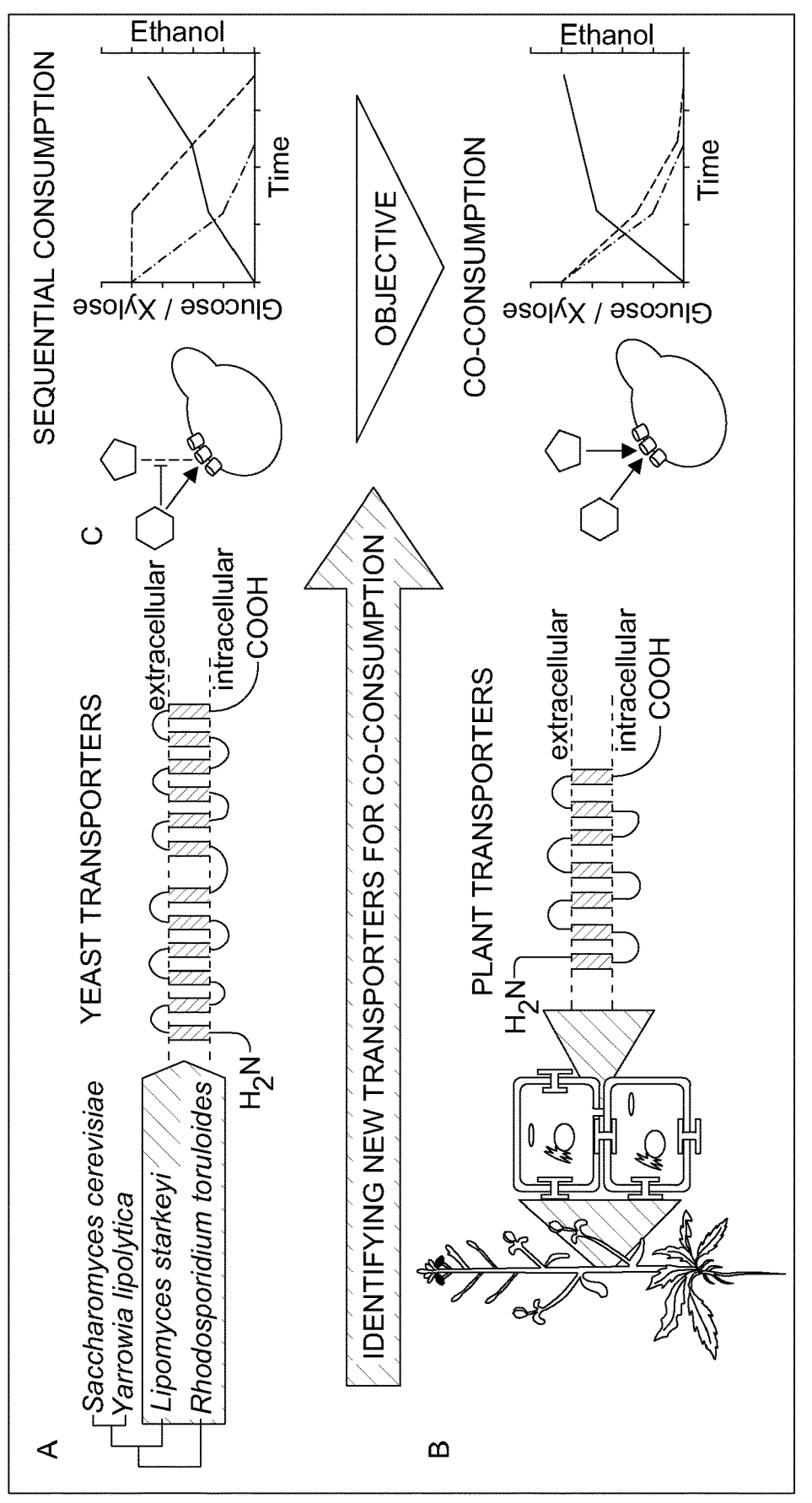
FIG. 1 illustrates the bioprospecting strategy implemented, as the main steps applied to identify novel xylose and glucose co-transporting transporters. Transporters from emerging oleaginous yeasts *Lipomyces starkeyi* and *Rhodosporidium toruloides* were identified (A) and SWEET transporters from *Arabidopsis thaliana* were characterized (B). The fermentation profile of a sugar mixture containing glucose and xylose by the engineered *S. cerevisiae* is generally, where glucose presence inhibits xylose transport leading to sequential sugar utilization; while the application of the transporters described herein provide for relief of glucose inhibition of xylose transport, leading to glucose and xylose co-consumption (C).

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

Likewise, many modifications and other embodiments of the genetically modified microorganisms and methods described herein will come to mind to one of skill in the art having the benefit of the teachings presented in the foregoing descriptions and the associated drawings. Therefore, it is to be understood that the methods and compositions are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art.

Overview

For the efficient conversion of lignocellulosic biomass into fuels and bioproducts with value added, *S. cerevisiae* must simultaneously co-utilize glucose and xylose. There is no efficient yeast engineered for the simultaneous consumption of both glucose and xylose. The main obstacle to achieving an efficient glucose and xylose cotransport is a high affinity of yeast hexose transporters toward glucose. Extended bioprospecting methods were used to identify novel transporters from oleaginous yeast and plants. *L. starkeyi* LST1_205437 transporter was identified and characterized as a partial glucose and xylose co-transporter. By expanding bioprospecting beyond the kingdom of fungi and typical 12 transmembrane transporter, SWEET family transporters were also identified and evaluated to investigate glucose and xylose co-fermentation in yeast. Valuable information about the new family of transporters was discovered, especially in the use of *A. thaliana* SWEET transporters in glucose or/and xylose fermentation.

The present disclosure provides novel strategies for the co-utilization of two of more sugars in fermentation reactions. The compositions and methods are useful in, for example, the efficient production of biofuels. Specifically, for bioethanol production, instead of using engineered *S. cerevisiae* that are subject to glucose inhibition, recombinant microorganisms, for example, yeast, comprising recombinant sugar transporters identified in oleaginous yeast and in plants (i.e., in *L. starkeyi* and in *A. thaliana*, respectively) are used to generate microorganisms capable of co-fermenting glucose and xylose simultaneously, thereby enabling the continuous efficient production of, for example, bioethanol.

Compositions and methods are described that can enable economic production of biofuel, such as bioethanol, which can be used as fossil fuel replacement. The improved efficiency of fermentation of primarily lignocellulosic feedstocks decreases fermentation time and increases product yield and productivity. The resulting bioethanol produced from biomass is a renewable source of liquid transportation fuels that can be distributed and used through existing transportation-fuel infrastructure.

Large-scale production is feasible because the methods rely on engineered microorganisms, which allows the use of inexpensive lignocellulosic biomasses as substrates. Furthermore, the bioengineering of fermenting yeast such as *S. cerevisiae* to express the presently disclosed sugar transporters efficiently switches sugar consumption from sequential to concurrent (FIG. 1), while allowing for continuous and efficient bioethanol production as long as sugars are present in the substrate, and eliminating the loss of production induced by glucose inhibition and bioproduct accumulation.

Recombinant Microorganisms

A recombinant, transgenic, or genetically engineered microorganism is a microorganism, e.g., fungus, or yeast that has been genetically modified from its native state. Thus, a "recombinant yeast" or "recombinant yeast cell" refers to a yeast cell that has been genetically modified from the native state. A recombinant yeast cell can have, for example, nucleotide insertions, nucleotide deletions, nucleotide rearrangements, gene disruptions, recombinant polynucleotides, heterologous polynucleotides, deleted polynucleotides, nucleotide modifications, or combinations thereof introduced into its DNA. These genetic modifications can be present in the chromosome of the yeast or yeast cell, or on a plasmid in the yeast or yeast cell. Recombinant cells disclosed herein can comprise exogenous polynucleotides on plasmids. Alternatively, recombinant cells can comprise exogenous polynucleotides stably incorporated into their chromosome.

A heterologous or exogenous polypeptide or polynucleotide refers to any polynucleotide or polypeptide that does not naturally occur or that is not present in the starting target microorganism. For example, a polynucleotide from bacteria that is transformed into a yeast cell that does naturally or otherwise comprise the bacterial polynucleotide is a heterologous or exogenous polynucleotide. A heterologous or exogenous polypeptide or polynucleotide can be a wild-type, synthetic, or mutated polypeptide or polynucleotide. In an embodiment, a heterologous or exogenous polypeptide or polynucleotide is not naturally present in a starting target microorganism and is from a different genus or species than the starting target microorganism.

A homologous or endogenous polypeptide or polynucleotide refers to any polynucleotide or polypeptide that naturally occurs or that is otherwise present in a starting target microorganism. For example, a polynucleotide that is naturally present in a yeast cell is a homologous or endogenous polynucleotide. In an embodiment, a homologous or endogenous polypeptide or polynucleotide is naturally present in a starting target microorganism.

A recombinant microorganism can comprise one or more polynucleotides not present in a corresponding wild-type cell, wherein the polynucleotides have been introduced into that microorganism using recombinant DNA techniques, or which polynucleotides are not present in a wild-type microorganism and is the result of one or more mutations.

A genetically modified or recombinant microorganism can be, for example, a yeast (i.e., Ascomycota and Basidiomycota). Examples include *Saccharomyceraceae*, such as *Saccharomyces cerevisiae*, *Saccharomyces cerevisiae* strain S8, *Saccharomyces pastorianus*, *Saccharomyces beticus*, *Saccharomyces fermentati*, *Saccharomyces paradoxus*, *Saccharomyces uvarum* and *Saccharomyces bayanus*; *Schizo-*

*saccharomyces* such as *Schizosaccharomyces pombe, Schizosaccharomyces japonicus, Schizosaccharomyces octosporus* and *Schizosaccharomyces cryophilus; Torulaspora* such as *Torulaspora delbrueckii; Kluyveromyces* such as *Kluyveromyces marxianus; Pichia* such as *Pichia stipitis, Pichia pastoris* or *Pichia angusta, Zygosaccharomyces* such as *Zygosaccharomyces bailii; Brettanomyces* such as *Brettanomyces inter medius, Brettanomyces bruxellensis, Brettanomyces anomalus, Brettanomyces custersianus, Brettanomyces naardenensis, Brettanomyces nanus, Dekkera bruxellensis* and *Dekkera anomala; Metschmkowia, Issatchenkia,* such as *Issatchenkia orientalis, Kloeckera* such as *Kloeckera apiculata; Aureobasidium* such as *Aureobasidium pullulans.* Other examples of fungi can include *Trichoderma reesei, Aspergillus niger, Chrysosporium lucknowense, Aspergillus oryzae* and *Rhizopus stolonifera.*

Sugar Transporters

Glucose transporters are a wide group of membrane proteins that facilitate the transport of glucose across the plasma membrane. Because glucose is a vital source of energy for all life, these transporters are present in all phyla. In yeast, and especially in *Saccharomyces cerevisiae* glucose transport takes place through facilitated diffusion. The transport proteins are mainly from the yeast hexose transporters (HXTs) family, with Hxt 1-7 being the main involved transporter; and with Gal2 having a high affinity for galactose.

Most studied xylose transporters are MFS (major facilitator superfamily) type transporters with 12 transmembrane domains. MFS transporters are conserved from bacteria to higher eukaryotes and include the bacterial permease, HXTs, human glucose transporters (GLUTs), and plant sugar transporters. However, other type of transporters have been overlooked.

The present disclosure describes the identification and characterization of putative xylose transporters in the non-model oleaginous yeasts *Rhodosporidium toruloides* and *Lipomyces starkeyi*; along with the screening and characterization of glucose and xylose transporters from *Arabidopsis thaliana* SWEET. *L. starkeyi* LST1_205437 and *A. thaliana* SWEET were found to have the ability to co-ferment glucose and xylose. *L. starkeyi* LST1_205437 can partially co-utilize glucose and xylose, and AtSWEET transporter showed simultaneous co-utilization of both sugars. Embodiments provide recombinant yeast, compositions thereof and methods of uses thereof, wherein the yeast can comprise two or more of the transporters to further increase and improve the ability of the yeast to co-ferment several sugars, such as glucose and xylose, simultaneously.

For example, two or more transporters having distinct sugar uptake phenotype can be combined in a yeast to ensure simultaneous co-fermentation of sugars. The two or more transporters can be selected from SWEET1, SWEET4, SWEET5, SWEET7, SWEET8 and LST1_205437.

The mechanism of xylose transport in SWEETs have not been studied. SWEETs are a newly discovered family of transporters with distinct 7 transmembrane structure that play a key role in plant development and sugar translocation within the plant phloem. SWEETs are comprised of 7 transmembrane domains of which N-terminal three helixes shares sequence similarity to C-terminal three helixes, which in turn are connected by a non-conserved fourth domain. AtSWEET1 and OsSWEET2b confer yeast growth on glucose. *A. thaliana* has 17 different SWEET transporters that can transport either monosaccharides or disaccharides across a membrane via concentration gradient (FIG. 2B). *A.*

*thaliana* SWEETs can be divided into two distinct groups based on conserved residues dictating sugar preference to monosaccharide and disaccharide; AtSWEET13, for example, has both glucose and sucrose transport activity.

All 17 AtSWEETs were screened to identify xylose and glucose transporters. Interestingly, the 17 AtSWEETs share sequence similarity and yet showed very different sugar uptake phenotype in glucose or xylose medium. AtSWEET1 was found to be a glucose transporter with almost no xylose transport capacity, whereas AtSWEET4 and AtSWEET7 showed both glucose and xylose transport capacity. Moreover, among screened transporters, AtSWEET7 exhibited true co-fermentation phenotype. The kinetic analysis of AtSWEET7 revealed no glucose inhibition of xylose transport, though the glucose and xylose transport kinetic properties were poorer than ScGal2 and LST_205437. The study of glucose transport cycle in OsSWEET2b and SemiSWEET revealed that substrate transport mechanism varies between closely related families of transporters. The homology models of AtSWEET1 and AtSWEET7 intermediate states were constructed and the substrate docked in the binding site. Using previously investigated crystal structure information and complete glucose transport cycle molecular dynamics of OsSWEET2b and SemiSWEET, homology models of AtSWEET1 and AtSWEET7 were constructed in OC and OF states; which revealed that the substrate molecules were sandwiched between Tyr59 and Trp183 in AtSWEET7 thereby favoring the structural transition to other states for efficient transport. The lack of one of the aromatic counterparts may lead to the increase in conformation degrees of rotational freedom that possibly affects the substrate stability in the binding site and the transport. Mutation of Trp59 decreases the xylose transport in AtSWEET7. A hydrophobic gate at the center of transporter was identified, and opening of these gates drives the conformational transition of IF state. In AtSWEET1, Phe169 is located just beneath the hydrophobic gates and the mutation of this residue to alanine increases the glucose uptake and shows partial cotransport of xylose.

Figure 12:
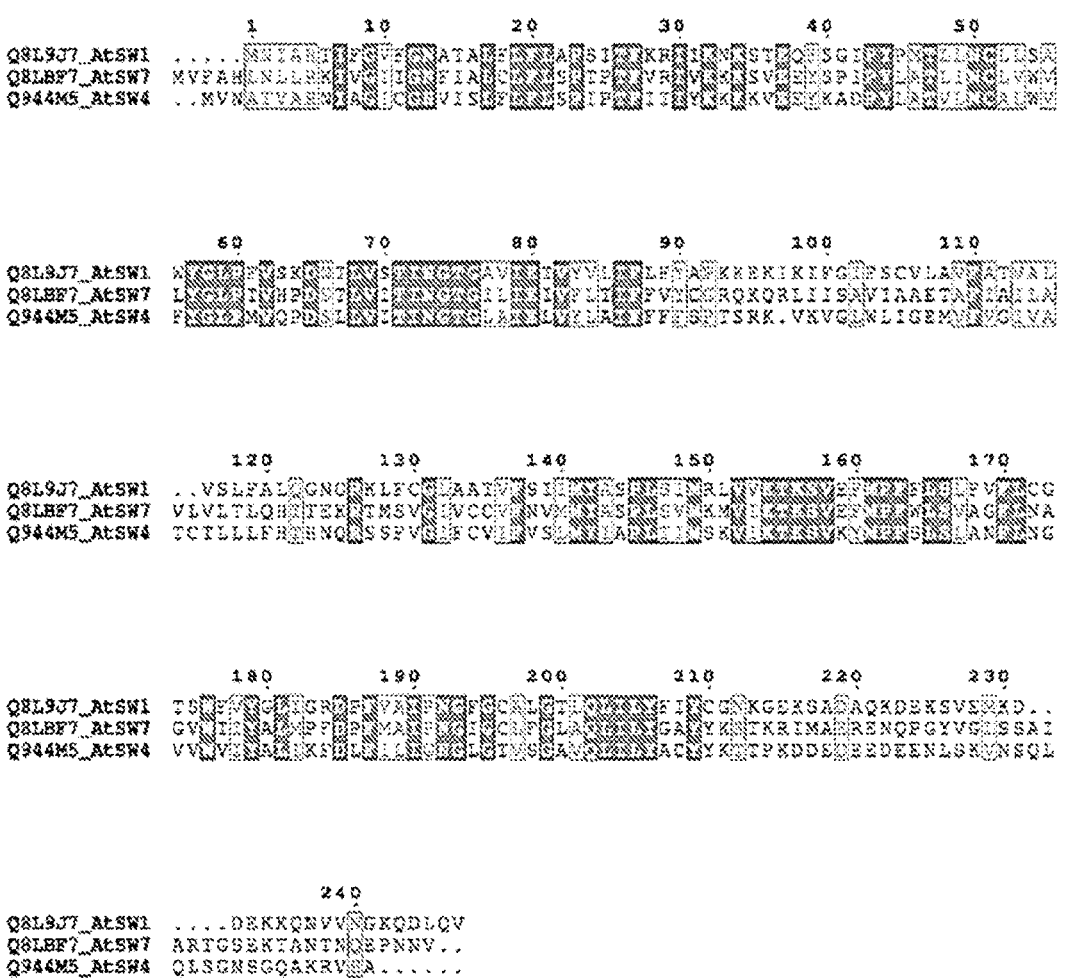
FIG. 12 illustrates protein sequence alignment of AtSWEET1 and AtSWEET7. The numbering above refers to the AtSWEET1 sequence. Conserved residues are indicated in dark boxes. Similar residues are indicated in light boxes. Q8L9J7_AtSW1 is SEQ ID NO:1; Q8LBF7_AtSW7 is SEQ ID NO:2; Q944M5_AtSW4 is SEQ ID NO:3.
Figure 13:
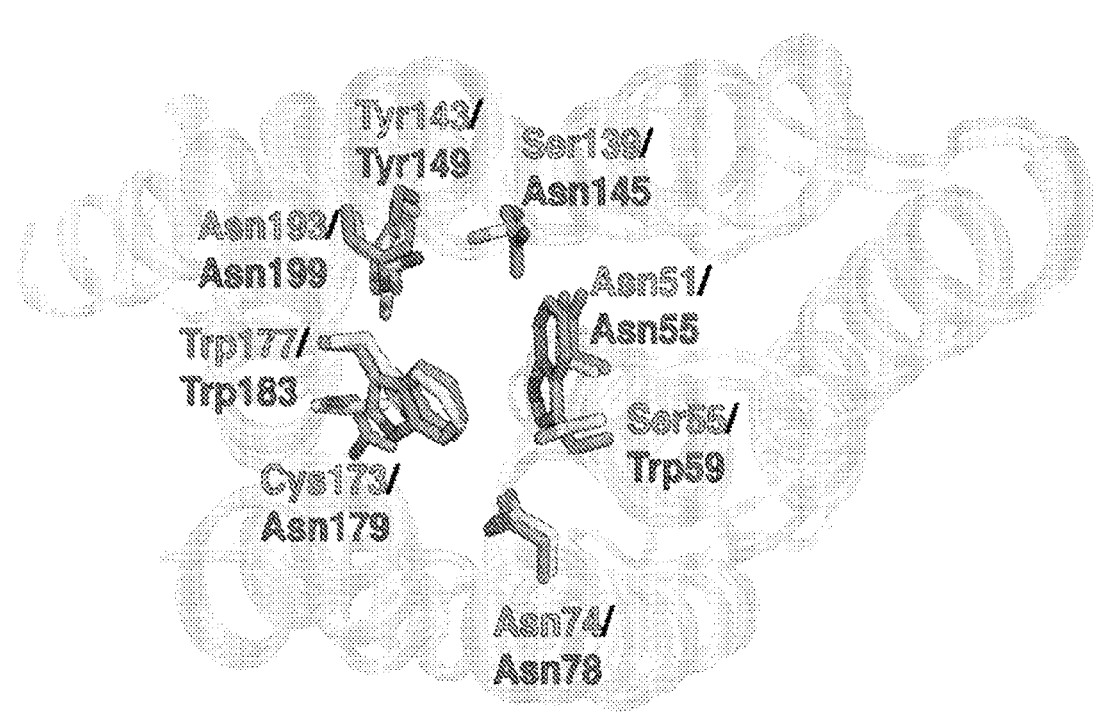
FIG. 13 illustrates AtSWEET1 and AtSWEET7 substrate binding residues. Residues around 5 Å of the binding site of AtSWEET1 and AtSWEET7 represented in green and magenta, respectively.
Figure 14A:
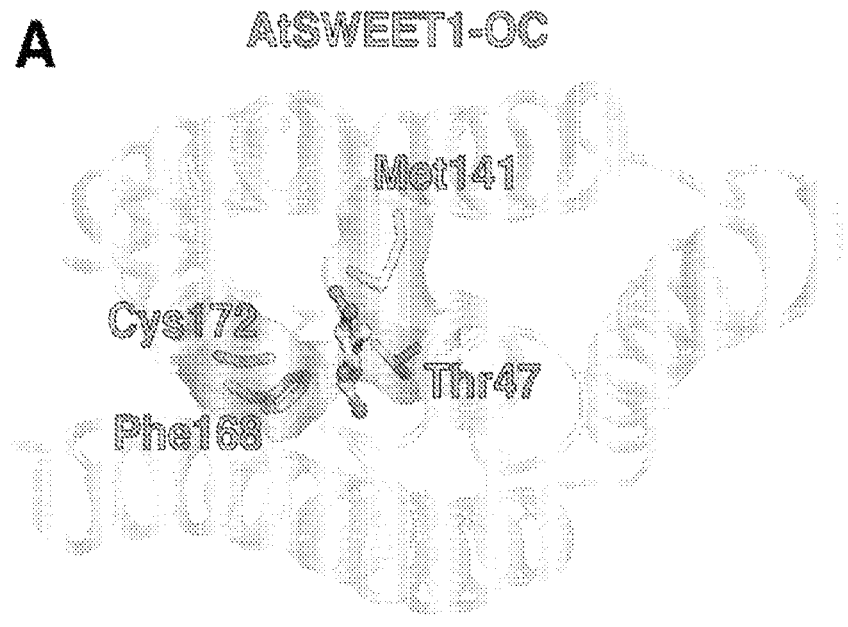
FIG. 14A illustrates AtSWEET1 hydrophobic gates. The residues in the transmembrane helices act as a secondary hydrophobic gate are shown in transparent surface representation, respectively.
Figure 14B:
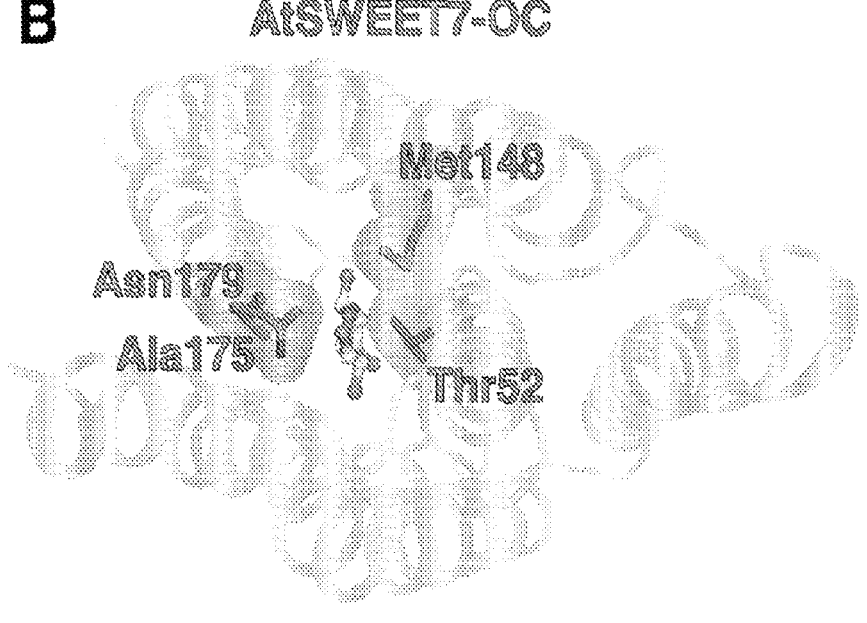
FIG. 14B illustrates AtSWEET7 hydrophobic gates. The residues in the transmembrane helices act as a secondary hydrophobic gate are shown in transparent surface representation, respectively.
Figures 15A, 15B, 15C, 15D, 15E, 15F:
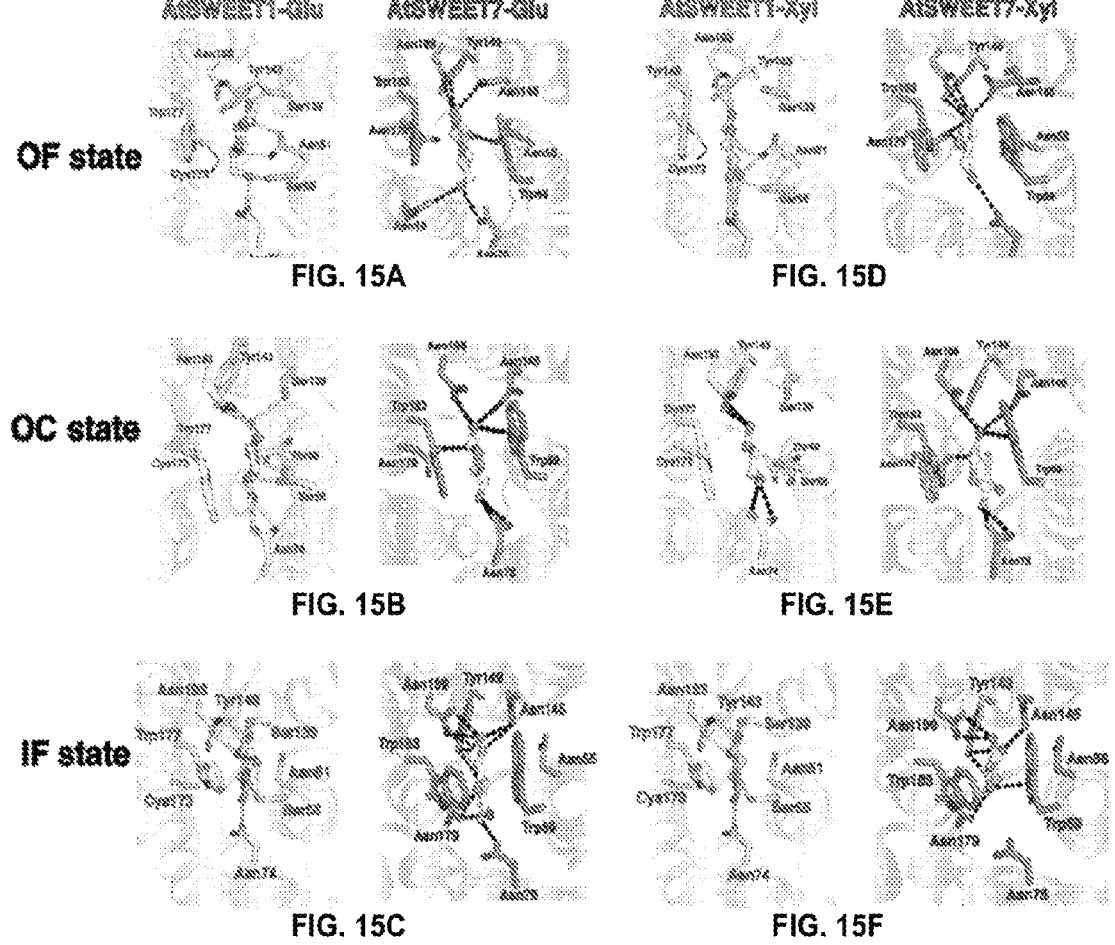
FIG. 15A illustrates dockposes of the predicted binding mode of D-glucose in AtSWEET1 and AtSWEET7 in OF conformation.
FIG. 15B illustrates dockposes of the predicted binding mode of D-glucose in AtSWEET1 and AtSWEET7 in OC conformation.
FIG. 15C illustrates dockposes of the predicted binding mode of D-glucose in AtSWEET1 and AtSWEET7 in IF conformation.
FIG. 15D illustrates dockposes of the predicted binding mode of D-xylose in AtSWEET1 and AtSWEET7 in OF conformation.
FIG. 15E illustrates dockposes of the predicted binding mode of D-xylose in AtSWEET1 and AtSWEET7 in OC conformation.
FIG. 15F illustrates dockposes of the predicted binding mode of D-xylose in AtSWEET1 and AtSWEET7 in IF conformation.

FIG. 12 compares the amino acid sequences of AtSWEET1, AtSWEET7 and AtSWEET4. Conserved amino acids (dark boxes and white letters) and similar amino acids (light boxes and dark letters) are noted. In an embodiment, a transporter has 90, 91, 92, 93, 94, 95, 96, 97, 98, 99, 99.5% or more homology or identity to AtSWEET1, AtSWEET7 and AtSWEET4 transporter polypeptides. In an embodiment, amino acid substitutions occur at non-conserved positions. In an embodiment, amino acid substitutions occur at non-similar positions. In an embodiment, amino acid substitutions occur at non-conserved positions and at non-similar positions.

A SWEET1 polypeptide can have an amino acid sequence of, for example, GenBank Accession No. Q8L9J7, NP_001323400.1, or A0A1P8AX31, as obtained from *A. thaliana*. Alternatively, a SWEET1 polypeptide can have an amino acid sequence such as A0A0V0H2R4, as obtained from *Solanum chacoense*, A0A1 R3FXN2, as obtained from *Corchorus capsularis*, A0A1U8GE38, as obtained from *Capsicum annuum*, A0A1U8Q8E3, as obtained from *Nelumbo nucifera*, AOA287FZP5, as obtained from *Hordeum vulgare*, A0A287M9A7, as obtained from *Hordeum vulgare*, A0A287M9B1, A0A287M9B6, A0A287M9B7, or A0A446Q8W8, as obtained from *Triticum turgidum*, or AOA2I0AM70, as obtained from *Apostasia shenzhenica*. These polypeptides can have at least 90% identity to the SWEET1 polypeptide of *A. thaliana*.

A SWEET4 polypeptide can have an amino acid sequence of, for example, GenBank Accession No. Q944M5, OAP06453.1, AAM64306.1, AEE77391.1, or NP_566829.1, as obtained from *A. thaliana*. Alternatively, a SWEET4 polypeptide can have an amino acid sequence such as XP_002877087.1, as obtained from *Arabidopsis lyrata*; XP_006395383.1, as obtained from *Eutrema salsugineum*; XP_013595545.1 as obtained from *Brassica oleracea*; XP_009151901.1, as obtained from *Brassica rapa*; XP_010502807.1 and XP_101514508.1, as obtained from *Carmelina sativa*; XP_006291730.1, as obtained from *Capsella rubella*; XP_0912938.1, as obtained from *Brassica campestris*, or XP_013720835.1, as obtained from *Brassica rapus*. These polypeptides can have at least 90% identity to the SWEET4 polypeptide of *A. thaliana*.

A SWEET5 polypeptide can have an amino acid sequence of, for example, GenBank accession number OAO92483.1, NP_001330980.1, ANM69288.1, or NP_201091.2, as obtained from *A. thaliana*. Alternatively, a SWEET5 polypeptide can have an amino acid sequence such as XP_002866519.1, as obtained from *Arabidopsis lyrata*; XP_006281467.1, as obtained from *Capsella rubella*; and XP_006394345.1, as obtained from *Eutrema salsugineum*. These polypeptides can have at least 90% identity to the SWEET5 polypeptide of *A. thaliana*.

A SWEET7 polypeptide can have an amino acid sequence of, for example, GenBank accession number NP_567366.1, Q8LBF7.1, AAM64793.1, or AEE82936.1, as obtained from *A. thaliana*. Alternatively, a SWEET7 polypeptide can have an amino acid sequence such as XP_002872539.1, as obtained from *Arabidopsis lyrata*. This polypeptide can have at least 90% identity to the SWEET7 polypeptide of *A. thaliana*.

Figure 8:
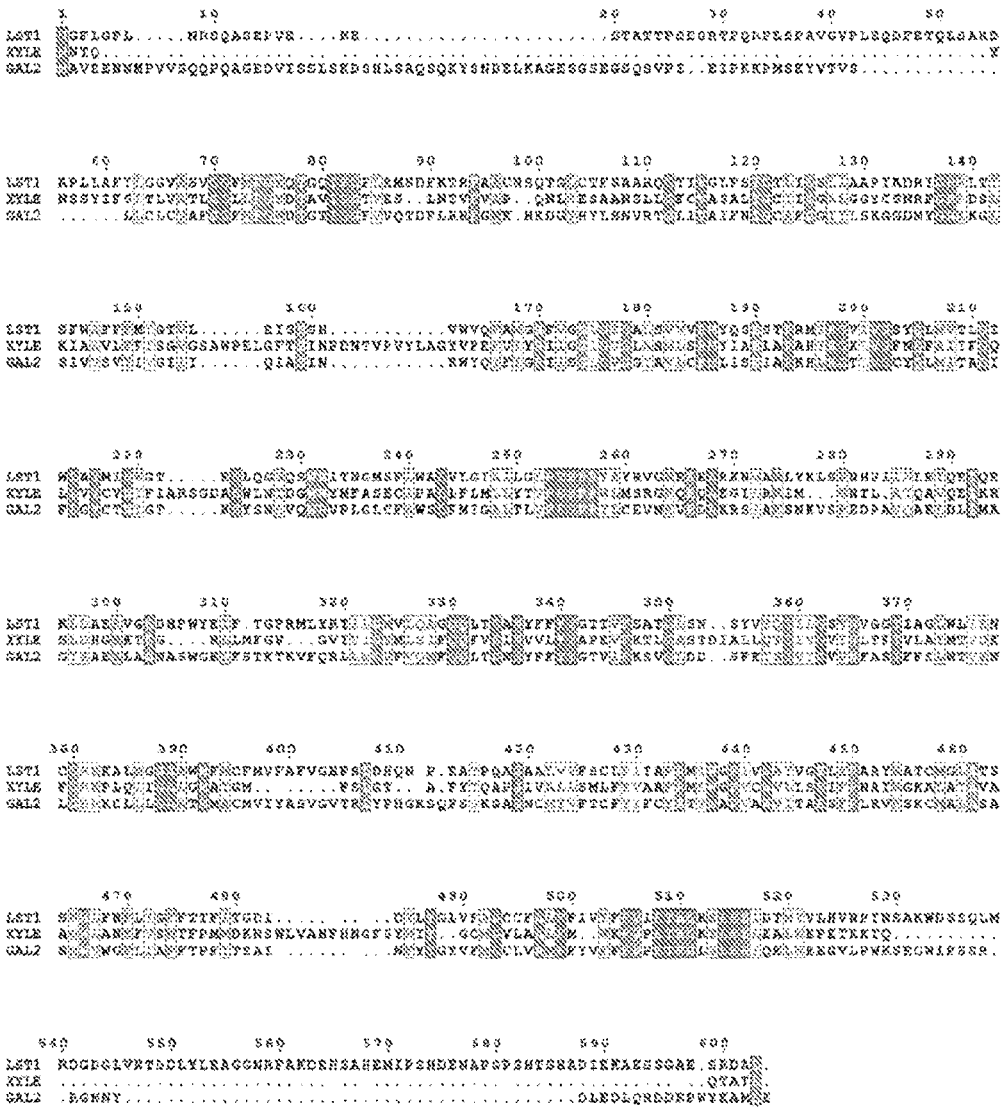
FIG. 8 illustrates protein sequence alignment of XylE, LST1 and ScGal2. The numbering above refers to the LST1_205437 sequence. Conserved residues are indicated in boxes with white letters. Similar residues are indicated in boxes with dark letters. The LST1 sequence is SEQ ID NO:4; the XylE sequence is SEQ ID NO:31; the ScGal2 sequence is SEQ ID NO:32.
Figures 9E, 9F, 9G, 9H:
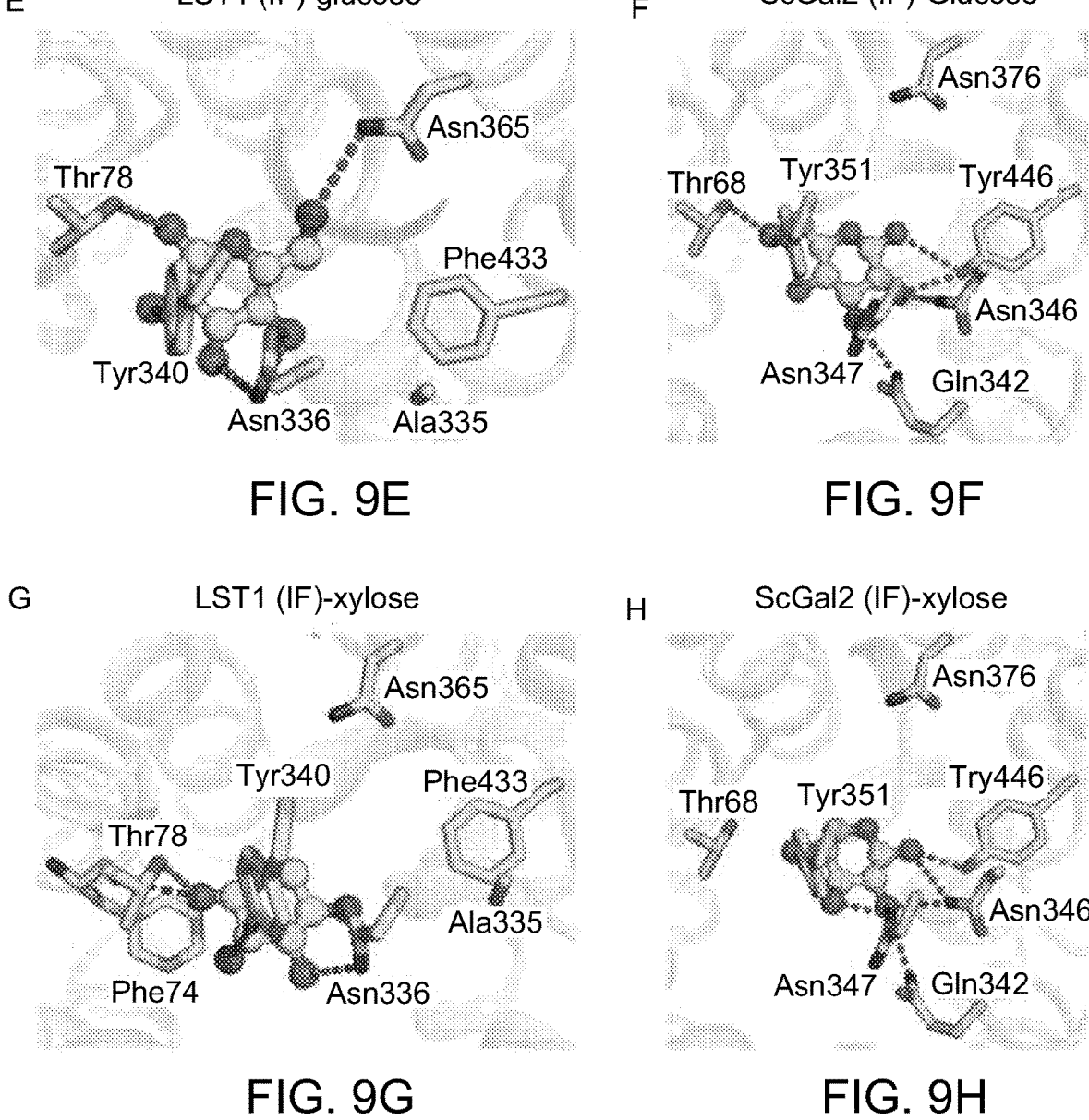
FIG. 9E illustrates the predicted binding orientation of D-glucose in LST1 in IF conformation.
FIG. 9F illustrates the predicted binding orientation of D-glucose in ScGal2 in IF conformation.
FIG. 9G illustrates the predicted binding orientation of D-xylose in LST1 in IF conformation.
FIG. 9H illustrates the predicted binding orientation of D-xylose in ScGal2 in IF conformation.

Furthermore, the sequence alignment of LST1_205437 (GenBank accession number ODQ75362.1) with GAL2 and XYLE (FIG. 8) illustrate how conserved amino acids (dark boxes with white letters) and similar amino acids (boxes with dark letters) residues are distributed along the amino acid sequence. In an embodiment, a transporter has 90, 91, 92, 93, 94, 95, 96, 97, 98, 99, 99.5% or more homology or identity to a LST1_205437 transporter polypeptide. In an embodiment, amino acid substitutions occur at non-conserved positions. In an embodiment, amino acid substitutions occur at non-similar positions. In an embodiment, amino acid substitutions occur at non-conserved positions and at non-similar positions.

Figure 3A:
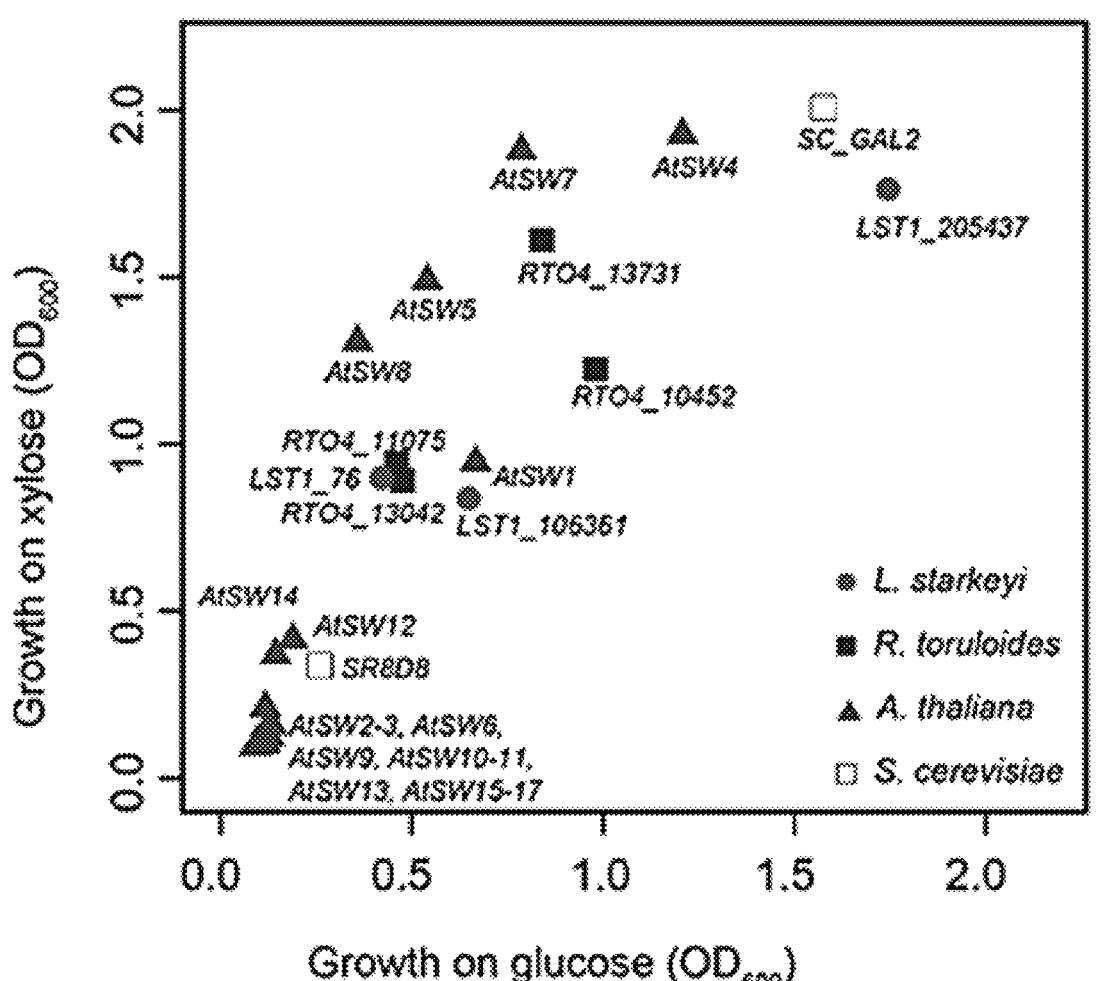
FIG. 3A-3B illustrates *L. starkeyi, R. toruloides* and *A. thaliana* SWEET transporter screening for growth on glucose or xylose using Bioscreen C.
Figure 3B:
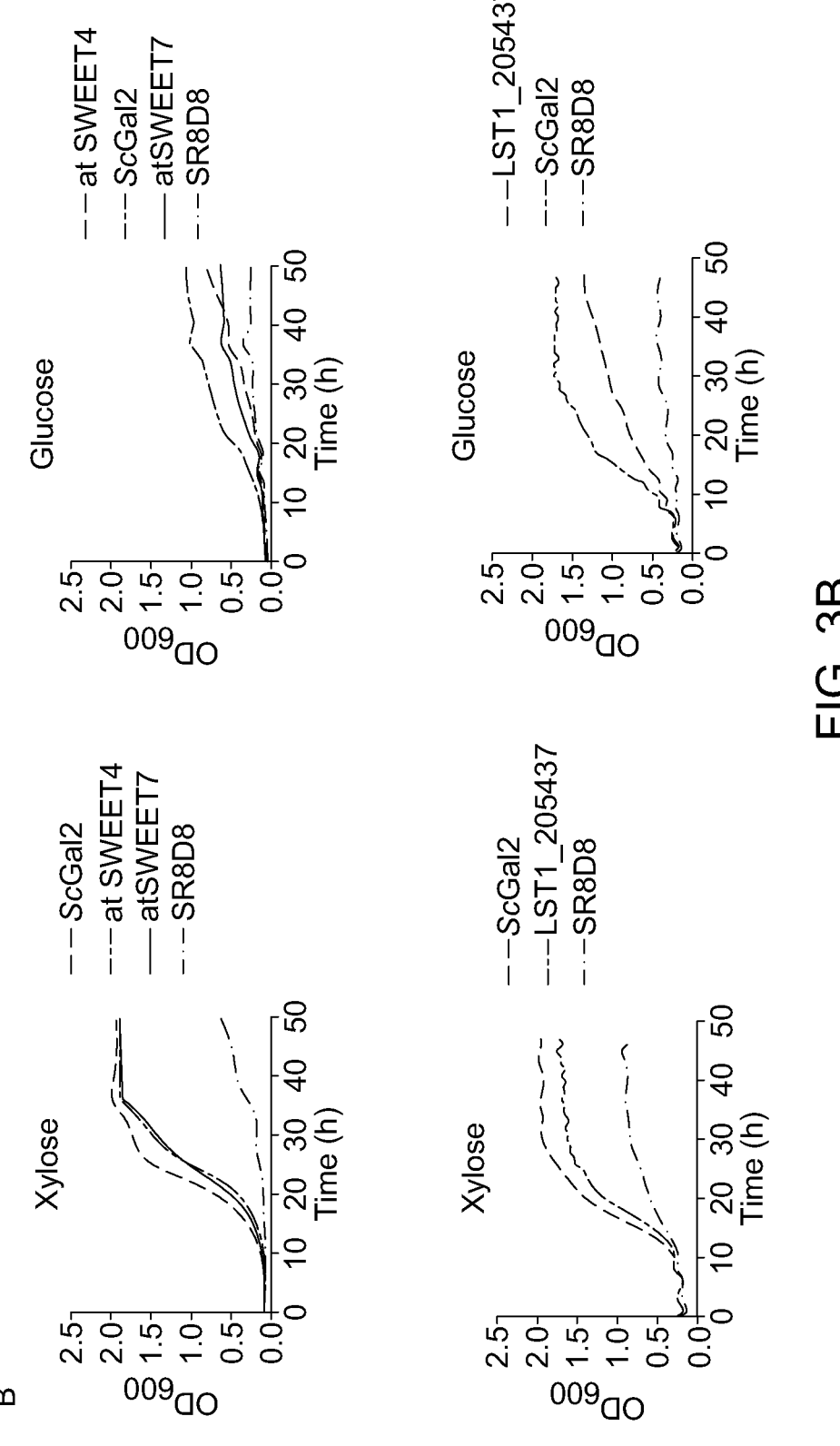

To identify and characterize xylose and glucose co-transporting transporters engineered xylose fermenting *S. cerevisiae* strain (SR8D8), which lacks major hexose transporters (1-7 HXT, GAL2) and is not capable of growing on any pentose or hexose sugars, was used. *A. thaliana* SWEET and *S. starkeyi* putative glucose/xylose transporters were expressed in SR8D8 and screened using either glucose or xylose containing medium. The screening showed that SWEET4, SWEET5 and SWEET7 and LST1_205437 were capable of sustaining an efficient growth on glucose or xylose (FIG. 3). The ability of SWEET4, SWEET5 and SWEET7 and LST1_205437 to conferment both glucose and xylose were assessed in flask fermentation using *S. cerevisiae* GAL2 as a negative control (FIG. 4). The results showed an ability of SWEET4, SWEET5, SWEET7, and LST1_205437 expressing SR8D8 strains to simultaneously utilize glucose and xylose, whereas SR8D8 expressing GAL2 show sequential manner of sugar utilization. Furthermore, SWEET7 and LST1_205437 were investigated for xylose uptake kinetics in the presence of glucose. The glucose inhibition kinetic analysis of transporters revealed that SWEET7 transporters do not have any xylose transport inhibition in the presence of both 25 mM and 100 mM glucose. LST1_205437 transporter shows glucose concentration dependent inhibition of xylose transport. However, GAL2 transporter showed complete xylose inhibition even at the presence of 25 mM glucose (FIG. 4). The kinetic data correlated with phenotypic data from flask fermentations.

The specificity of a sugar transporter can be uncertain, or not yet asserted fully. Based on detailed analysis of such transporter sequence, it can be assumed that said transporter would likely be a sugar transporter, for example a glucose transporter or a xylose transporter. The likelihood of a transporter to be a glucose (or xylose) transporter can for example rely on its comparison to known glucose (or xylose) transporter. Said sugar transporters can be referred to as putative glucose (or xylose) transporters. Putative sugar transporters can be identified as such when, during a screening process, they show some ability to transport sugar. For example, a transporter that has the ability to transport 10%, 20%, 30%, 40%, 50%, 60%, 70%, 80%, 90%, or more glucose, as compared to the amount of glucose that can be transported by a known and characterized glucose transporter, can be described as a putative glucose transporter. A transporter that has the ability to transport 10%, 20%, 30%, 40%, 50%, 60%, 70%, 80%, 90%, or more xylose, as compared to the amount of xylose that can be transported by a known characterized xylose transporter, can be described as a putative xylose transporter. In an embodiment, a putative glucose transporter and/or a putative xylose transporter can be used to further transform a microorganism. For example, putative sugar transporters can be obtained from *Rhodosporidium toruloides*, such as RT04_11075, and RT04_13042, two putative glucose transporters, or RT04_13731 and RT04_10452, two putative xylose transporters. See Table 3.

Sugar Utilization

Improved sugar utilization, increased sugar utilization, improved sugar utilization rate, and increased sugar utilization rate refers to increasing the amount of one or more sugars (e.g., glucose, xylose, galactose, pentose sugars, hexose sugars, and other sugars) fermented or consumed over a specific period of time and/or increasing the rate at which one or more sugars are consumed in a specified amount of time. In an embodiment the rate of fermentation or consumption of pentose sugars, the rate fermentation or consumption of hexose sugars, or both the fermentation or consumption rate of pentose sugars and hexose sugars is improved or increased. In some embodiments, a microorganism that has been modified as described herein has improved sugar utilization if the amount of sugar fermented or consumed by the microorganism over a specified period of time (e.g., over about 1, 2, 5, 10, 15, 20, 24, 25, 30, 36, 48, or more or hours is at least about 10%, 15%, 20%, 25%, 30%, 40%, 50%, 60%, 70%, or 80% more than the amount of sugar consumed over the same specified period of time for a wild-type or control microorganism (e.g., an otherwise identical strain that has not been recombinantly modified as described herein). In some embodiments, a genetically engineered microorganism that has been modified as described herein has improved sugar utilization if the amount of sugar (e.g., glucose, xylose, galactose, or other sugars) consumed or fermented by the microorganism over a specified period of time (e.g., over about 1, 2, 5, 10, 15, 20, 24, 25, 30, 36, 48 or more hours) is at least about 10%, 15%, 20%, 25%, 30%, 40%, 50%, 60%, 70%, or 80% more than the amount of sugar fermented or consumed over the same specified period of time for a control or wild-type microorganism (e.g., an otherwise identical bacteria or yeast strain that has not been recombinantly modified as described herein).

In some embodiments, a microorganism that has been recombinantly modified as described herein has improved sugar utilization if the rate at which the cell consumes a specified amount of sugar (e.g., glucose, xylose, galactose, pentose sugars, hexose sugars, or other sugars) is at least about 10%, 15%, 20%, 25%, 30%, 40%, 50%, 60%, 70%, or 80% greater than the rate for a control or wild-type microorganism under the same culture conditions. In some embodiments, a microorganism that has been modified as described herein has improved sugar utilization if the rate at which the microorganism consumes a specified amount of sugar (e.g., glucose, xylose, galactose, pentose sugars, hexose sugars, or other sugars) is at least about 10%, 15%, 20%, 25%, 30%, 40%, 50%, 60%, 70%, 80%, or 90% greater than the rate for a control or wild-type microorganism under the same culture conditions.

Improved Sugar Co-Utilization

A microorganism that co-utilizes, co-ferments, or co-consumes (or exhibits co-utilization, co-fermentation, or co-consumption) of two or more different sugars (e.g., xylose, glucose, galactose) or two or more different types of sugars (e.g., pentose sugars, hexose sugars) is a microorganism that when grown in medium containing two or more different sugars (in equal ratios or in different ratios) consumes (ferments) the sugars simultaneously rather than, in contrast, consuming (fermenting) the sugars sequentially (e.g., consuming (fermenting) glucose before consuming (fermenting) the xylose, or other sugars).

Improved co-utilization or increased co-utilization, means co-utilization of two or more different sugars (e.g., glucose, xylose, galactose, or other sugars), by increasing the consumption of one or more of the sugars (e.g., 1, 2, 3, 4, or more sugars) by a microorganism, e.g., yeast, at the same time over a specific period of time (e.g., about 1, 2, 5, 10, 15, 20, 24, 25, 30, 36, 48 or more hours) and/or increasing the rate at which a specified amount of one or more of the sugars are consumed by the microorganism over a specified period of time (e.g., about 1, 2, 5, 10, 15, 20, 24, 25, 30, 36, 48 or more hours). In some embodiments, a microorganism that has been modified as described herein has improved sugar co-utilization if the amount of total sugars (e.g., glucose, xylose, galactose, etc.) consumed by a microorganism over a specified period of time (e.g., about 1, 2, 5, 10, 15, 20, 24, 25, 30, 36, 40, 48, or more hours) is at least about 10%, 15%, 20%, 25%, 30%, 40%, 50%, 60%, 70%, 80%, or 90% greater than the amount of total sugars (e.g., glucose, xylose, galactose, etc.) consumed over the same specific period of time for a control or wild-type cell (e.g., an otherwise identical strain in that has not been recombinantly modified as described herein). In some embodiments, a host cell that has been modified as described herein has improved sugar co-utilization if the amount of total sugars (e.g., glucose, xylose, galactose, etc.) consumed by the cell over a specified period of time (e.g., about 1, 2, 5, 10, 15, 20, 24, 25, 30, 36, 40, or 48 hours) is at least 10%, 15%, 20%, 25%, 30%, 40%, 50%, 60%, 70%, 80%, or 90% more than the amount of total sugars (e.g., glucose, xylose, galactose) consumed over the same specific period of time for a control or wild-type microorganism (e.g., an otherwise identical strain in that has not been recombinantly modified as described herein).

In some embodiments, a microorganism that has been modified as described herein has improved sugar co-utilization if the rate at which a specified amount of total sugars (e.g., glucose, xylose, galactose, etc.) is consumed by the microorganism in a specified amount of time (e.g., about 1, 2, 5, 10, 15, 20, 24, 25, 30, 36, 40, 48 or more hours) is at least about 10%, 15%, 20%, 25%, 30%, 40%, 50%, 60%, 70%, 80%, or 90% faster than the rate at which the same specified amount of total sugars is consumed in the same specified amount of time by a control or wild-type micro-organism (e.g., an unmodified host cell of the same type). In some embodiments, a host cell that has been modified as described herein has improved sugar co-utilization if the rate at which a specified amount of total sugars (e.g., glucose plus xylose) is consumed by the host cell in a specified amount of time (e.g., about 1, 2, 5, 10, 15, 20, 24, 25, 30, 35, 40, or 48 hours) is at least about 10%, 15%, 20%, 25%, 30%, 40%, 50%, 60%, 70%, 80%, or 90% faster than the rate at which the same specified amount of total sugars is consumed in the same specified amount of time by a control or wild-type microorganism (e.g., an unmodified microorgan-ism of the same type).

In some embodiments, improved sugar co-utilization can occur when the rate of consumption of one of the sugars (e.g. glucose) is reduced as compared to a control microorganism, but the rate of consumption of one or more of the other sugars is increased as compared to a control microorganism. This is considered improved sugar co-utilization, because, inter alia, the sugars are fermented simultaneously rather than sequentially. While the rate of consumption of the first sugar (e.g., glucose) can be reduced, the amount of total sugars consumed or fermented over a specific time period is increased resulting in improved sugar co-utilization.

When co-utilizing sugars, a microorganism can consume at least about 1%, 2.5%, 5%, 7.5%, or 10% of the initial amount of a first sugar (e.g., xylose) in the medium during the time the microorganism consumes about 10% of the initial amount of a second sugar (e.g., glucose) in the medium; at least about 5%, 10%, 15%, or 20% of the initial amount of a first sugar (e.g., xylose) in the medium during the time the microorganism consumes about 20% of the initial amount of a second sugar (e.g. glucose) in the medium; at least about 10%, 15%, 20%, 25%, or 30% of the initial amount of a first sugar (e.g. xylose) in the medium during the time the microorganism consumes about 30% of the initial amount of a second sugar (e.g. glucose) in the medium; at least about 10%, 20%, 25%, 30%, 35%, or 40% of the initial amount of a first sugar (e.g. xylose) in the medium during the time the microorganism consumes about 40% of the initial amount of a second sugar (e.g. glucose) in the medium; at least about 10%, 20%, 30%, 35%, 40%, 45%, or 50% of the initial amount of a first sugar (e.g. xylose) in the medium during the time the microorganism consumes about 50% of the initial amount of a second sugar (e.g. glucose) in the medium; at least about 20%, 40%, 45%, 50%, 55%, or 60% of the initial amount of a first sugar (e.g. xylose) in the medium during the time the microorganism consumes about 60% of the initial amount of a second sugar (e.g. glucose) in the medium; at least about 40%, 50%, 55%, 60%, 65%, or 70% of the initial amount of a first sugar (e.g. xylose) in the medium during the time the microorganism consumes about 70% of the initial amount of a second sugar (e.g. glucose) in the medium; at least about 50%, 60%, 65%, 70%, 75%, or 80% of the initial amount of a first sugar (e.g. xylose) in the medium during the time the microorganism consumes about 80% of the initial amount of a second sugar (e.g. glucose) in the medium; or at least about 50%, 60%, 70%, 75%, 80%, 85%, or 90% of the initial amount of a first sugar (e.g. xylose) in the medium during the time the microorganism consumes about 90% of the initial amount of a second sugar (e.g. glucose) in the medium.

When co-utilizing sugars, a microorganism can consume at least about 1%, 2.5%, 5%, 7.5%, or 10% of the initial amount of a first sugar and a second sugar (e.g., xylose and galactose) in the medium during the time the microorganism consumes about 10% of the initial amount of a third sugar (e.g., glucose) in the medium; at least about 5%, 10%, 15%, or 20% of the initial amount of a first sugar and a second sugar (e.g., xylose and galactose) in the medium during the time the microorganism consumes about 20% of the initial amount of a third sugar (e.g. glucose) in the medium; at least about 10%, 15%, 20%, 25%, or 30% of the initial amount of a first sugar and a second sugar (e.g., xylose and galactose) in the medium during the time the microorganism consumes about 30% of the initial amount of a third sugar (e.g. glucose) in the medium; at least about 10%, 20%, 25%, 30%, 35%, or 40% of the initial amount of a first sugar and a second sugar (e.g., xylose and galactose) in the medium during the time the microorganism consumes about 40% of the initial amount of a third sugar (e.g. glucose) in the medium; at least about 10%, 20%, 30%, 35%, 40%, 45%, or 50% of the initial amount of a first sugar and a second sugar (e.g., xylose and galactose) in the medium during the time the microorganism consumes about 50% of the initial amount of a third sugar (e.g. glucose) in the medium; at least about 20%, 40%, 45%, 50%, 55%, or 60% of the initial amount of a first sugar and a second sugar (e.g., xylose and galactose) in the medium during the time the microorganism consumes about 60% of the initial amount of a third sugar (e.g. glucose) in the medium; at least about 40%, 50%, 55%, 60%, 65%, or 70% of the initial amount of a first sugar and a second sugar (e.g., xylose and galactose) in the medium during the time the microorganism consumes about 70% of the initial amount of a third sugar (e.g. glucose) in the medium; at least about 50%, 60%, 65%, 70%, 75%, or 80% of the initial amount of a first sugar and a second sugar (e.g., xylose and galactose) in the medium during the time the microorganism consumes about 80% of the initial amount of a third sugar (e.g. glucose) in the medium; or at least about 50%, 60%, 70%, 75%, 80%, 85%, or 90% of the initial amount of a first sugar and a second sugar (e.g., xylose and galactose) in the medium during the time the microorganism consumes about 90% of the initial amount of a third sugar (e.g. glucose) in the medium.

In an embodiment, sugars are co-utilized when about 10%, 15%, 20%, 25%, 30%, 40%, 50%, 60%, 70%, 80%, or 90% of both a first and second sugar are consumed in about 1, 2, 5, 10, 15, 20, 24, 25, 30, 35, 40, or 48 hours. In an embodiment, sugars are co-utilized when about 30%, 40%, or 50% of both a first and second sugar are consumed in about 15, 20, 24, 25, 30, 35, 40, or 48 hours. In an embodiment, sugars are co-utilized when about 50%, 60%, or 70% of both a first and second sugar are consumed in about 20, 24, 25, 30, 35, 40, or 48 hours. In an embodiment, sugars are co-utilized when about 60%, 70%, or 80% of both a first and second sugar are consumed in about 24, 25, 30, 35, 40, or 48 hours.

Gene Disruptions and Mutations

A genetic mutation comprises a change or changes in a nucleotide sequence of a gene or related regulatory region or polynucleotide that alters the nucleotide sequence as com-pared to its native or wild-type sequence. Mutations include, for example, substitutions, additions, and deletions, in whole or in part, within the wild-type sequence. Such substitutions, additions, or deletions can be single nucleotide changes (e.g., one or more point mutations), or can be 2, 3, 4, 5, 6, 7, 8, 9, 10, or more nucleotide changes. Mutations can occur within the coding region of the gene or polynucleotide as well as within the non-coding and regulatory elements of a gene. A genetic mutation can also include silent and conservative mutations within a coding region as well as changes which alter the amino acid sequence of the polypeptide encoded by the gene or polynucleotide. A genetic mutation can, for example, increase, decrease, or otherwise alter the activity (e.g., biological activity) of the polypeptide product. A genetic mutation in a regulatory element can increase, decrease, or otherwise alter the expression of sequences operably linked to the altered regulatory element.

A gene disruption is a genetic alteration in a polynucleotide or gene that renders an encoded gene product (e.g., SWEET1, SWEET4, SWEET5, SWEET7, LST1_205437, HXT 1-7, or GAL2) attenuated or more active (e.g., produced at a lower amount, greater amount or having higher or lower biological activity). A gene disruption can include a disruption in a polynucleotide or gene that results in reduced expression of an encoded gene product, or expression of a gene product with increased or reduced or attenuated biological activity. The genetic alteration can be, for example, or addition or deletion of a regulatory element required for transcription or translation of the polynucleotide or gene, deletion or addition of a regulatory element required for transcription or translation or the polynucleotide or gene, addition of a different regulatory element required for transcription or translation or the gene or polynucleotide, deletion of a portion (e.g. 1, 2, 3, 6, 9, 21, 30, 60, 90, 120 or more nucleic acids) of the gene or polynucleotide, which results in an partially active gene product or a gene product with greater activity, replacement of a gene's promoter with a weaker promoter or a stronger promoter, replacement or insertion of one or more amino acids of the encoded protein to reduce its activity, stability, or concentration, to increase its activity, stability, or concentration, or inactivation or activation of a gene's transactivating factor such as a regulatory protein.

Zinc-finger nucleases (ZFNs), Talens, and CRISPR-Cas9 allow double strand DNA cleavage at specific sites in yeast chromosomes such that targeted gene insertion or deletion can be performed (Shukla et al., 2009, Nature 459:437-441; Townsend et al., 2009, Nature 459:442-445). This approach can be used to modify the promoter of endogenous genes or the endogenous genes themselves to modify expression of SWEET1, SWEET4, SWEET5, SWEET7, LST1_205437, HXT 1-7, or GAL2 which can be present in the genome of yeast of interest. ZFNs, Talens or CRISPR/Cas9 can be used to change the sequences regulating the expression of the polypeptides to increase or decrease the expression or alter the timing of expression beyond that found in a non-engineered or wild-type yeast, or to delete the wild-type polynucleotide, or replace it with a deleted or mutated form to alter the expression (e.g., increase or decrease) and/or activity of SWEET1, SWEET4, SWEET5, SWEET7, LST1_205437, HXT 1-7, or GAL2.

As discussed above, beside variable sugar uptake phenotype, the SWEETs transporter have sequence similarities, and share various highly conserved amino acid (in dark boxes in FIG. 12), and similar amino acids (in light boxes in FIG. 12). Likewise, LST1_205437 shares sequence similarities with GAL2 and XYLE sugar transporters (boxes in FIG. 8). Amino acids substitutions aimed at modifying transporter sugar uptake phenotype can target any amino acids. In an embodiment non-conserved amino acids, non-similar amino acids, or both non-conserved and non-similar amino acids are targeted for amino acid substitution.

In an embodiment an amino acid substitution can be made at position 365 of LST1_205437. The Asn at position 365 can substituted for an amino acid with a polar neutral side chain (e.g., Ser, Thr, Cys, Asn, Gln, and Tyr), an amino acid with an aliphatic side chain (e.g., Gly, Ala, Val, Leu, or lie), or an amino acid with an hydrophobic side chain (e.g., Gly, Ala, Val, Leu, lie, Pro, Phe, Met, or Trp). The amino acid substitution can be, for example, an Asn365Ser substitution, or an Ans365Val substitution. This amino acid substitution can confer the transporter the ability to co-utilize glucose and xylose.

In an embodiment, the transporter can be mutated. Amino acid substitutions can modify the transporter affinity or specificity for sugar, therefore further altering the sugar preferences of a microorganism, transformed to express such transporter. For example, a AtSWEET1 transporter polypeptide can have an amino acid substitution. The amino acid substitution can be at position 138 or 168, and the amino acid substitution can be an F168A substitution, a S138N substitution, or a S138V substitution. AtSWEET7 transporter polypeptide can have an amino acid substitution. For example, the amino acid substitution can be at position 145 or 175, and the amino acid substitution can be an N145S, N145V, or an A175F substitution. AtSWEET4 transporter polypeptide can have an amino acid substitution. For example, the amino acid substitution can be at position 142 or 172, and the amino acid substitution can be an V142S, V142N, or an A172F substitution.

Polynucleotides and Genes

Polynucleotides contain less than an entire microbial genome and can be single- or double-stranded nucleic acids. A polynucleotide can be RNA, DNA, cDNA, genomic DNA, chemically synthesized RNA or DNA or combinations thereof. A polynucleotide can comprise, for example, a gene, open reading frame, non-coding region, or regulatory element.

A gene is any polynucleotide molecule that encodes a polypeptide, protein, or fragment thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene comprise regulatory elements and coding sequences that are derived from different sources, or regulatory elements and coding sequences that are derived from the same source, but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide. Polynucleotides can encode the polypeptides described herein (e.g., SWEET1, SWEET4, SWEET5, SWEET7, LST1_205437, or variants thereof).

Polynucleotides can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides can be codon optimized for expression in yeast.

Polynucleotides can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. Polynucleotides can encode full-length polypeptides, polypeptide fragments, and variant or fusion polypeptides.

Degenerate polynucleotide sequences encoding polypeptides described herein, as well as homologous nucleotide sequences that are at least about 80, or about 85, 90, 91, 92, 93, 94, 95, 96, 97, 98, or 99% identical to polynucleotides described herein and the complements thereof are also polynucleotides. Degenerate nucleotide sequences are polynucleotides that encode a polypeptide described herein or fragments thereof, but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also are polynucleotides.

Polynucleotides can be obtained from nucleic acid sequences present in, for example, a microorganism such as a yeast or bacterium. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can comprise coding sequences for naturally occurring polypeptides or can encode altered sequences that do not occur in nature.

Unless otherwise indicated, the term polynucleotide or gene includes reference to the specified sequence as well as the complementary sequence thereof.

The expression products of genes or polynucleotides are often proteins, or polypeptides, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process can be modulated, including the transcription, up-regulation, RNA splicing, translation, and post-translational modification of a protein. Any process that reduces, attenuates, or increases the expression of SWEET1, SWEET4, SWEET5, SWEET7, LST1_205437, HXT 1-7, or GAL2 protein expression can be used to make a microorganism described herein.

Polypeptides

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

As used herein, the term "polypeptide of interest" or "polypeptides of interest", "protein of interest", "proteins of interest" includes any or a plurality of any of the SWEET1, SWEET4, SWEET5, SWEET7, LST1_205437, HXT 1-7, or GAL2 polypeptides or other polypeptides (including variant polypeptides) described herein.

A mutated protein or polypeptide comprises at least one deleted, inserted, and/or substituted amino acid, which can be accomplished via mutagenesis of polynucleotides encoding these amino acids. Mutagenesis includes well-known methods in the art, and includes, for example, site-directed mutagenesis by means of PCR or via oligonucleotide-mediated mutagenesis as described in Sambrook et al., Molecular Cloning—A Laboratory Manual, 2nd ed., Vol. 1-3 (1989).

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar Variants will be sufficiently similar to the amino acid sequence of the polypeptides described herein. Such variants generally retain the functional activity of the polypeptides described herein. Variants include peptides that differ in amino acid sequence from the native and wild-type peptide, respectively, by way of one or more amino acid deletion(s), addition(s), and/or substitution(s). These may be naturally occurring variants as well as artificially designed ones.

As used herein, the term "percent (%) sequence identity" or "percent (%) identity," also including "homology," is defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

Polypeptides and polynucleotides that are sufficiently similar to polypeptides and polynucleotides described herein (e.g., SWEET1, SWEET4, SWEET5, SWEET7, or LST1_205437) can be used herein. Polypeptides and polynucleotides that about 85, 90, 91, 92, 93, 94 95, 96, 97, 98, 99 99.5% or more homology or identity to polypeptides and polynucleotides described herein (e.g., SWEET1, SWEET4, SWEET5, SWEET7, LST1_205437, and variants thereof) can also be used herein.

Constructs and Cassettes

A recombinant construct is a polynucleotide having heterologous polynucleotide elements. Recombinant constructs include expression cassettes or expression constructs, which refer to an assembly that is capable of directing the expression of a polynucleotide or gene of interest. An expression cassette generally includes regulatory elements such as a promoter that is operably linked to (so as to direct transcription of) a polynucleotide and often includes a polyadenylation sequence as well.

An expression cassette can comprise to a fragment of DNA comprising a coding sequence of a selected gene (e.g. SWEET1, SWEET4, SWEET5, SWEET7, LST1_205437, or combinations thereof) and regulatory elements preceding (5' non-coding sequences) and following (3' non-coding sequences) the coding sequence that are required for expression of the selected gene product. Thus, an expression cassette is typically composed of: 1) a promoter sequence; 2) one or more coding sequences ["ORF" ]; and, 3) a 3' untranslated region (i.e., a terminator) that, in eukaryotes, usually contains a polyadenylation site. The expression cassette is usually included within a vector, to facilitate cloning and transformation. Different expression cassettes can be transformed into different organisms including bacteria, yeast, plants, and mammalian cells, as long as the correct regulatory elements are used for each host.

A recombinant construct or expression cassette can be contained within a vector. In addition to the components of the recombinant construct, the vector can include, one or more selectable markers, a signal which allows the vector to exist as single-stranded DNA (e.g., a M13 origin of replication), at least one multiple cloning site, and a origin of replication (e.g., a SV40 or adenovirus origin of replication).

Generally, a polynucleotide or gene that is introduced into a genetically engineered organism is part of a recombinant construct. A polynucleotide can comprise a gene of interest, e.g., a coding sequence for a protein, or can be a sequence that is capable of regulating expression of a gene, such as a regulatory element, an antisense sequence, a sense suppression sequence, or a miRNA sequence. A recombinant construct can include, for example, regulatory elements operably linked 5' or 3' to a polynucleotide encoding one or more polypeptides of interest. For example, a promoter can be operably linked with a polynucleotide encoding one or more polypeptides of interest when it is capable of affecting the expression of the polynucleotide (i.e., the polynucleotide is under the transcriptional control of the promoter). Polynucleotides can be operably linked to regulatory elements in sense or antisense orientation. The expression cassettes or recombinant constructs can additionally contain a 5' leader polynucleotide. A leader polynucleotide can contain a promoter as well as an upstream region of a gene. The regulatory elements (i.e., promoters, enhancers, transcriptional regulatory regions, translational regulatory regions, and translational termination regions) and/or the polynucleotide encoding a signal anchor can be native/analogous to the host cell or to each other. Alternatively, the regulatory elements can be heterologous to the host cell or to each other. See, U.S. Pat. No. 7,205,453 and U.S. Patent Application Publication Nos. 2006/0218670 and 2006/0248616. The expression cassette or recombinant construct can additionally contain one or more selectable marker genes.

Methods for preparing polynucleotides operably linked to a regulatory elements and expressing polypeptides in a host cell are well-known in the art. See, e.g., U.S. Pat. No. 4,366,246. A polynucleotide can be operably linked when it is positioned adjacent to or close to one or more regulatory elements, which direct transcription and/or translation of the polynucleotide.

A promoter is a nucleotide sequence that is capable of controlling the expression of a coding sequence or gene. Promoters are generally located 5' of the sequence that they regulate. Promoters can be derived in their entirety from a native gene, or be composed of different elements derived from promoters found in nature, and/or comprise synthetic nucleotide segments. Those skilled in the art will readily ascertain that different promoters can regulate expression of a coding sequence or gene in response to a particular stimulus, e.g., in a cell- or tissue-specific manner, in response to different environmental or physiological conditions, or in response to specific compounds. Promoters are typically classified into two classes: inducible and constitutive. A constitutive promoter refers to a promoter that allows for continual transcription of the coding sequence or gene under its control.

An inducible promoter refers to a promoter that initiates increased levels of transcription of the coding sequence or gene under its control in response to a stimulus or an exogenous environmental condition. If inducible, there are inducer polynucleotides present therein that mediate regulation of expression so that the associated polynucleotide is transcribed only when an inducer molecule is present. A directly inducible promoter refers to a regulatory region, wherein the regulatory region is operably linked to a gene encoding a protein or polypeptide, where, in the presence of an inducer of the regulatory region, the protein or polypeptide is expressed. An indirectly inducible promoter refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by inducible promoter.

A promoter can be any polynucleotide that shows transcriptional activity in the chosen host microorganism. A promoter can be naturally-occurring, can be composed of portions of various naturally-occurring promoters, or may be partially or totally synthetic. Guidance for the design of promoters is derived from studies of promoter structure, such as that of Harley and Reynolds, *Nucleic Acids Res.,* 15, 2343-61 (1987). In addition, the location of the promoter relative to the transcription start can be optimized. Many suitable promoters for use in microorganisms and yeast are well known in the art, as are polynucleotides that enhance expression of an associated expressible polynucleotide.

A selectable marker can provide a means to identify microorganisms that express a desired product. Selectable markers include, but are not limited to, ampicillin resistance for prokaryotes such as *E. coli*, neomycin phosphotransferase, which confers resistance to the aminoglycosides neomycin, kanamycin and paromycin (Herrera-Estrella, *EMBO J.* 2:987-995, (1983)); dihydrofolate reductase, which confers resistance to methotrexate (Reiss, *Plant Physiol.* (*Life Sci. Adv.*) 13:143-149, (1994)); trpB, which allows cells to utilize indole in place of tryptophan; hisD, which allows cells to utilize histinol in place of histidine (Hartman, *Proc. Natl. Acad. Sci., USA* 85:8047, (1988)); mannose-6-phosphate isomerase which allows cells to utilize mannose (WO 94/20627); hygro, which confers resistance to hygromycin (Marsh, *Gene* 32:481-485, (1984)); ornithine decarboxylase, which confers resistance to the ornithine decarboxylase inhibitor, 2-(difluoromethyl)-DL-ornithine (DFMO; McConlogue, In: *Current Communications in Molecular Biology*, Cold Spring Harbor Laboratory ed., (1987)); deaminase from *Aspergillus terreus*, which confers resistance to Blasticidin S (Tamura, *Biosci. Biotechnol. Biochem.* 59:2336-2338, (1995)); phosphinothricin acetyltransferase gene, which confers resistance to phosphinothricin (White et al., *Nucl. Acids Res.* 18:1062, (1990); Spencer et al., *Theor. Appl. Genet.* 79:625-633, (1990)); a mutant acetolactate synthase, which confers imidazolione or sulfonylurea resistance (Lee et al., *EMBO J.* 7:1241-1248, (1988)), a mutant EPSPV-synthase, which confers glyphosate resistance (Hinchee et al., *BioTechnology* 91:915-922, (1998)); a mutant psbA, which confers resistance to atrazine (Smeda et al., *Plant Physiol.* 103:911-917, (1993)), a mutant protoporphyrinogen oxidase (see U.S. Pat. No. 5,767,373), or other markers conferring resistance to an herbicide such as glufosinate.

A transcription termination region of a recombinant construct or expression cassette is a downstream regulatory region including a stop codon and a transcription terminator sequence. Transcription termination regions that can be used can be homologous to the transcriptional initiation region, can be homologous to the polynucleotide encoding a polypeptide of interest, or can be heterologous (i.e., derived from another source). A transcription termination region or can be naturally occurring, or wholly or partially synthetic. 3' non-coding sequences encoding transcription termination regions may be provided in a recombinant construct or expression construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

The procedures described herein employ, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook et al., (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988); Fire, et al., *RNA Interference Technology From Basic Science to Drug Development*, Cambridge University Press, Cambridge (2005); Schepers, *RNA Interference in Practice*, Wiley-VCH (2005); Engelke, *RNA Interference* (RNAi): *The Nuts & Bolts of siRNA Technology*, DNA Press (2003); Gott, *RNA Interference, Editing, and Modification: Methods and Protocols* (*Methods in Molecular Biology*), Human Press, Totowa, N.J. (2004); and Sohail, *Gene Silencing by RNA Interference: Technology and Application*, CRC (2004)).

Vectors

Vectors for stable transformation of microorganisms and yeast are well known in the art and can be obtained from commercial vendors or constructed from publicly available sequence information. Expression vectors can be engineered to produce heterologous and/or homologous protein(s) of interest (e.g., SWEET1, SWEET4, SWEET5, SWEET7, or LST1_205437). Such vectors are useful for recombinantly producing a protein of interest and for modifying the natural phenotype of host cells.

If desired, polynucleotides can be cloned into an expression vector comprising expression control elements, including for example, origins of replication, promoters, enhancers, or other regulatory elements that drive expression of the polynucleotides in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Mini-chromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

To confirm the presence of recombinant polynucleotides or recombinant genes in transgenic cells, a polymerase chain reaction (PCR) amplification or Southern blot analysis can be performed using methods known to those skilled in the art. Expression products of the recombinant polynucleotides or recombinant genes can be detected in any of a variety of ways, and include for example, western blot and enzyme assay. Once recombinant organisms have been obtained, they may be grown in cell culture.

Methods of Use

Embodiments provide methods for co-utilization of two or more sugars in a fermentation reaction comprising contacting the microorganisms described herein with the two or more sugars under fermentation conditions such that the two of more sugars are co-utilized at an improved rate as compared to a control microorganism.

Additional embodiments provide methods for converting a lignocellulosic biomass into a product of added value comprising using an *Arabidopsis thaliana* SWEET1, SWEET4, SWEET5, or SWEET7 transporter polypeptide, a *Lipomyces starkeyi* LST1_204537 transporter polypeptide, a mutant thereof, or an analog thereof to co-ferment two or more sugars present in the lignocellulosic biomass.

Other embodiments provide methods of fermenting mixtures of sugars comprising contacting the microorganisms described herein with the mixture of sugars under fermentation conditions such that the mixtures of sugars are co-fermented at an improved rate as compared to a control microorganism.

A fermentation can occur in a bioreactor system. In general, fermentations can be completed in any suitable bioreactor. A bioreactor can be a fermenter, a stirred-tank reactor, an adherent bioreactor, a wave-type bioreactor, a disposable bioreactor, and the like. A bioreactor can comprise, for example, a hollow vessel or container that includes a bioreactor volume for receiving a cell culture within a fluid growth medium. A bioreactor system can further include, for example, a rotatable shaft coupled to an agitator such as impellers.

Yet other embodiments provide methods of producing ethanol comprising contacting the microorganisms described herein with two or more sugars under fermentation conditions such that the two of more sugars are co-utilized and ethanol is produced.

Embodiments provide methods of increasing the conversion rate of lignocellulosic biomass into biofuel and bioproduct comprising contacting the microorganisms described herein with a lignocellulosic biomass.

As used herein, "lignocellulosic biomass" refers to feedstock for production of, for example, ethanol, which includes materials such as agricultural residues (corn stover, crop straws, husks and bagasse), herbaceous crops (alfalfa, switchgrass), short rotation woody crops, forestry residues, waste paper and other wastes (municipal and industrial). Bioethanol production from these feedstocks is an attractive alternative for disposal of these residues. Lignocellulosic feedstocks do not interfere with food security and are important for both rural and urban areas in terms of energy security reason, environmental concern, employment opportunities, agricultural development, foreign exchange saving, socioeconomic issues etc.

"Converting a lignocellulosic biomass" refers to the transformation of the components of the biomass into one or more products or higher interest or value than the components of the biomass themselves. For example, the methods disclosed herein rely on the use of a lignocellulosic biomass comprising xylose and glucose, that can be, through fermentation, converted into biofuel, that have more added value than xylose and glucose.

Also provided are methods of generating biofuel comprising culturing the microorganisms described herein with a lignocellulosic biomass under suitable fermentation conditions.

In fermentation processes a genetically modified microorganism is cultivated in a fermentation medium or substrate that includes, for example sugars. A batch or continuous fermentation process can be used. The sugars can be, for example, pentose or hexose sugars, the sugars can be, for example, glucose, galactose, lactose, sucrose, arabinose, mannose, fructose, xylobiose, cellobiose, xylose, rhamnose, maltose, cellodextrins, 4-deoxy-L-erythro-5-hexoseulose uronate or combinations thereof. In an embodiment, two or more sugars are fermented. The fermentation medium or substrate can contain nutrients as required by the particular microorganism, including a source of nitrogen (such as amino acids proteins, inorganic nitrogen sources such as ammonia or ammonium salts, and the like), and various vitamins, minerals and the like.

Fermentation conditions, such as temperature, cell density, selection of substrate(s), selection of nutrients, and can be determined by those of skill in the art. Temperatures of the medium during each of the growth phase and the production phase can range from above about 1° C. to about 50° C. The optimal temperature can depend on the particular microorganism used. In an embodiment, the temperature is about 30, 35, 40, 45, 50° C.

During the production phase, the concentration of cells in the fermentation medium can be in the range of about 1 to about 150, about 3 to about 10, or about 3 to about 6 g dry cells/liter of fermentation medium.

A fermentation can be conducted aerobically, microaerobically, or anaerobically. Fermentation medium can be buffered during the fermentation so that the pH is maintained in a range of about 5.0 to about 9.0, or about 5.5 to about 7.0. Suitable buffering agents include, for example, calcium hydroxide, calcium carbonate, sodium hydroxide, potassium hydroxide, potassium carbonate, sodium carbonate, ammonium carbonate, ammonia, ammonium hydroxide and the like. The fermentation methods can be conducted continuously, batch-wise, or some combination thereof.

A fermentation reaction can be conducted over about 1, 2, 5, 10, 15, 20, 24, 25, 30, 36, 48, 50, 60, 70, 80, 90, or more or hours. Determinations of sugar consumption can be conducted after about 1, 2, 5, 10, 15, 20, 24, 25, 30, 36, 48, 50, 60, 70, 80, 90, or more or hours of fermentation by recombinant microorganisms. Determinations of product formation (e.g., amount of ethanol) can be conducted after about 1, 2, 5, 10, 15, 20, 24, 25, 30, 36, 48, 50, 60, 70, 80, 90, or more or hours of fermentation by recombinant microorganisms.

The basic techniques used for transformation and expression in bacteria and yeast are known in the art. Exemplary methods have been described in a number of texts for standard molecular biological manipulation (see Sambrook et al. (1989)). These methods include, for example, biolistic devices (see, for example, Sanford, *Trends In Biotech.*, 6: 299-302, (1988)); U.S. Pat. No. 4,945,050; use of a laser beam, electroporation, microinjection or any other method capable of introducing DNA into a host cell (e.g., an NVPO).

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

Figure 2A:
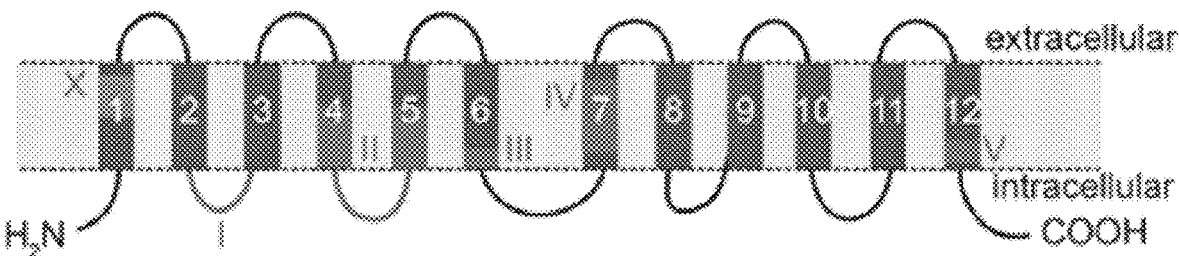
FIG. 2A illustrates the 12 transmembrane domains and conserved sequence motifs involved in the xylose specificity of the transporters. Most monosaccharide transporters in yeasts have 12 transmembrane domains (represented in blue). The conserved motifs identified in yeasts transporters are marked in orange (1-V). Motif X (marked in green) is a key motif involved in xylose specificity.
Figure 2B:
FIG. 2B illustrates a phylogenetic tree of the 17 *A. thaliana* SWEETs transporters, classified independently as mono- or disaccharide specific.
Figure 2C:
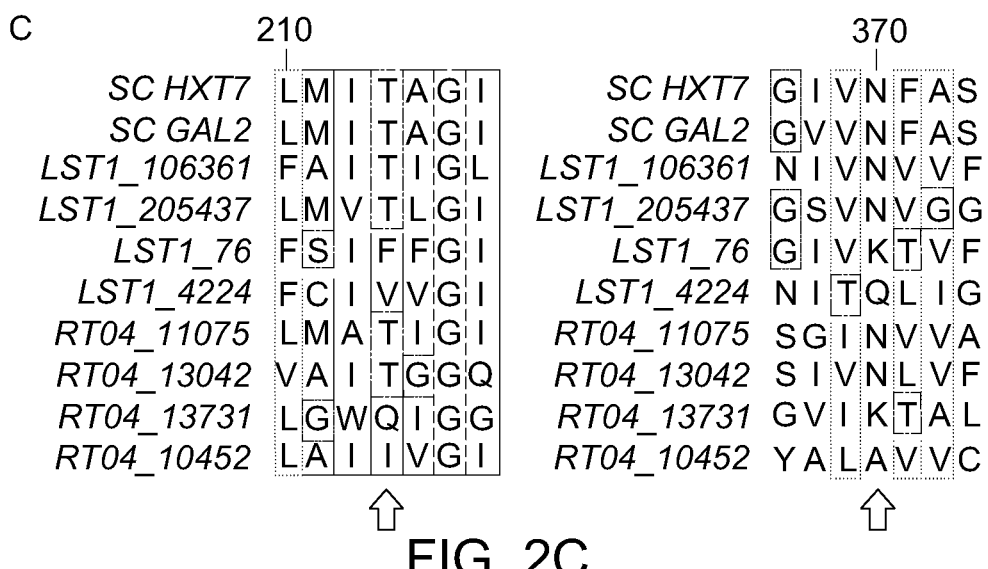
FIG. 2C illustrates multiple sequence alignment of putative transporters: T213 and N370 are conserved in glucose transporters in yeasts; the conserved motif G[G/F] XXXG and Thr213 and Asn370 residue in HXT7 involved in glucose and xylose specific transporters in *R. toruloides* and *L. starkeyi*. SEQ ID NO:13 is LMITAGI; SEQ ID NO:14 is FAITIGL; SEQ ID NO:15 is LMVTLGI; SEQ ID NO:16 is FSIFFGI; SEQ ID NO:17 is FCIVVGI; SEQ ID NO:18 is LMATIGI; SEQ ID NO:19 is VAITGGQ; SEQ ID NO:20 is LGWQIGG; SEQ ID NO:21 is LAIIVGI; SEQ ID NO:22 is GIVNFAS; SEQ ID NO:23 is NIVNVVF; SEQ ID NO:24 is GSVNVGG; SEQ ID NO:25 is GIVKTVF; SEQ ID NO:26 is NITQLIG; SEQ ID NO:27 is SGINVVA; SEQ ID NO:28 is SIVNLVF; SEQ ID NO:29 is GVIKTAL; SEQ ID NO:30 is YALAVVC.

Example 1. Identification of Putative Xylose Transporters in *Rhodosporidium toruloides* and *Lipomyces starkeyi* and Screening of *Arabidopsis thaliana* SWEET and Oleaginous Yeast Transporters for Glucose or Xylose Transport New sugar transporters in *R. toruloides* and *L. starkeyi* were identified. Multiple orthologs to HXT transporters from *S. cerevisiae* and XUT transporters from *P. stipites* were found; and those with 12 transmembrane domains and conserved sequence motifs (as illustrated in FIG. 2A) were selected. Conserved motif G[G/F]XXXG and Thr213 and Asn370 residue in HXT7 are involved in xylose specificity of the transporters, and were used to identify glucose and xylose specific transporters in *R. toruloides* and *L. starkeyi*. For *L. starkeyi*, LST1_106361 and LST1_205437 were identified as glucose transporters and LST1_76 was identified as a putative xylose transporter. RTO4_11075 and RTO4_13042 were identified as putative glucose transporters for *R. toruloides*, and RTO4_13731 and RTO4_10452 as putative xylose transporters (FIG. 2C). Protein ID's were picked from respective gene models at JGI mycocosm.

To screen sugar transport capability of the transporters the optimized recombinant xylose fermenting *S. cerevisiae* strain lacking 1-7 Hxt and Gal2 transporters (SR8D8) was used; the absence of those transporters rendered the yeast unable to grow on glucose or xylose. Growth kinetics of SR8D8 individually expressing all *A. thaliana* SWEETs and putative oleaginous yeast transporters for glucose and xylose transport capability were measured (FIGS. 2B, 2C). ScGal2 expressing SR8D8 were used as a positive control (FIG. 3). Most of the AtSWEETs and putative oleaginous transporters expressing strains were not able to grow on glucose or xylose. Only AtSWEET4, AtSWEET7 and LST1_205437 expressing strains showed substantial growth on xylose and glucose (FIG. 3A). AtSWEET1 can sustain growth of SR8D8 in glucose and xylose containing medium (FIG. 3); therefore, AtSWEET1 was also included alongside the other transporters.

Figure 4A:
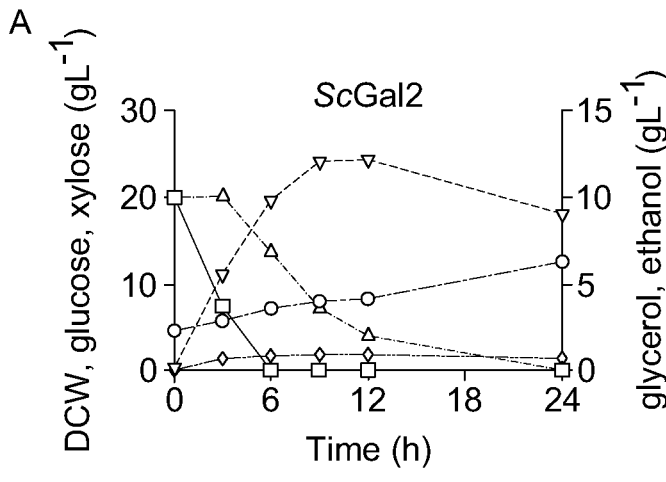
FIG. 4A-4F illustrates the glucose and xylose mixed sugar fermentation profile and inhibitory effect of glucose on xylose transport.
Figure 4B:
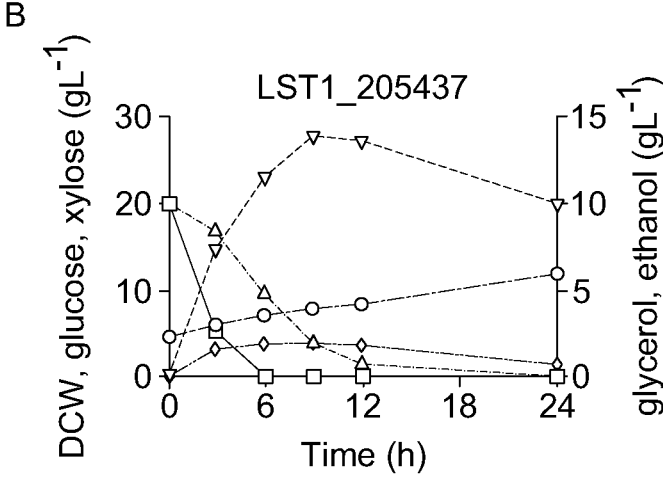
Figure 4C:
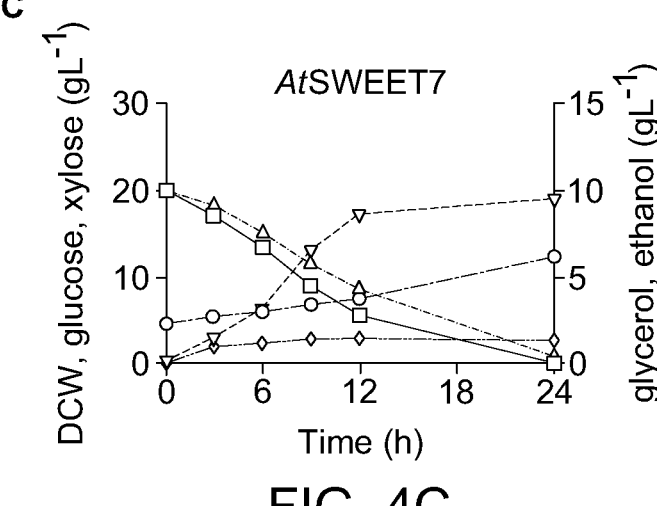
Figure 5A:
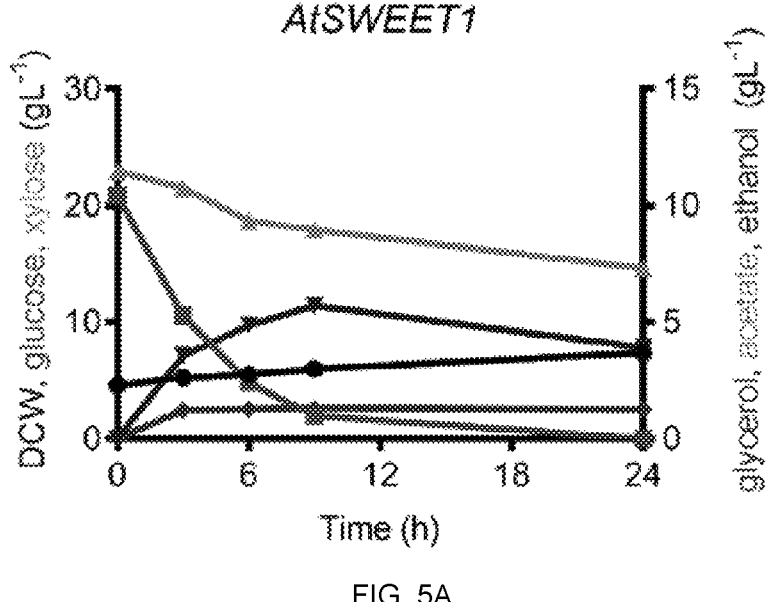
FIG. 5A-5B illustrates the glucose and xylose mixed sugar fermentation profile of SR8D8 expressing AtSWEET1 and AtSWEET4.
Figure 5B:
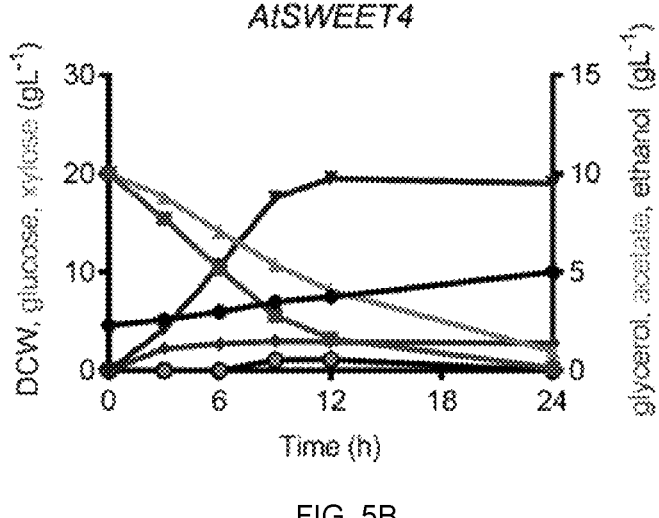

Example 2A. *A. thaliana* SWEET and *L. starkeyi* LST1_205437 Transporters Confer Glucose and Xylose Co-Fermentation Ability in Engineered Yeast To test if the selected transporters can enable consumption of both sugars simultaneously upon introduction to the SR8D8 strain, we performed flask fermentations with a mixture of glucose and xylose and monitored sugar consumption overtime. We used the SR8D8 expressing GAL2 as a baseline control for determining co-consumption phenotypes, because it can transport both glucose and xylose in a sequential manner (FIG. 4A). In addition, we included AtSWEET1 as an additional control for AtSWEETs, because confers growth of SR8D8 on glucose (FIG. 5A). Both AtSWEET4 and AtSWEET7 showed simultaneous co-utilization of glucose and xylose with different rates within 24 hours. While AtSWEET1 showed a complete preference for glucose with negligible xylose consumption (FIG. 5A), AtSWEET4 showed co-consumption of glucose and xylose with a faster glucose consumption rate than that of xylose (FIG. 5B). Surprisingly, AtSWEET7 enabled simultaneous co-consumption of glucose and xylose with almost the same rates of sugar consumption (FIG. 4C). LST1_205437 transporter from *L. starkeyi* showed co-consumption of glucose and xylose (FIG. 4B) but glucose consumption was faster than xylose consumption. In further experiments, we chose AtSWEET1 as a sole glucose transporter, AtSWEET7 as a glucose and xylose co-transporter, and LST1_205437 as a semi glucose and xylose co-transporter. AtSWEET7 transports both sugars simultaneously, but suffers from slow transport capacity. While LST1_205437 performs partial co-consumption, it has an efficient transport capacity for both glucose and xylose. The difference could be attributed to the structure and function of the transporters within the isolated organism.

Figure 6A:
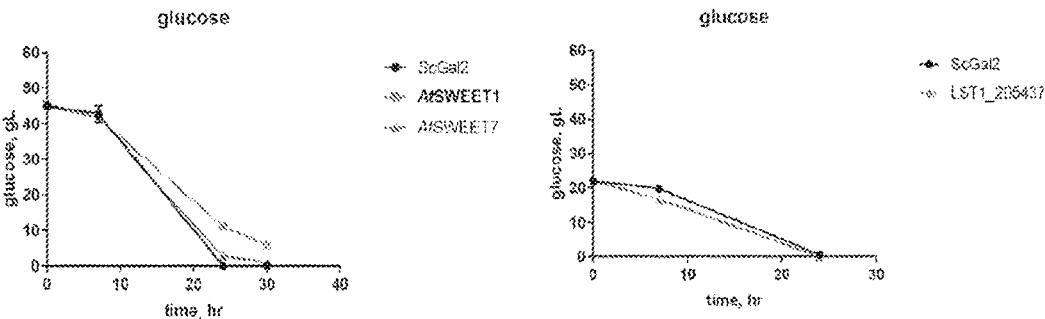
FIG. 6A illustrates glucose fermentation profile of AtSWEET1, AtSWEET7, LST1_205437 and ScGal2 in YP medium with 20 or 40 g/L of glucose.
Figure 6B:
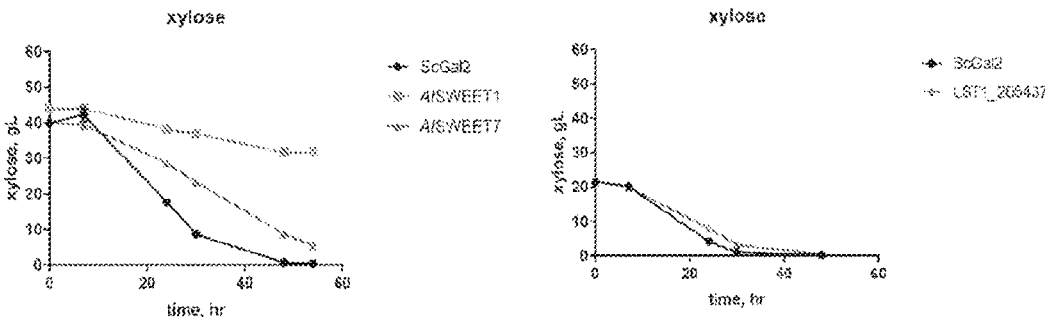
FIG. 6B illustrates xylose fermentation profile of AtSWEET1, AtSWEET7, LST1_205437 and ScGal2 in YP medium with 20 or 40 g/L of glucose.

Next, we evaluated fermentation performances of the SR8D8 transformants expressing AtSWEET1, AtSWEET7 and LST1_205437 under glucose or xylose conditions (FIG. 6). AtSWEET7 and LST1_205437 transporters enabled glucose and xylose fermentation, depleting all provided sugars. In contrast, AtSWEET1 enabled robust glucose fermentation but inefficient xylose fermentation with only 5 g/L of xylose consumption within 50 h.

Example 2B. Kinetic and Molecular Properties of *A. thaliana* SWEET7 and *L. starkeyi* LST1_205437

Figure 7A:
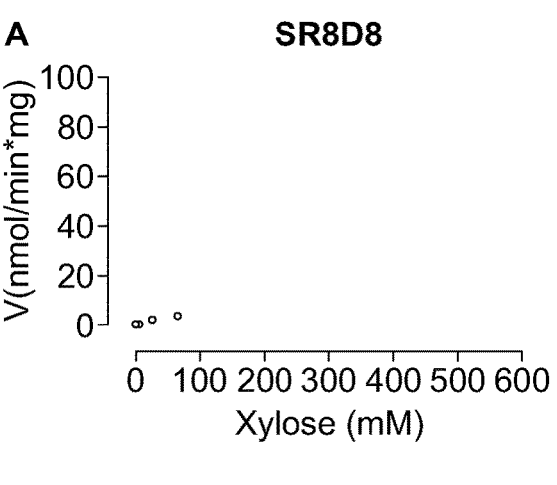
FIG. 7A illustrates sugar uptake kinetics by SR8D8.
Figure 7B:
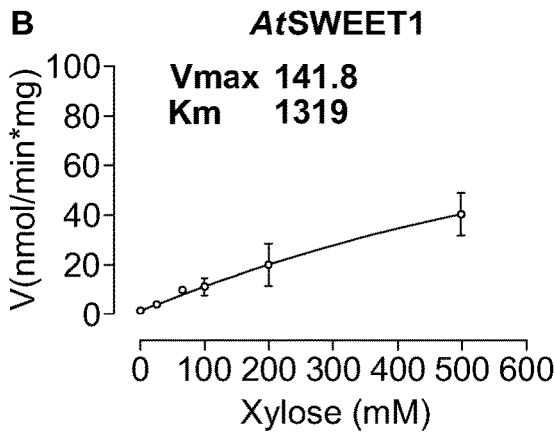
FIG. 7B illustrates sugar uptake kinetics by SR8D8 expressing AtSWEET1.
Figure 7C:
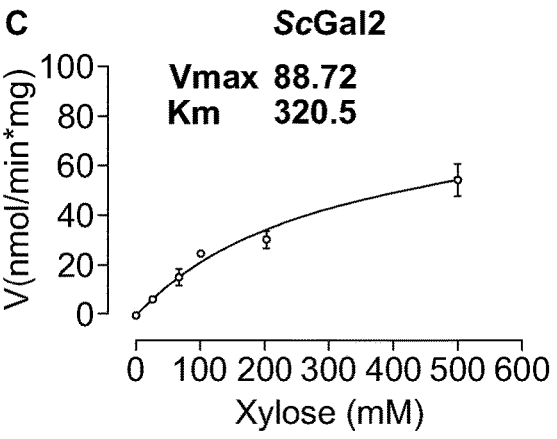
FIG. 7C illustrates sugar uptake kinetics by SR8D8 expressing ScGal2.
Figure 7D:
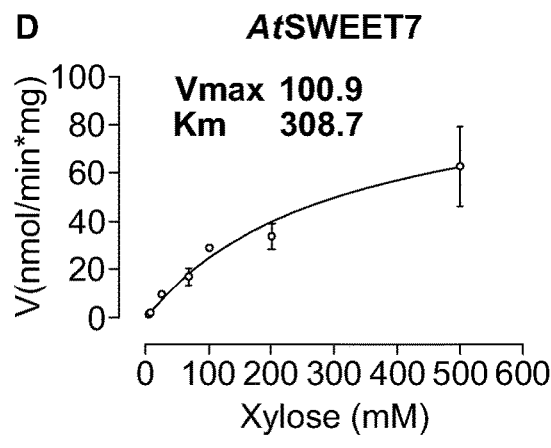
FIG. 7D illustrates sugar uptake kinetics by SR8D8 expressing AtSWEET7.
Figure 7E:
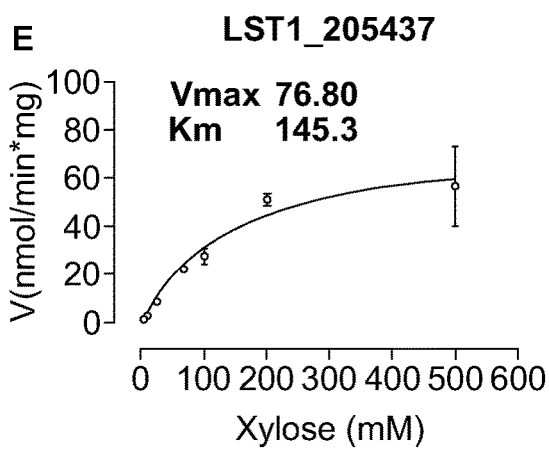
FIG. 7E illustrates sugar uptake kinetics by SR8D8 expressing LST1_205437. Initial xylose uptake (20 s) was measured at 30° C. over a concentration range of 1 to 500 mM xylose.
Figure 7F:
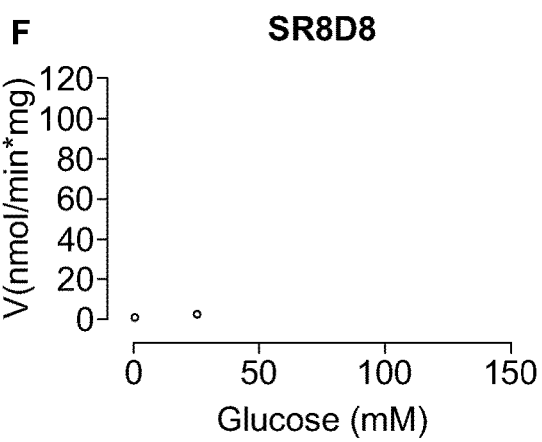
FIG. 7F illustrates sugar uptake kinetics by SR8D8.

To understand kinetic and molecular basis of AtSWEET7 and LST1_205437 glucose and xylose co-transport phenotypes, we performed radiolabeled sugar transport kinetics experiments, and in silico molecular modeling simulations with ScGal2 and AtSWEET1 serving as representative controls. ScGal2 was confirmed to be a high affinity glucose transporter ($K_M$=1.613 mM, $V_{max}$=38.33 nmol/min-mg), with low affinity toward xylose ($K_M$=320.5 mM) (FIG. 7C, and Table 1). Glucose transport kinetics of LST1_205437 was inferior to the ScGal2 transporter ($K_M$=4.975 mM, $V_{max}$=46.89 nmol/min-mg), whereas xylose kinetics was superior ($K_M$=145.3 mM, $V_{max}$=76.8 nmol/min-mg) (FIG. 7E, and Table 1). These transport kinetic differences were not noticeable during sole sugar fermentation, unlike mixed sugar fermentation (FIG. 7a-2b).

Figure 4D:
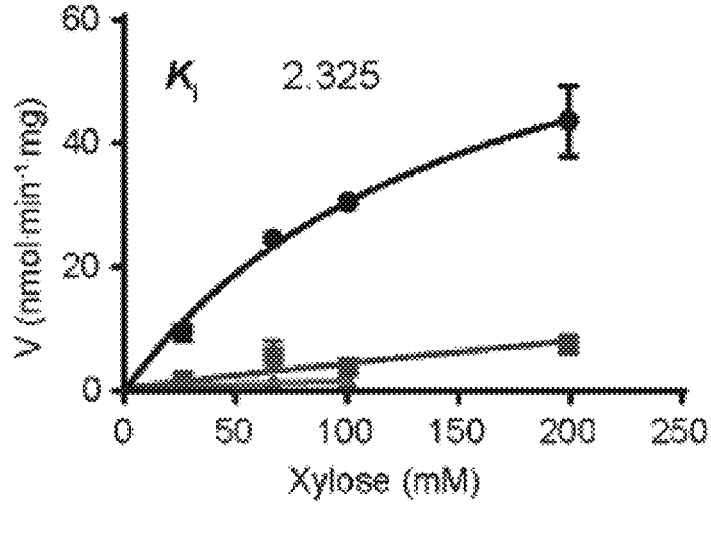
Figure 4E:
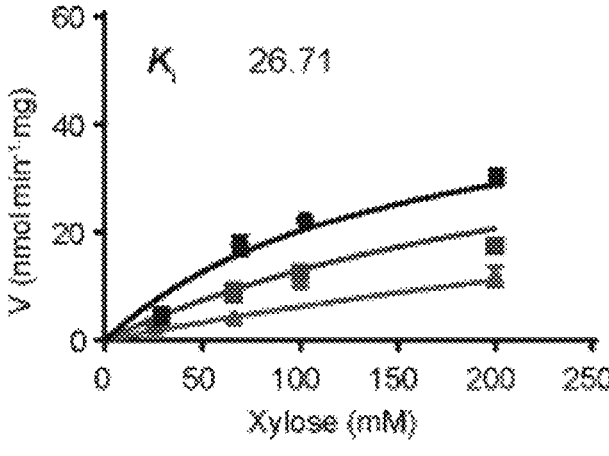
Figure 4F:
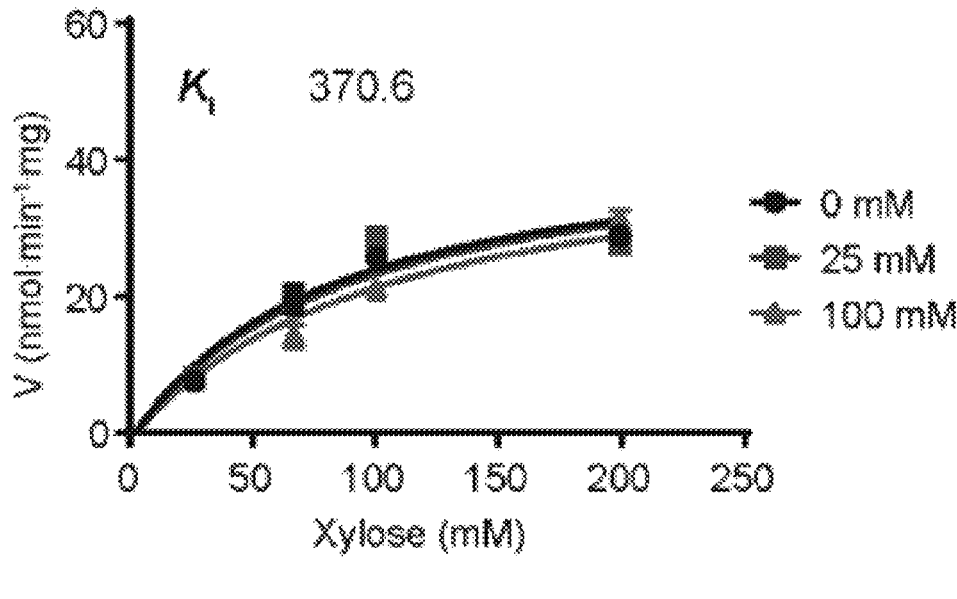
Figure 21A:
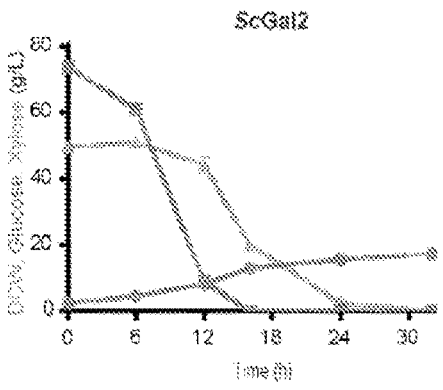
FIG. 21A-21C shows glucose and xylose mixed sugar fermentation profile using industrially relevant sugar concentrations.
Figure 21B:
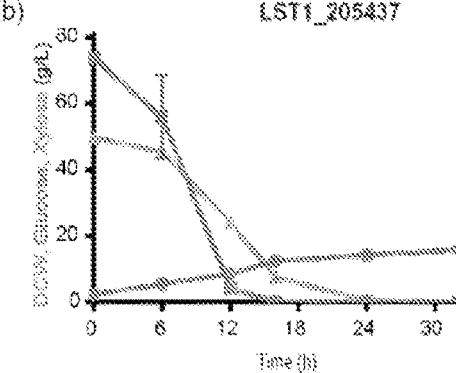
Figure 21C:
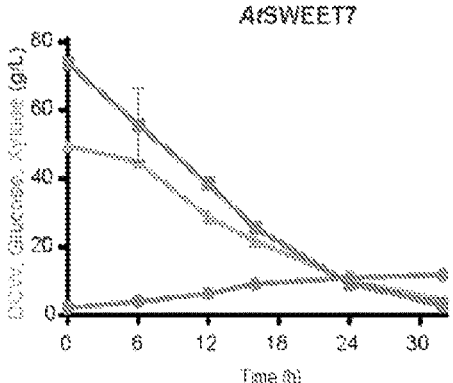

ScGal2 is consistent with the mixed sugar fermentation result (FIG. 4A). Interestingly, xylose transport by LST1_205437 was less inhibited by glucose than those by ScGal2 ($K_i$=26.7 vs 2.3 mM) (FIG. 4E). As a result, the LST1_205437 expressing strain showed a partial co-consumption of glucose and xylose (FIG. 4B). Remarkably, AtSWEET7 showed no inhibition of xylose transport by glucose (FIG. 4F, Table 1) (FIG. 4C). Next, we performed a mixed sugar fermentation experiment under industrially-relevant sugar concentrations of 7% glucose and 4% xylose to validate co-fermentation of AtSWEET7 and LST1_205437. The ScGal2 expressing strain exhibited a sequential utilization of glucose and xylose (FIG. 21A). The sugar utilization profile of the LST1_20437 expressing strain was consistent with the kinetics data, showing partial xylose and glucose co-consumption (FIG. 21B). The AtSWEET7 expressing strain showed co-consumption of glucose and xylose even at higher glucose concentrations, further supporting that AtSWEET7 is indeed glucose and xylose co-transporter which is insensitive even under high glucose concentrations (FIG. 21C).

Example 3. Alteration of N365 Amino Acid Residue in *L. starkeyi* LST1_205437 Changed Sugar Preference Asn370/376 residue in *S. cerevisiae* hexose transporters plays a critical role in glucose and xylose cotransport. Replacing Asn370/376 residue in ScHXT7 to either hydro-

TABLE 1

| Kinetic properties of ScGal2, AtSWEET7 and LST1_205437 | | | | | |
| --- | --- | --- | --- | --- | --- |
| | Glucose | | Xylose | | |
| Transporter | $K_m$ (mM) | $V_{max}$ (nmol · min⁻¹ · mg⁻¹) | $K_m$ (mM) | $V_{max}$ (nmol · min⁻¹ · mg⁻¹) | $K_i$ (mM) |
| ScGal2 | 1.6 ± 0.2 | 38.3 ± 1.4 | 320.5 ± 70 | 88.7 ± 10.0 | 2.4 ± 0.5 |
| AtSWEET7 | 74.1 ± 13.0 | 110.3 ± 7.2 | 308.7 ± 86 | 100.9 ± 14.8 | n.d. |
| LST1_205437 | 5.0 ± 1.0 | 47.0 ± 2.6 | 145.3 ± 43 | 76.8 ± 9.0 | 26.7 ± 6 |

Determined by zero-trans influx measurements with transporter-overexpressing SR8D8 and calculated with cell wet weight.
SEM is indicated.
n.d. is not detected.

We then compared transport kinetic properties of AtSWEET1 and AtSWEET7. The results showed that AtSWEET1 transports glucose more efficiently as compared to AtSWEET7, with very poor xylose transport kinetics (FIGS. 7B and 7D). These kinetics results of AtSWEET1 and AtSWEET7 are consistent with the fermentation results (FIG. 6A-6B) by the SR8D8 strains expressing AtSWEET1 and AtSWEET7.

Figures 17A, 17B, 17C, 17D:
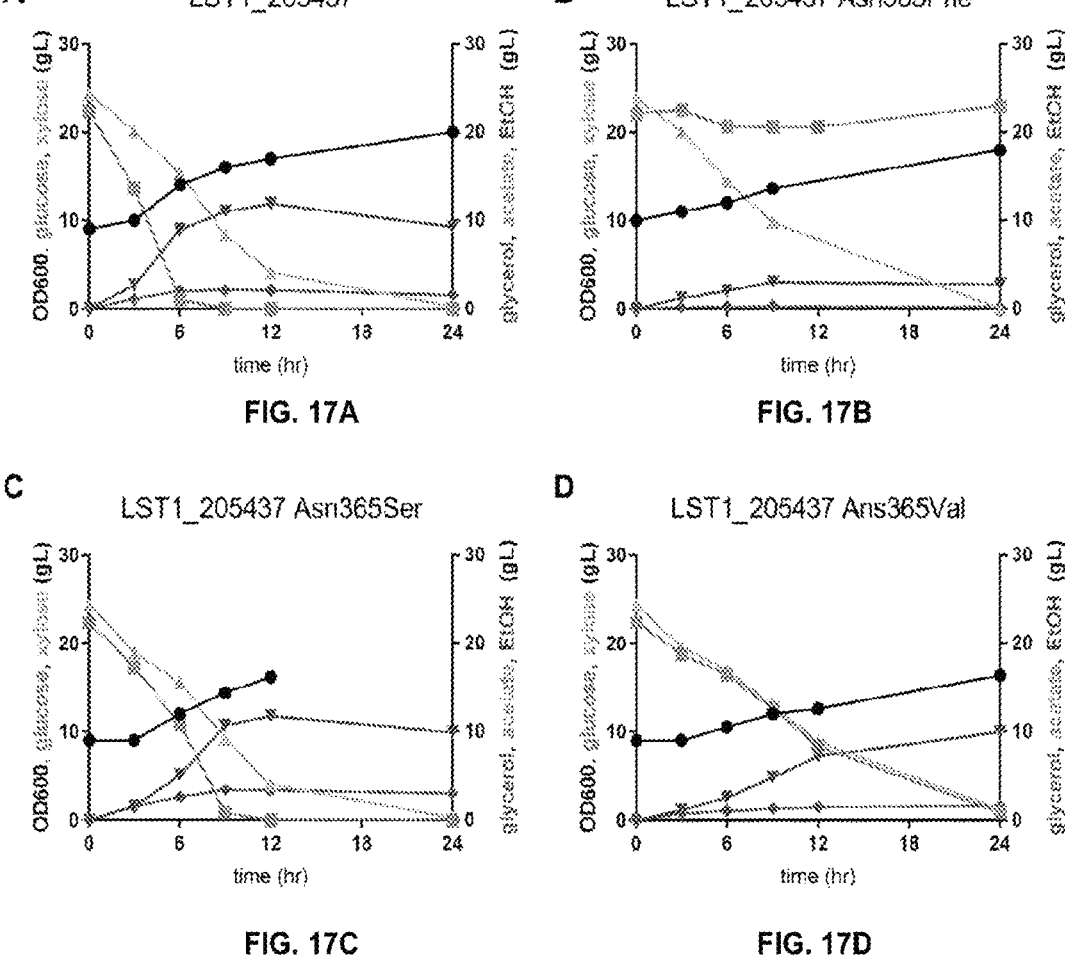
FIG. 17A illustrates glucose and xylose mixed sugar fermentation profile of SR8D8 expressing LST1_205437 (wild type).
FIG. 17B illustrates glucose and xylose mixed sugar fermentation profile of SR8D8 expressing LST1_205437 N365F mutant
FIG. 17C illustrates glucose and xylose mixed sugar fermentation profile of SR8D8 expressing LST1_205437 N365S mutant.
FIG. 17D illustrates glucose and xylose mixed sugar fermentation profile of SR8D8 expressing LST1_205437 N365V mutant. 20 g/L of glucose and xylose mixed sugar fermentation was done in YP medium. Symbols: glucose (square), xylose (triangle up), DCW (circle), ethanol (triangle down), glycerol (diamond).
Figure 18:
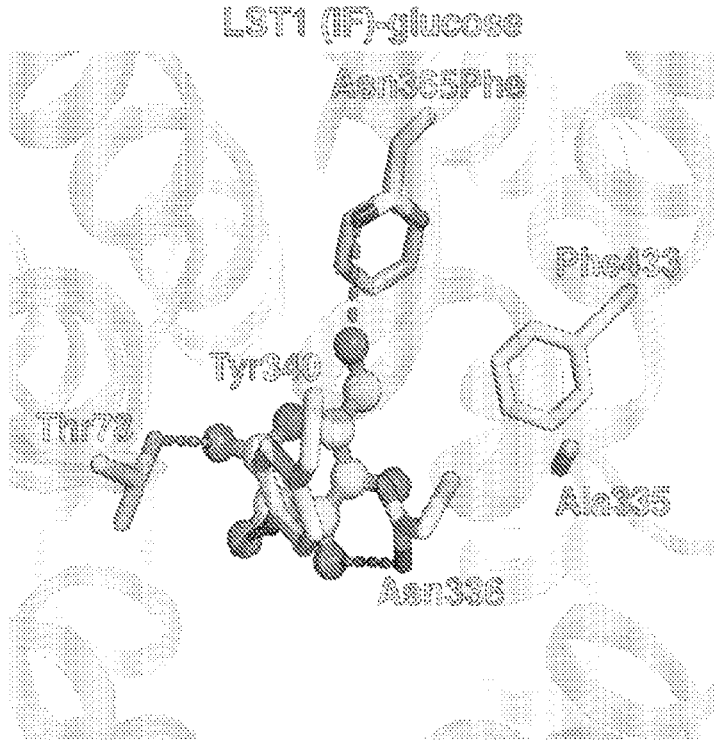
FIG. 18 illustrates the mutation of Asn365 to phenylalanine in LST1_205437. Asn365 form contact with glucose molecule in stabilize the IF state. The mutation to phenylalanine results in steric clash with substrate and affects the conformational transition to intermediate states and transport.

Individual sugar uptake kinetics results of LST1_205437 supported the partial glucose and xylose co-consumption phenotype. However, the engineered yeast expressing AtSWEET7 showed apparent co-consumption of glucose and xylose, while kinetics results indicated discrepancies in $K_M$ ($K_M$=75 mM for glucose and $K_M$=308 mM) (Table 1). These results prompted us to directly investigate the xylose transport rates by ScGal2, LST1_205437 and AtSWEET7 in the presence of glucose. We performed xylose uptake assay with 25 mM or 100 mM glucose, similar conditions that were used in previous study (22). As shown in FIG. 4D, xylose transport by ScGal2 was completely inhibited in the presence of glucose ($K_i$=2.3 mM). This kinetic behavior of phobic or hydrophilic side chain in Gal2 or Hxt7, derepressed xylose transport in the presence of glucose. Interestingly, LST1_205437 transporter retained Asn365 (Asn370 in Gal2) residue and shown partial inhibition of xylose uptake by glucose (FIG. 2C, FIG. 4A). The effects of the alteration of Asn365 residue to phenylalanine, serine or valine on glucose inhibition of xylose transport, and on the co-fermentation of both sugars were evaluated. Particularly, Asn370Phe mutation abolished glucose transport while retaining xylose, Asn365Ser and Asn365Val showed a co-fermentation phenotype (FIG. 17). Our computational study also shows that mutation to phenylalanine sterically hinders the binding mode of the glucose molecule and hence results in loss of transport function (FIG. 18). Altogether Asn365 residue mutation functioned not only in *S. cerevisiae* transporters but also in *L. starkeyi* LST1_205437.

Example 4. In Silico Modeling Beneficial Mutations Identification

Figure 19A:
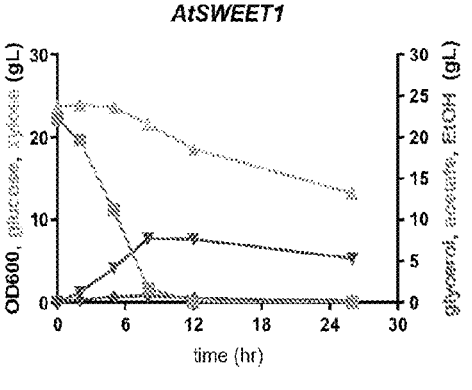
FIG. 19A illustrates glucose and xylose mixed sugar fermentation profile of SR8D8 expressing AtSWEET1 (wild type).
Figure 19B:
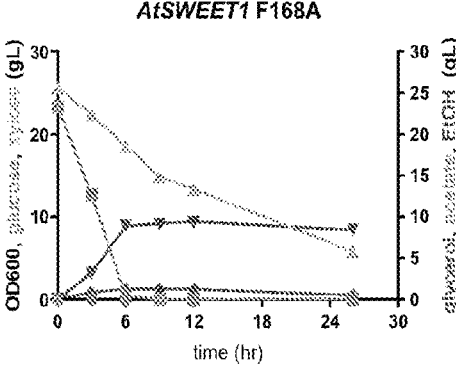
FIG. 19B illustrates glucose and xylose mixed sugar fermentation profile of SR8D8 expressing AtSWEET1 F168A. 20 g/L of glucose and xylose mixed sugar fermentation in YP medium. Symbols: glucose (square), xylose (triangle up), ethanol (triangle down), glycerol (diamond).
Figures 20A, 20B:
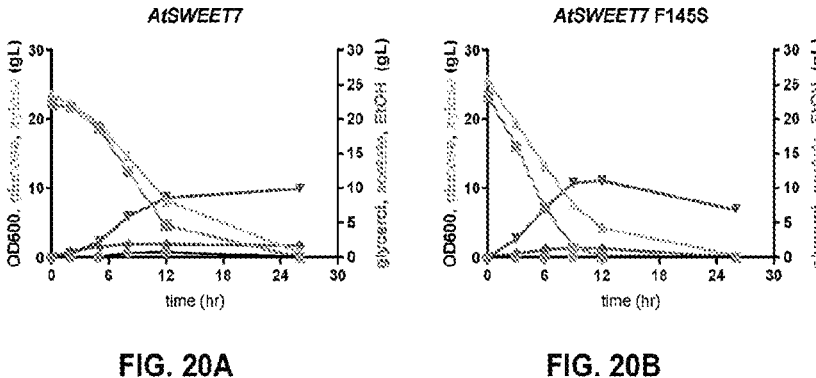
FIG. 20A illustrates glucose and xylose mixed sugar fermentation profile of SR8D8 expressing AtSWEET7 (wild type).
FIG. 20B illustrates glucose and xylose mixed sugar fermentation profile of SR8D8 expressing AtSWEET7 F145S.
Figure 20C:
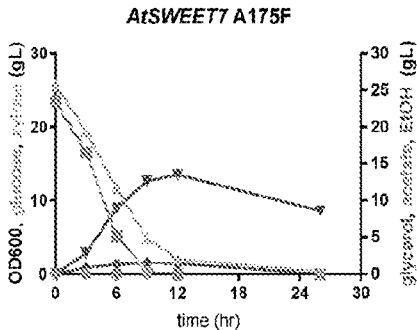
FIG. 20C illustrates glucose and xylose mixed sugar fermentation profile of SR8D8 expressing AtSWEET7 A175F. 20 g/L of glucose and xylose mixed sugar fermentation in YP medium. Symbols: glucose (square), xylose (triangle up), ethanol (triangle down), glycerol (diamond).

To further understand the mechanism of sugar transport in AtSWEET transporters, several mutations based on in silico sugar transport modeling analysis were created. The single mutation F168A in AtSWEET1 was identified as capable of improving both glucose and xylose uptake rate (FIG. 19). The single mutations N145S or A175F were found capable of improving glucose and xylose uptake rate in AtSWEET7 (FIG. 20). Overall, those mutations were found useful for the improvement of AtSWEET capacity to cotransport glucose and xylose simultaneously. Using in silico modeling beneficial mutations that improves sugar transport capability of AtSWEET1 and AtSWEET7 have been successfully identified.

Example 5. Materials and Methods

Medium and Cell Growth Conditions

Under non-selective conditions, all strains were grown on yeast extract peptone dextrose (YEPD or YPD) agar plates (2% w/v agar, 1% w/v yeast extract, 2% peptone, 2% glucose). A single colony from YPD agar plate was inoculated into 2 mL YPD liquid medium to obtain seed cultures. For growth study, the seed cultures were then used to inoculate 25 mL of YPD and YPX medium (10 g/L yeast extract, 20 g/L peptone, and 20 g/L xylose or glucose) in a 125 mL shake flask with a starting OD600 of 1. The cells were then grown at 30° C. and 250 rpm.

For flask fermentation, a single colony was inoculated to 5 or 25 mL YPE (2% w/v agar, 1% w/v yeast extract, 2% peptone, 5% ethanol) supplemented with 200 μg/ml of geneticin to obtain seed cultures. Subsequently, seed cultures were inoculated to 25 mL of YPD, YPX, and YPDX medium (10 g/L yeast extract, 20 g/L peptone, and 20 g/L xylose and/or glucose) in a 125 mL shake flask with a starting OD600 of 1, 5, or 10 for flask fermentation. Flask fermentations were maintained at 30° C. and 250 rpm. $CaCO_3$ at 50 g/L was added for high sugar fermentations in YPDX medium (10 g/L yeast extract, 20 g/L peptone, 70 g/L glucose, and 40 g/L xylose.

A xylose fermenting *S. cerevisiae* yeast (SR8) with HXT1-7Δ, GAL2Δ deletions was used for transporter screening and characterization (SR8D8). SR8D8 was grown in YPE medium/plate (10 g/L yeast extract, 20 g/L peptone, and 5 g/L ethanol). The codon optimized sugar transporter genes from *L. starkeyi, R. turoloides* and *A. thaliana* (see Table 3) were expressed in SR8D8 using G418 resistance dominant marker harboring plasmid for glucose and/or xylose transport characterization. SRD8 strains transformed with plasmid containing KanMX marker conferring resistance to G418 (geneticin) were propagated on YPE supplemented with 200 μg/ml of geneticin. For growth and flask fermentation experiments all media was supplemented with 200 μg/ml of geneticin for plasmid maintenance. Biomass was calculated from the $OD_{600}$ measured using a Biomate 5 UV-visible spectrophotometer (Fisher, NY, USA). All growth rates were measured using a Bioscreen C plate reader system (Growth Curves USA, Piscataway, NJ, USA). A 2 μL inoculum of fully grown culture was added into 200 μL YP (+200 μg/ml Geneticin) with varying concentrations of different sugars. A wide band filter (420-580 nm) was used to measure optical density. Bioscreen C values represent mean value from three biological replicates. In all cases, the Bioscreen C was set to maintain a temperature of 30° C. and high aeration through high continuous shaking.

Plasmid Construction and Transformation

All transporters were cloned into p42K-GPD1p-CYC1t plasmid harboring 2p replication origin and KanMX marker conferring resistance to g418 (geneticin) antibiotic. For AtSWEET transporters p42K-GPD1p-CYC1t plasmid were linearized with BamHI and XhoI enzymes and PCR amplified AtSWEET digested with BamHI and XhoI was ligated with T4 ligase according to manufacturer's protocol. For *R. turoloides* and *L. starkeyi* p42K-GPD1p-CYC1t plasmid were linearized with BamHI and EcoRI enzymes and PCR amplified transporters digested with BamHI and EcoRI was ligated with T4 ligase according to manufacturer's protocol. All plasmids were transformed into *E. coli* DH5a for propagation and maintenance. SR8D8 yeast strain was grown on YPE medium for transformation. SR8D8 transformations were performed using LiAc method according to Gietz et al. Transformants were selected on YPE plates supplemented with 200 μg/ml of geneticin. LST1_205437 N370 mutant variants were synthesized from Twist Biosciences (Twist Biosciences, CA, USA) and cloned as previously described.

C14 Labeled Sugar Uptake Assay

SR8D8 containing the respective plasmid was grown on selective YPE medium to an $OD_{600}$ of 1-1.5, harvested by centrifugation, and washed twice in ice-cold uptake buffer (100 mM potassium phosphate, pH 6.5). C14 labeled sugar uptake assay was done according to Boles and Oreb. Radioactivity was analyzed in a Beckman-Coulter LS6500 multipurpose liquid scintillation counter (Beckman-Coulter, CA, USA).

Uptake was measured at sugar concentrations 0.2, 1, 5, 25, and 100 mM for glucose and 1, 5, 25, 66, 100, 200, and 500 mM for xylose. Inhibition of xylose uptake by glucose was measured at 25, 66, and 100 mM xylose with additional 25 and 100 mM unlabeled glucose. Sugar solutions contained 0.135-0.608 μCi of D-[U-$^{14}$C]-glucose (290-300 mCi/mmol) or D-[1-$^{14}$C]-xylose (55 mCi/mmol) (PerkinElmer, MA, USA). Calculation of $K_m$ (Michaelis constant), $V_{max}$ (maximal initial uptake velocity), and K (inhibitor constant for competitive inhibition) was done by nonlinear regression analysis and global curve fitting in Prism 7 (GraphPad Software) with values of three independent measurements.

Transporter Identification

Orthologs of known sugar transporters were identified in *R. toruloides* and *L. starkeyi* using BlastP. Glucose transporters from *S. cerevisiae* (HXT7, HXT2, HXT1, HXT3) and xylose transporters from *P. stipites* (XUT5, XUT2, RGT2, XUT3) were used as templates for blast search. Search results were filtered by e-value and gene regulation. MEGA X 10.0.1 tool was used to perform ClustalW alignment for the filtered putative sugar transporters and identify conserved structural domains and amino acid residues. The alignment results were edited using the Jalview 2.8 tool for enhanced visual presentation.

Transporter Modeling

The homology models of Scal2, LST_205437, AtSWEET1, and AtSWEET7 were constructed using Modeller. The OF and IF models of Scal2 and LST_205437 were built using the structural template XylE (PDB ID: 4GBZ[5] and 4JA4[6]). The 3D coordinates of XylE structures were obtained from protein databank. The structural models of OC and OF states of AtSWEET1 and AtSWEET7 were obtained using MD predicted structures of OsSWEET2b as template. The IF OsSWEET2b was used to build both AtSWEET1 and AtSWEET7 IF models. Molecular docking was performed using Autodock software package. The PDBQT format files for protein and substrate molecules were obtained using AutoDock Tools. The grid files were generated using Autogrid4 and docking was performed using Autodock4. The docking files were visualized using pymol (The PyMOL Molecular Graphics System, Version 1.7, Schrodinger, 2015).

TABLE 2

| Name | amino acid sequence |
|---|---|
| AtSW1 SEQ ID NO: 1 | MNIAHTIFGVFGNATALFLFLAPSITFKRIIKNKSTEQFSGIPYPMTLLNCLLS AWYGLPFVSKDNTLVSTINGTGAVIETVYVLIFLFYAPKKEKIKIFGIFSCVL AVFATVALVSLFALQGNGRKLFCGLAATVFSIIMYASPLSIMRLVVKTKSV EFMPFFLSLFVFLCGTSWFVYGLIGRDPFVAIPNGFGCALGTLQLILYFIYCG NKGEKSADAQKDEKSVEMKDDEKKQNVVNGKQDLQV |
| AtSW4 SEQ ID NO: 2 | MVNATVARNIAGICGNVISLFLFLSPIPTFITIYKKKKVEEYKADPYLATVL NCALWVFYGLPMVQPDSLLVITINGTGLAIELVYLAIFFFFSPTSRKVKVGL WLIGEMVFVGIVATCTLLLFHTHNQRSSFVGIFCVIFVSLMYIAPLTIMSKVI KTKSVKYMPFSLSLANFLNGVVWVIYALIKFDLFILIGNGLGTVSGAVQLIL YACYYKTTPKDDEDEEDEENLSKVNSQLQLSGNSGQAKRVSA |
| AtSW7 SEQ ID NO: 3 | MVFAHLNLLRKIVGIIGNFIALCLFLSPTPTFVRIVKKKSVEEYSPIPYLATLI NCLVWVLYGLPTVHPDSTLVITINGTGILIEIVFLTIFFVYCGRQKQRLIISAV IAAETAFIAILAVLVLTLQHTTEKRTMSVGIVCCVFNVMMYASPLSVMKM VIKTKSVEFMPFWLSVAGFLNAGVWTIYALMPFDPFMAIPNGIGCLFGLAQ LILYGAYYKSTKRIMAERENQPGYVGLSSAIARTGSEKTANTNQEPNNV |
| LST1 SEQ ID NO: 4 | MGFLGFLNRSQASEPVEKESTATTPSEGRTPQRPLSPAVGVPLEQDFETQLS AKDAPLLAFILGGVASVGGFMFGYQTGQISGFLEMSDFKTRFAACNSQTG QCTFSAARQGTIVGLFSIGTLIGSLIAAPIADRIGRRLTISFWAFFFMIGTVLEI SSSHVWVQFAMGRFVGGLGIGALSVVVPMYQSESTPRMIRGVIVSSYQLM VTLGIWLAYMINWGTESLQGSQSWRITNGMSFLWALVLGIAILGLPESPRY AYRVGREEEARKNMARLYKLSPNHPIINLEIQEIQEKLDAERVGGDHPWYE IFTGPRMLYRTILGMVLQAGQQLTGANYFFYGTTVFSATGLSNSYVTQII LGSVNVGGTIAGLWLIENCGRRKALMGGAAWMFMCFMVFAFVGHFSLD HQNPEATPQAGAALVVFSCLFIIAFAMTWGPIVWAIVGELYPARYRATCM GLATSSNWLFNFLIGFFTTFITGDIDYLYGLVFAGCCFALFFIVYFFVIETKG RSLEEIDTMYVLHVNPINSAKWDSSQLMRDGDGLVNTDDLYLEAGGNRF AKDEHSAHEMIPSHDENAPGPSHTSHADIEKAESSGAESRDAL |

TABLE 3

| Name | Codon optimized DNA sequences used for SR8D8 expression |
|---|---|
| AtSW1 SEQ ID NO: 5 | ATGAACATCGCTCACACTATCTTCGGCGTTTTCGGAAATGCAACTGCTC TGTTTCTTTTCTTGGCTCCTTCGATAACATTCAAGAGAATCATCAAGAA CAAATCCACTGAACAATTCTCTGGTATCCCTTATCCAATGACTCTCCTC AACTGTCTCCTCTCTGCTTGGTATGGACTTCCCTTTGTGTCAAAAGACA ACACACTTGTGAGCACAATCAATGGCACAGGAGCAGTGATCGAAACAG TCTACGTGTTAATCTTTCTTTTCTACGCACCAAAGAAGGAGAAAATTAA GATCTTTGGTATCTTCTCTTGCGTTTTGGCTGTATTCGCAACAGTAGCTC TCGTCTCTCTCTTTGCTCTTCAAGGAAACGGTAGAAAACTCTTTTGTGGT CTCGCAGCTACTGTTTTCTCCATCATCATGTACGCTTCTCCACTCTCCAT CATGAGATTGGTGGTAAAGACGAAGAGTGTAGAGTTTATGCCATTCTTT TTGTCACTCTTTGTCTTCCTCTGTGGTACTTCGTGGTTCGTCTATGGTCT AATCGGTCGTGACCCTTTTGTTGCAATCCCAAATGGGTTTGGATGTGCA TTAGGGACACTGCAATTGATACTATACTTCATCTACTGTGGAAACAAAG GAGAGAAATCTGCAGATGCTCAGAAAGATGAGAAGTCAGTGGAGATG AAAGATGATGAGAAGAAGCAGAATGTGGTTAATGGAAAGCAAGACCT TCAAGTTTAA |
| AtSW4 SEQ ID NO: 6 | ATGGTTAACGCTACAGTTGCGAGAAACATTGCCGGCATTTGTGGAAAT GTCATCTCCTTGTTCTTGTTCTTATCTCCCATACCTACGTTCATAACCAT ATACAAGAAGAAAAAGGTGGAGGAGTACAAAGCTGACCCATACTTAG CCACGGTTCTAAATTGCGCACTATGGGTCTTTTATGGCTTACCAATGGT TCAACCAGATAGTCTCCTTGTGATCACCATAAATGGTACCGGTTTAGCC ATTGAGCTGGTGTATCTCGCTATCTTCTTCTTCTTTTCTCCAACTAGTCG CAAGGTGAAAGTGGGGCTATGGTTAATAGGAGAGATGGTGTTTGTAGG AATAGTAGCCACATGCACATTGCTATTGTTCCACACACATAACCAGAG ATCTTCTTTTGTTGGAATCTTTTGTGTCATTTTTGTTAGTCTCATGTATAT TGCTCCTCTCACCATCATGAGTAAGGTGATCAAGACCAAAAGTGTGAA GTACATGCCATTCTCTCTCTCACTTGCCAATTTCCTCAATGGTGTCGTTT GGGTTATTTATGCACTTATTAAGTTCGACCTTTTCATTTTGATTGGAAAT GGACTTGGAACGGTATCAGGAGCAGTACAACTTATACTCTATGCTTGCT ATTACAAGACAACACCAAAAGATGATGAAGATGAAGAAGATGAGGAG AATCTTTCTAAGGTTAACTCTCAGTTACAACTTAGTGGCAACAGTGGAC AAGCTAAACGAGTTTCAGCTTGA |
| AtSW7 SEQ ID NO: 7 | ATGGTGTTTGCACATTTGAACCTTCTTCGGAAGATTGTGGGGATTATAG GAAACTTCATCGCTCTATGTCTGTTCTTGTCACCAACGCCAACATTTGTT CGGATAGTGAAAAAGAAGTCAGTGGAGGAATATTCACCAATACCGTAT TTAGCGACTCTTATAAACTGTTTGGTTTGGGTTCTTTACGGACTACCAA CGGTGCATCCGGACAGCACATTGGTCATTACAATAAACGGCACAGGGA TCTTGATCGAAATCGTATTCCTTACGATCTTTTTCGTTTATTGTGGCCGC |

TABLE 3-continued

| Name | Codon optimized DNA sequences used for SR8D8 expression |
|------|----------------------------------------------------------|
| | CAAAAACAGCGGTTGATAATATCCGCTGTTATAGCGGCTGAAACCGCG |
| | TTCATAGCTATTCTTGCGGTTTTGGTATTAACTCTCCAACACACTACCGA |
| | AAAACGTACTATGAGTGTTGGAATCGTATGTTGCGTTTTCAACGTTATG |
| | ATGTACGCTTCTCCATTGTCTGTTATGAAAATGGTAATAAAAACAAAAA |
| | GTGTGGAGTTCATGCCGTTTTGGTTATCGGTAGCTGGATTTCTAAACGC |
| | AGGCGTTTGGACAATTTATGCTCTCATGCCTTTCGACCCATTCATGGCT |
| | ATACCAAATGGAATTGGATGTTTATTTGGGCTAGCTCAACTAATATTGT |
| | ATGGTGCCTACTATAAGTCCACCAAAGAATAATGGCGGAAAGAGAAA |
| | ACCAACCTGGTTACGTCGGTTTATCAAGTGCGATCGCTCGTACCGGATC |
| | TGAGAAAACCGCGAATACCAACCAAGAACCTAACAATGTTTAA |
| | |
| LST1_20 | ATGGGTTTCCTAGGCTTTCTTAATCGATCTCAGGCCTCAGAGCCAGTTG |
| 5437 | AAAAGGAGTCAACTGCGACCACGCCTTCAGAAGGAAGGACTCCCCAAC |
| SEQ ID | GCCCGCTCTCACCTGCTGTAGGTGTACCTCTAGAGCAAGACTTTGAGAC |
| NO: 8 | TCAGCTGTCTGCGAAGGATGCTCCCTTGTTGGCATTTATTCTGGGTGGT |
| | GTGGCATCCGTGGGTGGCTTTATGTTTGGATACCAAACTGGTCAAATTT |
| | CAGGTTTCCTTGAGATGAGTGATTTCAAAACTCGTTTTGCCGCATGCAA |
| | TAGTCAAACTGGTCAATGTACTTTCAGCGCGGCGAGGCAAGGAACCAT |
| | TGTCGGTCTCTTTTCGATTGGTACACTTATTGGCTCTCTCATCGCTGCCC |
| | CCATCGCTGATCGCATCGGCCGCCGCCTGACCATCTCCTTTTGGGCGTT |
| | CTTCTTCATGATTGGCACTGTCCTGGAGATTTCAAGTTCACATGTATGG |
| | GTGCAGTTCGCTATGGGCCGATTCGTTGGTGGTCTCGGTATCGGAGCCC |
| | TTTCGGTAGTCGTTCCCATGTATCAGAGTGAGAGTACCCCCAGGATGAT |
| | TCGAGGCGTCATTGTGAGCAGCTATCAATTGATGGTCACACTGGGTATT |
| | TGGCTCGCTTATATGATCAACTGGGGTACCGAAAGTCTTCAAGGTAGCC |
| | AATCGTGGCGTATCACCAACGGAATGTCCTTTCTCTGGGCCCTCGTCCT |
| | CGGTATCGCTATTCTCGGTCTTCCGGAGTCTCCTCGCTATGCCTACCGTG |
| | TAGGGCGAGAGGAAGAGGCGCGCAAGAACATGGCTCGCCTTTACAAGT |
| | TAAGTCCGAATCATCCCATCATTAACCTGGAGATTCAAGAGATTCAAG |
| | AGAAGCTCGACGCTGAACGGGTTGGTGGCGATCATCCTTGGTACGAAA |
| | TCTTCACTGGTCCTCGCATGCTGTACCGCACCATACTCGGTATGGTCTT |
| | GCAGGCTGGTCAACAGCTTACTGGTGCCAATTACTTCTTTTACTACGGT |
| | ACCACCGTCTTCAGCGCCACGGGTCTCTCTAACTCCTATGTTACCCAGA |
| | TTATCTTGGGTTCCGTTAACGTAGGTGGTACGATTGCCGGCCTTTGGCT |
| | CATCGAAAACTGCGGCCGTCGCAAAGCCCTTATGGGTGGAGCAGCTTG |
| | GATGTTCATGTGCTTCATGGTCTTTGCTTTTGTTGGTCACTTTTCCTTGG |
| | ATCATCAAAACCCGGAAGCTACTCCCCAGGCTGGAGCGGCGCTAGTCG |
| | TTTTCTCGTGTCTTTTCATCATTGCATTTGCAATGACATGGGGTCCAATA |
| | GTCTGGGCCATCGTGGGAGAGCTCTACCCCGCCCGTTACCGCGCTACCT |
| | GCATGGGTCTGGCTACATCATCTAACTGGCTCTTCAACTTCCTTATCGG |
| | ATTTTTCACCACATTCATTACGGGTGATATCGACTACCTCTACGGCCTT |
| | GTATTTGCCGGGTGCTGTTTCGCTCTTTTCTTCATTGTCTATTTCTTCGTG |
| | ATTGAGACTAAGGGCCGCTCCCTCGAGGAGATTGATACCATGTATGTCC |
| | TGCATGTCAACCCAATCAACAGTGCCAAGTGGGATAGCTCCCAGTTGA |
| | TGAGAGATGGGGATGGACTCGTCAATACTGATGACCTGTATCTCGAAG |
| | CTGGTGGTAACAGGTTCGCCAAGGATGAGCACAGCGCCCATGAGATGA |
| | TCCCAAGCCATGATGAGAATGCACCGGGCCCGAGCCACACATCCCACG |
| | CAGATATCGAGAAGGCCGAGAGCAGCGGTGCTGAGAGCCGCGATGCTC |
| | TCTGA |
| | |
| RT88 | ATGAATCCTGAGAATGAATCAGTTCCGGCGTCAAAAGCGACGACTCTG |
| GluT1 co | GCAGGTAGCGCCGCGCCCAGCAGGGCAGCTTCAGTCAAGAAGGAGGC |
| (Protein | ACACTCCGCGCCCAGCTCAAGGCCAGGTTCAACTTTCCACCCCCAGGAT |
| ID: | GAATTAGATGGAGTGCCTTCAAAGGATCGTGCTCCACCATTCGTTGTTG |
| 11075) | CACTTTGCTTATTTCAGAGCCTGGCAGGGTTACTATTTGGATGGGAGCA |
| SEQ ID | AGGTGTGATAGCAGGACTTACAACTAATCCCGTGTATCAACGTAGATTT |
| NO: 9 | GGGGAACCCGATCCTACGAGCGCATCAGGGTATTCTCTGCCAAGTACG |
| | AGGCTTAGCTTGATAACCGGGTTTATGTCATTGGGTGCGCTTTTTGGGG |
| | CTTTACTAATTGGACAGTTGTTACGTAGAACTGGAATAAAAATTGCTAT |
| | CATCTTCTCCTTGGTTATCTATGCAGCCGGCATCGCGATCGAGACCAGT |
| | GGTCAATCCCAGTACGGCCAGGAGATAGCTGGAAGGTTCGTAACTGGT |
| | TTTGGTGTGGGGAGTCTTAGTCTTTTAGCGCCCCTGTATCAAGCTGAGT |
| | GCAGCCCTAAACACCTAAGAGGATTAATTACATCTACATACCAGTTGAT |
| | GGCGACGATCGGCATCTTCCTATCAAACGCAGTGAATTACGCACAACA |
| | TGACAAGGGCACTGACTTTTCCTGGAGGTTCCCCATAGCCATTCAGTTC |
| | ATATGGGCAGCCGTCGTGTTCGTGGGGACTGTGTTGGCACCAGAAAGT |
| | CCTAGATATTACGTTCAGAGAGACAATGTGGACAGAGCAAGAGTAAAC |
| | CTTGCGAAACTACGTGGACTTGACGAACAGGATCCCGAACTACTAGCA |
| | GAACTGGATGTAATCATCAAGGGGGTTGAGGATGAGAAGCTTGCCGCG |
| | GACGCAACATACCTGGACTGCTTCAGAATGAAGGATAGGATGTTGCTT |
| | AGGACCATGAATGGTGTGATGGTGCAGTGGGGACAACAATGGTCTGGA |
| | GTCAATTTTTTTTTTTAGTTACGGTAATAAATTTTTTGCTACCTCTGGGAT |
| | CAAGGATCCTTACCAAAACGCAGCTAATACTTTCAGGCATAAACGTTGTC |
| | GCAACTTTTCCTGGGATCCTTGCGGTGGATCGTCTAGGCCGTAGGACAC |
| | TATTATTTATTGGCAGTGCTATGATGTTCAGTGGGCAAATAATCGCCGG |
| | AAGCGTATCCACGGCCAAGCCGAACGATCCCGCGGCTGGTAAGGCACT |
| | AATCTTTGCTTCATGTTGGTTCATCGCCGGGTTTGCTTGCAGTTGGGGA |
| | CCATTGGGCTGGGTGGTAGCGGCAGAACAATTTCCATTAAAGATAGCC |

TABLE 3-continued

| Name | Codon optimized DNA sequences used for SR8D8 expression |
|---|---|
| | CCTCTATGCGTTTCCTTGGCAACTGCGAGTAATTGGCTTAACAACTTCA<br>TTATAGCGATCATTGTGCCCTATATTACCGATCCCGGCTACGGCAATAT<br>AGGAACCAAAATTACATTCATGTGGGCCGGCACTGAGTTTCTGGCATTC<br>CTATACACCTTCTTCTTTATTCCGGAAACGAAGGGTCTTTCCTTGGTTCA<br>GGTCGATGAACTTTACCTGACCGGGGTTCCCGCATGGAGGTCTGCGAGT<br>TGGACTCCGTACGGCGGGGCGACAGCACGTAATCAAAAGGATAGAGAC<br>GAAGCCAAGCGTTTGAAGCTTGGGACTGAGGCAAGCCACCATGAGAAC<br>GTGCCTACCAAAAGAAATTTAGCCGAAGACGTCTAA |
| RT88<br>GluT2 co<br>(Protein<br>ID:<br>13042)<br>SEQ ID<br>NO: 10 | ATGTCTAGCACTCCACCTGCCCCTCTACTTGGACCCGATAAAGCCCCGT<br>CCACGAGGTCTAACTCATCCGGTGAGCTGGACTTTGACAAACTTAACA<br>ATAAGGCAACACTAAAGCATCTGTCCCAATCTAGACTTGAGGTCGACG<br>AATCAGTAGTAAGAGCTGAGGGGGAGGAGAGGACTACGTTCTTTGTTT<br>GGTGGCTTGTCATCGCTGCAGCGACCGGCGGCCTATTGTTTGGCTACGA<br>CACGGGCGTCATCGGTGGCGCGCTTGTCCACAAGGACGTTGCTTCTGAC<br>TTGCATCGTGTCCCGCTTGGTTCTTTCGATAAAGAGTTACTGACATCAG<br>CTACAACGCTGGGGGCACTGATTGCCGGCTTCTCATCCGGGGTCCTAGC<br>CGACATTATTGGCAGAAAGATTGTCATAGGTCTGGCTGATGCAATATTC<br>ATAATCGGGGCTGTTCTTCAGGCAGTGAGTTATGGTGCGAACGCGTACT<br>GGATTATGGCGGTTGGCCGTCTAATCATAGGCTTTGGGGTGGGGATTAGC<br>TAGTTTGGTTGTACCTTTATATATTGGCGAGCTAAGTCCAACCAGCTTA<br>AGGGGTAGATTGGTAACACTTAACGTCGTCGCGATTACCGGAGGGCAA<br>GTGATTGCTTATTGCCTGAACCTTGCTTTTCAAAATGTCACGCACGGGT<br>GGCGTTTTATGGTTGGTTTAGGAGCAATTCCTCCGGCCTTGCAGTTACT<br>TATGCTGATTTATCTACCCGAGAGTCCTCGTTTTCTGCTTAGGCATGAC<br>AAGTTAGAGGCGACTGTTACCATACTGCGTAAGATATACCCATACGCC<br>ACTGAAGAACAGTTACACTTAAAAGCGGATGTAATTTCTAAAAGTGTA<br>AAGGAGAACATGGGTCATAGGGCAACATTCGTCCAAACTTGGAAAAGA<br>TTGCACCTGAATGGACCTAACTTTCGTGCACTGGTTGTCGCATGTGGAT<br>TACAGGGCATCCAACAACTATGCGGCTTCAACACGTTGATGTATTACGC<br>TCCTACTCTTTTCCAATCAGTAGGATTTGACAACTCCCTTGTGATCGGTC<br>TGGTTATTTCCATTGTGAACCTGGTTTTCACAATCGTAGCTTTGTTTATT<br>ATCGACAGAGTGGGGCGTAGGCGTATTGCTTGTAGCACAGTGCCGGGC<br>ATGTGTGGGGCGTTAATCCTAGCAGCCGTAGCCTTCCACTTCTTAACGA<br>TTCATACCGGGGGGAAATTGCCTGACAACGGTGCGGGCCTGAACGACA<br>AGTGGAGCCCGGTCGTACTTACTGCAATGTTGGTCTATGTAGCTTTCTA<br>CGCAACCGGTATTGGGAACATACCATGGCAACAGGGGGAGCTATTCGA<br>GATGGATGTGCGTGGAATGGGCACCGCCCTATCTACTACGTGCAATTG<br>GGGAGGTAATTTAATCATAGGCTCTACTTTCCTGTCCTTGATTGACAGA<br>ATAACCGCCGCAGGTGCGTTTGGGTTCTACGCCGGACTTTGCTTTCTTG<br>GGTCAATATTCGTCTTTTTTTTGTACCCCGAGACAAGTGGTCTATCACTT<br>GAGGAGACTAGAGAGGTCTTCCTTACAGGATTTGGGATTAGGAAGGCC<br>AATAGGATGCGTAAACAGAAGATGGCCGCGCTAGCTCAGGTCCGTGAT<br>GCAGACGACGACGCTACCGTCTAG |
| RT88<br>XylT1 co<br>(Protein<br>ID:<br>10452)<br>SEQ ID<br>NO:11 | ATGGTAGCGCCCAAAAGGTCATTATTGACTAAGTTTACGAGGAATCAA<br>TACTTGGTTGGATCTCTTCCAACCTTAGGTGGATTGATTTTCGGATTGG<br>ATATAAGCTCAATGTCCGCTCAACTGTCTAATCCATATTATTTAGAAAC<br>ATTCAATCATCCTGATTCTACCCTACAAGGTTTGATTAATGCTGTCATG<br>CCCCTTGGCAGTTTCTTCGGTGCGTTGTTTAATAGTTATTTGTGTGACTT<br>GATCGGTAGGAAATGGTGTATTATAATCTCAGGATGGTTGTGGGTGATC<br>GGAGCCATTGTACAGAGTACAGCTAAAAATGTAGGTGCGCTAATGGGG<br>GGTCGTGTCGTGGCTGGACTGGCAGTCGGTCTGGCAAGCGCGATCGTG<br>ACTATCTACCAAGCTGAAATAACTAAGCCTCAGTTACGTGGAAGGATA<br>GTTTCAGTTCAACAACTGGCCATCATCGTTGGAATAGCGGTGCAATACT<br>TTATCCAGTTTGGGTTCAGCTACCTAGAATCTGACAAGTCCTTTCGTAT<br>CCCTTGGGCCCTTCAGCTTATTCCTGGCGCCATTCTTGGTTCACTGATGT<br>TTATCTTTCCTGAATCCCCCAGGTGGCTAATGGACCACGGAAGGGACG<br>ATGAGGCACTTCAGATCCTAGCTGACGTGCATGCTGCGGGTGATACGG<br>AAGACGCTCTAGTCCAGCTAGAGTTCTCTGAGATAAAGAGGCAAATAG<br>CTTTTGATAACCAACAAGGCGCAAAATCTTACCTAGACCTACTTAAACC<br>AGATGTAAGATTGCGTGTCTTCTTGGGATGCGCCGATCAAATGTGGTCA<br>CAGCTTTCCGGGATGAACGTGATGATGTATTATGTTGTGTATGTTTTTC<br>AGGGTGCGGGGTTACAAGGAAGAAGGGCCGAGTTAATCGCTTCAAGCG<br>TTCAATACGCCTTAGCTGTCGTTTGCACGTTACCGGCTGTAATTTGGCTT<br>GATAAGATCGGAAGGAGACCCTTATTAGTCGGTGGTAGTGCTGCCATG<br>GCTACGTGCCTAATGATTGTCGGCGCCTTACAAAAGACCCTGGGGCAT<br>AAAATAGAGGGCGCAGAAGCCGCTGCTACAACGACGTGGGTGGTGACC<br>GGGCATAAAAGCGGATCCTATGCTATTATTGTGTTTTCCTACCTTTTTGT<br>CTGCAGTTTTTCCGCGACTCTTGGTCCCTGTTCTTGGACATACGCCTCAG<br>AGATCTTCCCGACGAGAGTGAGAGGCAAAGCTGTATCATTCGCCACCG<br>CCTCCAATTGGATCTTTAACTTCATTCTTAGTATGACTACTCCGCCCGCA<br>TTTCGTAACATTCAGTACCGTTGTGTACTTTCTTTACGGTACGTTTAACAT<br>ATGCTCTTTTCTACATTTCTTTCTTATGTATCCTGAGACTAAAGGAAGGA<br>CTTTAGAGGAGATGGAAGAGATATTTGATGGTACTAACACTTTCACCGC<br>ATGGAGGGTGCCTCCGGCCAAAGGCGTCAAGAACGTAACTGACCTAGA<br>ATCCTGA |

TABLE 3-continued

| Name | Codon optimized DNA sequences used for SR8D8 expression |
|------|--------------------------------------------------------|
| RT88 | ATGGTGAATCTATTTGAAAGGATAGAGGACAGACCCACACCCAAGGCA |
| XylT2 co | GTGTACAACTGGCGTGTATACGCTTGTGCCATCGTCGCGGCAACAGCG |
| (Protein | GCTATAATGATAGGATACGACTCCGCATTTATCGGCACAAGTATGGCGT |
| ID: | TAGCGTCCTTTAAGAACGAATTTGGATTGGCTCACAAAACTAGTAAAC |
| 13731) | AATTTGCAGCTATTTCTGCTAATATTGTCAGCACCTATCAAGGGGGATG |
| SEQ ID | TTTCTTTGGGTCTTTATTAGGATATCCTTTAGGACAGATCTTAGGTAGG |
| NO: 12 | AGGCTAGGTTTTATTTATCTCTGCGTTAGTTTTTGTGCTTGGGGCAGGTGT |
| | AATGTTAGCGGCCGATGGGGCTAGAGGGCTTGGGCCGATATATGGGGG |
| | GAGAATAGTAGCGGGTTTAGGTATTGGTGCCGCTAGCAATTTAACACC |
| | GTTGTACATAAGCGAAATCGCTCCCCCGGCTATTAGAGGTCAGCTGGTT |
| | GGAATGTACGAACTTGGTTGGCAAATTGGGGGCCTTGTAGGTTTCTGGA |
| | TTAACTACGGCGTAAGCGAGAATATACCGAGCTCTCATAAGCAGTGGC |
| | TTATTCCCTTTGCGGTTCAACTGATTCCTGGCGCTTTATTTGCTATCGGA |
| | ATACCATTTTTTGTCAGGGAATCCCCTCGTTGGTTAATAACGAGGGGTA |
| | GGCGTTCCGAGGCGCTGAAAAACCTGTGTTATATTAGGAAGTTACAGC |
| | CTGAGGACGCCTACATTATAAACGAAATGAATGAAATTGACGTGCAAG |
| | TTGAACACGATCGTACTGCCGTAGGTGAGGGATTCTGGGCTCCGTTCAG |
| | GCAAGTGTTCGGAAAGGGCTTTCTATTCAGGAGAATGCTAATAACTAC |
| | CAGTTTGTTTGTGTGGCAGAATGGTACGGGCATCAACGCCGTCAATTAC |
| | TACAGCCCGACCATCTTTAAAAGTATAGGGGTGACAGGAAATACATCA |
| | TTGTTAACCACGGGCGTATTCGGAGTAATAAAAACTGCCCTTGCTCTAG |
| | TATGGTGCTTCATAATAATAGATCGTTTCGGACGTCGTGGGATCCTGTT |
| | GGTAGGCGCTACCGGTGGTGCTTTAAGTATGTTTGCGATTGGGGCGTAC |
| | AACAAGATCCAAAACCCGGCAGCCCATCCAACGCCTAACCTACCGCCG |
| | GGAGGGAAGGCGGCGATGTTTTTTTTCTATCTGTGGACTGCCTTCTACG |
| | CAGTGTCCTGGAACGGAACACCGTGGGTCGTCAACTCAGAGTCATTTCC |
| | GGGCGCAGTTAGACAAGTTACCCAGTGCTTCGCAGCGACGTCCAACTG |
| | GTTGTGGAACTTCGTTATCTCTAGGGCTACGCCTACCATGTTTCTGAAT |
| | ATGGGCCACTCTGGATACGGAGTGTACTTATTTTTCGCTGCGATGCAGG |
| | TATTATCTATCCCCTATATCTGCTTTCTACTGCCTGAGACGAGAAATATC |
| | CCTTTAGAAGAGATGGATAGACTTTTCGCTCAGAGGAATGTATGGAAT |
| | GCAAATAAAATTGTTATGGCAGAGCTGCGTCGTGAGCATGAACTGGGT |
| | GCTAAAAACCCCGCATATCTGAAACCGACTGCCAGCCAAGAACAAATT |
| | GAGAACGCAAGCTCTTCAGATGGCGAGAAAGTTTGA |

---

What is claimed is:

1. A recombinant yeast comprising one or more heterologous polynucleotides encoding an *Arabidopsis thaliana* SWEET7 (AtSWEET7) transporter polypeptide comprising 90% or more sequence identity to SEQ ID NO: 3, wherein an Asn amino acid at position 145 (Asn145) of the AtSWEET7 transporter is substituted with a Ser amino acid (Asn145Ser substitution), an Ala amino acid at position 175 (Ala175) is substituted with a Phe amino acid (Ala175Phe substitution), or both the Asn145 and the Ala175 are respectively substituted with a Ser and a Phe (Asn145Ser substitution and an Ala175Phe substitution).

2. The recombinant yeast of claim 1, wherein the recombinant yeast does not express endogenous or heterologous hexose transporter HXT1-7, and does not express heterologous or endogenous Gal2 transporter.

3. The recombinant yeast of claim 1, wherein the recombinant yeast is selected from *Saccharomyceraceae* sp., *Saccharomyces cerevisiae, Saccharomyces pastorianus, Saccharomyces beticus, Saccharomyces fermentati, Saccharomyces paradoxus, Saccharomyces uvarum Saccharomyces bay anus; Schizosaccharomyces* sp., *Schizosaccharomyces pombe, Schizosaccharomyces japonicus, Schizosaccharomyces octosporus, Schizosaccharomyces cryophilus, Torulaspora* sp., *Torulaspora delbrueckii, Kluyveromyces* sp., *Kluyveromyces marxianus, Pichia* sp., *Pichia stipitis, Pichia pastoris, Pichia angusta, Zygosaccharomyces* sp., *Zygosaccharomyces bailii, Brettanomyces* sp., *Brettanomyces inter medius, Brettanomyces bruxellensis, Brettanomyces anomalus, Brettanomyces custersianus, Brettanomyces naardenensis, Brettanomyces nanus, Dekkera bruxellensis, Dekkera anomala; Metschmkowia* sp., *Issatchenkia* sp., *Issatchenkia orientalis, Kloeckera* sp. *Kloeckera apiculate, Aureobasidium* sp., *Aureobasidium pullulans*, and *Corynebacterium glutamicum*.

4. The recombinant yeast of claim 1, wherein the recombinant yeast is *Saccharomyces cerevisiae*.

5. The recombinant yeast of claim 1, wherein the recombinant yeast has improved sugar co-utilization of two or more sugars as compared to a control yeast.

6. The recombinant yeast of claim 5, wherein the two or more sugars are a first sugar that is glucose and a second sugar that is selected from galactose, lactose, arabinose, mannose, sucrose, fructose, xylobiose, cellobiose, xylose, rhamnose, 4-deoxy-L-erythro-5-hexoseulose uronate, maltose, cellodextrins, or combinations thereof.

7. The recombinant yeast of claim 1, further comprising a heterologous polynucleotide encoding a RT04_11075 or RT04_13042 putative glucose transporter and/or a heterologous polynucleotide encoding a RT04_13731 or RT04_10452 putative xylose transporter.

8. A method for co-utilization of two or more different sugars in a fermentation reaction comprising contacting the recombinant yeast of claim 1 with two or more different sugars under fermentation conditions such that the two or more different sugars are co-utilized at an improved rate as compared to a control yeast.

9. The method of claim 8, wherein the two or more different sugars are a first sugar that is glucose and a second sugar that is selected from galactose, lactose, arabinose, mannose, sucrose, fructose, xylobiose, cellobiose, xylose, rhamnose, 4-deoxy-L-erythro-5-hexoseulose uronate, maltose, cellodextrins, or a combination thereof.

10. A method of producing ethanol comprising contacting the recombinant yeast of claim 1 with two or more different sugars under fermentation conditions such that the two of more sugars are co-utilized and ethanol is produced.

11. The method of claim 10, wherein the two or more different sugars are present in a lignocellulosic biomass.

12. The method of claim 11, wherein the lignocellulosic biomass comprises glucose, xylose, galactose, fructose, sucrose, xylodextrin, cellobiose, arabinose, mannose, lactose, or combinations thereof.

13. A bioreactor for continuous conversion of lignocellulosic biomass into biofuel comprising the recombinant yeast of claim 1.

14. The recombinant yeast of claim 5, wherein the two or more sugars are glucose and xylose.

15. The recombinant yeast of claim 1, wherein the *Arabidopsis thaliana* SWEET7 (AtSWEET7) transporter polypeptide comprises SEQ ID NO:3.

* * * * *